(12) United States Patent
Greenhalgh et al.

(10) Patent No.: US 8,535,380 B2
(45) Date of Patent: *Sep. 17, 2013

(54) FIXATION DEVICE AND METHOD

(75) Inventors: E. Skott Greenhalgh, Lower Gwynedd, PA (US); John-Paul Romano, Chalfont, PA (US)

(73) Assignee: Stout Medical Group, L.P., Perkasie, PA (US)

( * ) Notice: Subject to any disclaimer, the term of this patent is extended or adjusted under 35 U.S.C. 154(b) by 275 days.

This patent is subject to a terminal disclaimer.

(21) Appl. No.: 12/779,865

(22) Filed: May 13, 2010

(65) Prior Publication Data
US 2011/0282453 A1 Nov. 17, 2011

(51) Int. Cl.
A61F 2/44 (2006.01)
(52) U.S. Cl.
USPC ............................ 623/17.15; 606/90
(58) Field of Classification Search
USPC ............................ 623/17.11–17.16; 606/90
See application file for complete search history.

(56) References Cited

U.S. PATENT DOCUMENTS

| | | | |
|---|---|---|---|
| 646,119 A | 3/1900 | Clamer et al. | |
| 3,659,587 A | 5/1972 | Baldwin | |
| 4,204,531 A | 5/1980 | Aginsky | |
| 4,636,217 A | 1/1987 | Ogilvie et al. | |
| 4,653,489 A | 3/1987 | Tronzo | |
| 4,716,839 A | 1/1988 | Catena | |
| 4,733,665 A | 3/1988 | Palmaz | |
| 4,759,769 A | 7/1988 | Hedman et al. | |
| 4,763,644 A | 8/1988 | Webb | |
| 4,863,476 A * | 9/1989 | Shepperd | 623/17.15 |
| 4,886,062 A | 12/1989 | Wiktor | |
| 4,911,718 A | 3/1990 | Lee et al. | |
| 4,932,975 A | 6/1990 | Main et al. | |
| 4,969,888 A | 11/1990 | Scholten et al. | |
| 4,978,341 A | 12/1990 | Niederhauser | |
| 5,007,909 A | 4/1991 | Rogozinski | |
| 5,015,247 A | 5/1991 | Michelson | |
| 5,026,373 A | 6/1991 | Ray et al. | |
| 5,059,193 A | 10/1991 | Kuslich | |
| 5,108,404 A | 4/1992 | Scholten et al. | |
| 5,123,926 A | 6/1992 | Pisharodi | |
| 5,139,480 A | 8/1992 | Hickle et al. | |
| 5,171,278 A | 12/1992 | Pisharodi | |

(Continued)

FOREIGN PATENT DOCUMENTS

| EP | 0734702 | 10/1996 |
|---|---|---|
| EP | 0758541 | 2/1997 |

(Continued)

OTHER PUBLICATIONS

Franklin, I.J. et al., "Uptake of Tetracycline by Aortic Aneurysm Wall and Its Effect on Inflammation and Proteolysis," *Brit. J. Surger*, 86(6):771-775, 1999.

(Continued)

*Primary Examiner* — Pedro Philogene
*Assistant Examiner* — Lynnsy Schneider
(74) *Attorney, Agent, or Firm* — Levine Bagade Han LLP

(57) ABSTRACT

An implantable orthopedic stability device is disclosed. The device can have a contracted and an expanded configuration. A method of using the device between adjacent vertebral body surfaces surfaces for support and/or fixation of either or both of the adjacent vertebrae is also disclosed.

16 Claims, 45 Drawing Sheets

(56) References Cited

U.S. PATENT DOCUMENTS

| | | | |
|---|---|---|---|
| 5,217,483 A | 6/1993 | Tower | |
| 5,258,031 A | 11/1993 | Salib et al. | |
| 5,273,533 A | 12/1993 | Bonaldo | |
| 5,342,348 A | 8/1994 | Kaplan | |
| 5,345,927 A | 9/1994 | Bonutti | |
| 5,360,417 A | 11/1994 | Gravener et al. | |
| 5,390,683 A | 2/1995 | Pisharodi | |
| 5,391,153 A | 2/1995 | Haber et al. | |
| 5,391,154 A | 2/1995 | Young | |
| 5,397,364 A | 3/1995 | Kozak et al. | |
| 5,425,773 A | 6/1995 | Boyd et al. | |
| 5,458,643 A | 10/1995 | Oka et al. | |
| 5,480,442 A | 1/1996 | Bertagnoli | |
| 5,484,384 A | 1/1996 | Fearnot | |
| 5,496,365 A | 3/1996 | Sgro | |
| 5,522,899 A * | 6/1996 | Michelson | 606/279 |
| 5,534,002 A | 7/1996 | Brumfield et al. | |
| 5,540,690 A | 7/1996 | Miller et al. | |
| 5,549,679 A | 8/1996 | Kuslich | |
| 5,554,191 A | 9/1996 | Lahille et al. | |
| 5,556,413 A | 9/1996 | Lam | |
| 5,562,736 A | 10/1996 | Ray et al. | |
| 5,562,738 A | 10/1996 | Boyd et al. | |
| 5,571,189 A | 11/1996 | Kuslich | |
| 5,571,192 A | 11/1996 | Schonhoffer | |
| 5,591,197 A | 1/1997 | Orth et al. | |
| 5,593,409 A | 1/1997 | Michelson | |
| 5,609,356 A | 3/1997 | Mossi | |
| 5,609,635 A | 3/1997 | Michelson | |
| 5,634,937 A | 6/1997 | Mollenauer et al. | |
| 5,643,312 A | 7/1997 | Fischell et al. | |
| 5,653,763 A | 8/1997 | Errico et al. | |
| 5,658,335 A * | 8/1997 | Allen | 623/17.16 |
| 5,662,615 A | 9/1997 | Blake, III | |
| 5,665,122 A * | 9/1997 | Kambin | 623/17.16 |
| 5,669,909 A | 9/1997 | Zdeblick et al. | |
| 5,674,295 A | 10/1997 | Ray et al. | |
| 5,683,394 A | 11/1997 | Rinner | |
| 5,693,100 A | 12/1997 | Pisharodi | |
| 5,702,449 A | 12/1997 | McKay | |
| 5,702,453 A | 12/1997 | Rabbe et al. | |
| 5,741,253 A | 4/1998 | Michelson | |
| 5,749,916 A | 5/1998 | Richelsoph | |
| 5,772,661 A | 6/1998 | Michelson | |
| 5,776,181 A | 7/1998 | Lee et al. | |
| 5,776,197 A | 7/1998 | Rabbe et al. | |
| 5,776,198 A | 7/1998 | Rabbe et al. | |
| 5,776,199 A | 7/1998 | Michelson | |
| 5,782,832 A | 7/1998 | Larsen et al. | |
| 5,782,903 A | 7/1998 | Wiktor | |
| 5,785,710 A | 7/1998 | Michelson | |
| 5,800,520 A | 9/1998 | Fogarty et al. | |
| 5,824,054 A | 10/1998 | Khosravi et al. | |
| 5,824,093 A | 10/1998 | Ray et al. | |
| 5,827,289 A | 10/1998 | Reiley et al. | |
| 5,827,321 A | 10/1998 | Roubin et al. | |
| 5,853,419 A | 12/1998 | Imran | |
| 5,861,025 A | 1/1999 | Boudghene et al. | |
| 5,863,284 A | 1/1999 | Klein | |
| 5,865,848 A | 2/1999 | Baker | |
| 5,895,387 A | 4/1999 | Guerrero et al. | |
| 5,916,198 A | 6/1999 | Dillow | |
| 5,972,015 A | 10/1999 | Scribner et al. | |
| 5,980,522 A | 11/1999 | Koros et al. | |
| 5,980,550 A | 11/1999 | Eder et al. | |
| 5,984,957 A | 11/1999 | Laptewicz et al. | |
| 6,001,130 A | 12/1999 | Bryan et al. | |
| 6,019,792 A | 2/2000 | Cauthen | |
| 6,022,376 A | 2/2000 | Assell et al. | |
| 6,025,104 A | 2/2000 | Fuller et al. | |
| 6,027,527 A | 2/2000 | Asano et al. | |
| 6,036,719 A | 3/2000 | Meilus | |
| 6,039,761 A | 3/2000 | Li et al. | |
| 6,045,579 A | 4/2000 | Hochshuler et al. | |
| 6,066,154 A | 5/2000 | Reiley et al. | |
| 6,077,246 A | 6/2000 | Kullas et al. | |
| 6,080,193 A | 6/2000 | Hochshuler et al. | |
| 6,083,522 A | 7/2000 | Chu et al. | |
| 6,086,610 A | 7/2000 | Duerig et al. | |
| 6,090,143 A | 7/2000 | Meriwether et al. | |
| 6,102,950 A | 8/2000 | Vaccaro | |
| 6,113,639 A | 9/2000 | Ray et al. | |
| 6,126,689 A | 10/2000 | Brett | |
| 6,127,597 A | 10/2000 | Beyar et al. | |
| 6,129,763 A | 10/2000 | Chauvin et al. | |
| 6,132,465 A | 10/2000 | Ray et al. | |
| 6,140,452 A | 10/2000 | Felt et al. | |
| 6,146,417 A | 11/2000 | Ischinger | |
| 6,159,244 A | 12/2000 | Suddaby | |
| 6,159,245 A | 12/2000 | Meriwether et al. | |
| 6,168,616 B1 | 1/2001 | Brown, III | |
| 6,171,312 B1 | 1/2001 | Beaty | |
| 6,176,882 B1 | 1/2001 | Biedermann et al. | |
| 6,179,874 B1 | 1/2001 | Cauthen | |
| 6,183,506 B1 | 2/2001 | Penn et al. | |
| 6,183,517 B1 | 2/2001 | Suddaby | |
| 6,193,757 B1 | 2/2001 | Foley et al. | |
| 6,206,910 B1 | 3/2001 | Berry et al. | |
| 6,206,924 B1 | 3/2001 | Timm | |
| 6,217,579 B1 * | 4/2001 | Koros | 623/17.11 |
| 6,224,595 B1 | 5/2001 | Michelson | |
| 6,224,603 B1 | 5/2001 | Marino | |
| 6,224,604 B1 | 5/2001 | Suddaby | |
| 6,224,607 B1 | 5/2001 | Michelson | |
| 6,228,060 B1 | 5/2001 | Howell | |
| 6,245,101 B1 | 6/2001 | Drasler et al. | |
| 6,245,107 B1 | 6/2001 | Ferree | |
| 6,280,456 B1 | 8/2001 | Scribner et al. | |
| 6,287,332 B1 | 9/2001 | Bolz et al. | |
| 6,293,967 B1 | 9/2001 | Shanley | |
| 6,302,914 B1 | 10/2001 | Michelson | |
| 6,332,895 B1 | 12/2001 | Suddaby | |
| 6,371,989 B1 | 4/2002 | Chauvin et al. | |
| 6,395,031 B1 | 5/2002 | Foley et al. | |
| 6,402,750 B1 | 6/2002 | Atkinson et al. | |
| 6,402,785 B1 | 6/2002 | Zdeblick et al. | |
| 6,409,765 B1 | 6/2002 | Bianchi et al. | |
| 6,419,704 B1 | 7/2002 | Ferree | |
| 6,419,705 B1 | 7/2002 | Erickson | |
| 6,423,083 B2 | 7/2002 | Reiley et al. | |
| 6,425,916 B1 | 7/2002 | Garrison et al. | |
| 6,425,919 B1 | 7/2002 | Lambrecht | |
| 6,428,569 B1 | 8/2002 | Brown | |
| 6,432,107 B1 | 8/2002 | Ferree | |
| 6,436,098 B1 | 8/2002 | Michelson | |
| 6,436,140 B1 | 8/2002 | Liu et al. | |
| 6,440,168 B1 | 8/2002 | Cauthen | |
| 6,447,544 B1 | 9/2002 | Michelson | |
| 6,447,546 B1 | 9/2002 | Bramlet et al. | |
| 6,447,547 B1 | 9/2002 | Michelson | |
| 6,451,025 B1 | 9/2002 | Jervis | |
| 6,454,804 B1 | 9/2002 | Ferree | |
| 6,454,806 B1 * | 9/2002 | Cohen et al. | 623/17.15 |
| 6,468,301 B1 | 10/2002 | Amplatz et al. | |
| 6,468,302 B2 | 10/2002 | Cox et al. | |
| 6,478,823 B1 | 11/2002 | Michelson | |
| 6,482,235 B1 | 11/2002 | Lambrecht et al. | |
| 6,488,710 B2 | 12/2002 | Besselink | |
| 6,491,724 B1 | 12/2002 | Ferree | |
| 6,494,883 B1 | 12/2002 | Ferree | |
| 6,508,839 B1 | 1/2003 | Lambrecht et al. | |
| 6,514,255 B1 | 2/2003 | Ferree | |
| 6,520,991 B2 | 2/2003 | Huene | |
| 6,533,817 B1 | 3/2003 | Norton et al. | |
| 6,554,833 B2 | 4/2003 | Levy et al. | |
| 6,562,074 B2 * | 5/2003 | Gerbec et al. | 623/17.15 |
| 6,582,431 B1 | 6/2003 | Ray | |
| 6,582,467 B1 | 6/2003 | Teitelbaum et al. | |
| 6,585,770 B1 | 7/2003 | White et al. | |
| 6,592,589 B2 | 7/2003 | Hajianpour | |
| 6,592,625 B2 | 7/2003 | Cauthen | |
| 6,595,998 B2 | 7/2003 | Johnson et al. | |
| 6,602,291 B1 | 8/2003 | Ray et al. | |
| 6,607,544 B1 | 8/2003 | Boucher et al. | |

| Patent | Date | Inventor |
|---|---|---|
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 * | 11/2003 | Wagner et al. ............ 623/17.15 |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm, Jr. et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,923,830 B2 | 8/2005 | Michelson |
| 6,936,070 B1 | 8/2005 | Muhanna |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,212,480 B2 | 5/2007 | Shoji et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,276 B2 | 7/2007 | Argentine et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,431,735 B2 | 10/2008 | Liu et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,722,674 B1 * | 5/2010 | Grotz .......................... 623/17.11 |
| 7,828,849 B2 * | 11/2010 | Lim ........................... 623/17.16 |
| 7,837,734 B2 * | 11/2010 | Zucherman et al. ....... 623/17.15 |
| 7,879,036 B2 | 2/2011 | Biedermann et al. |
| 7,879,082 B2 | 2/2011 | Brown |
| 8,105,382 B2 * | 1/2012 | Olmos et al. ............... 623/17.15 |
| 8,262,737 B2 * | 9/2012 | Bagga et al. ............... 623/17.16 |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 * | 7/2003 | Michelson ................. 623/17.16 |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | McGuckin |
| 2003/0199981 A1 | 10/2003 | Ferree |
| 2003/0204260 A1 | 10/2003 | Ferree |

| | | |
|---|---|---|
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233188 A1 | 12/2003 | Jones |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | McKay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0097927 A1 | 5/2004 | Yeung et al. |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153146 A1 | 8/2004 | Lashinski et al. |
| 2004/0167625 A1 | 8/2004 | Beyar et al. |
| 2005/0010292 A1 | 1/2005 | Carrasco |
| 2005/0015152 A1 | 1/2005 | Sweeney |
| 2005/0033431 A1 | 2/2005 | Gordon et al. |
| 2005/0033437 A1* | 2/2005 | Bao et al. ................ 623/17.15 |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0228391 A1 | 10/2005 | Levy et al. |
| 2005/0240188 A1 | 10/2005 | Chow et al. |
| 2005/0249776 A1 | 11/2005 | Chen et al. |
| 2005/0261768 A1 | 11/2005 | Trieu |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0085069 A1 | 4/2006 | Kim |
| 2006/0089715 A1 | 4/2006 | Truckai et al. |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1* | 6/2006 | Ensign ................ 623/17.16 |
| 2006/0142859 A1 | 6/2006 | McLuen |
| 2006/0149349 A1 | 7/2006 | Garbe |
| 2006/0149385 A1 | 7/2006 | McKay |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0200166 A1 | 9/2006 | Hanson et al. |
| 2006/0206207 A1 | 9/2006 | Dryer et al. |
| 2006/0241764 A1* | 10/2006 | Michelson ................ 623/17.11 |
| 2006/0253201 A1 | 11/2006 | McLuen |
| 2006/0264968 A1 | 11/2006 | Frey et al. |
| 2006/0271061 A1 | 11/2006 | Beyar et al. |
| 2006/0276899 A1* | 12/2006 | Zipnick et al. ............ 623/17.13 |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 | 7/2007 | Kim et al. |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0233260 A1 | 10/2007 | Cragg |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0140207 A1* | 6/2008 | Olmos et al. ................ 623/17.16 |
| 2008/0147193 A1* | 6/2008 | Matthis et al. ............ 623/17.16 |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0221687 A1 | 9/2008 | Viker |
| 2008/0243254 A1 | 10/2008 | Butler |
| 2008/0249625 A1 | 10/2008 | Waugh et al. |
| 2008/0294205 A1 | 11/2008 | Greenhalgh et al. |
| 2009/0018524 A1 | 1/2009 | Greenhalgh et al. |
| 2009/0024204 A1 | 1/2009 | Greenhalgh et al. |
| 2009/0024247 A1* | 1/2009 | Levy et al. ................ 623/17.16 |
| 2009/0149956 A1 | 6/2009 | Greenhalgh et al. |
| 2009/0163918 A1 | 6/2009 | Levy et al. |
| 2009/0182431 A1 | 7/2009 | Butler et al. |
| 2009/0198338 A1 | 8/2009 | Phan |
| 2009/0234398 A1 | 9/2009 | Chirico et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0262147 A1 | 10/2010 | Siegal et al. |
| 2010/0292796 A1* | 11/2010 | Greenhalgh et al. ........ 623/17.11 |
| 2011/0054621 A1* | 3/2011 | Lim ................ 623/17.16 |

FOREIGN PATENT DOCUMENTS

| | | |
|---|---|---|
| EP | 1804733 | 7/2007 |
| FR | 2874814 | 11/2007 |
| JP | 2000-210315 | 8/2000 |
| JP | 2002-535080 | 10/2002 |
| JP | 2003-512887 | 4/2003 |
| JP | 2004-511297 | 4/2004 |
| JP | 2004-531355 | 10/2004 |
| JP | 2004-321348 | 11/2004 |
| WO | WO 88/03781 | 6/1988 |
| WO | WO 92/14423 | 9/1992 |
| WO | WO 95/31945 | 11/1995 |
| WO | WO 96/03092 | 2/1996 |
| WO | WO 97/00054 | 1/1997 |
| WO | WO 00/30523 | 6/2000 |
| WO | WO 00/44319 | 8/2000 |
| WO | WO 00/44321 | 8/2000 |
| WO | WO 01/32099 | 5/2001 |
| WO | WO 01/78625 | 10/2001 |
| WO | WO 01/95838 | 12/2001 |
| WO | WO 02/13700 | 2/2002 |
| WO | WO 02/32347 | 4/2002 |
| WO | WO 03/003943 | 1/2003 |
| WO | WO 03/003951 | 1/2003 |
| WO | WO 2005/062900 | 7/2005 |
| WO | WO 2005/096975 | 10/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/050500 | 5/2006 |
| WO | WO 2006/060420 | 6/2006 |
| WO | WO 2006/076712 | 7/2006 |
| WO | WO 2006/086241 | 8/2006 |
| WO | WO 2006/096167 | 9/2006 |
| WO | WO 2006/132945 | 12/2006 |
| WO | WO 2007/009107 | 1/2007 |
| WO | WO 2007/016368 | 2/2007 |
| WO | WO 2007/038611 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/075411 | 7/2007 |
| WO | WO 2007/079021 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/070863 | 6/2008 |
| WO | WO 2009/114381 | 9/2009 |
| WO | WO 2012/027490 | 3/2012 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and *Chlamydia pneumoniae*," *Brit., J. Surgery*, 88(7):935-940, Feb. 2001.

Walton, L.J. et al., "Inhibition of Prostoglandin E2 Synthesis in Abdominal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

Database WPI, Week 198004, Thomson Scientific, London, GB; AN 1980-A8866C, XP002690114, -& SU 662 082 A1 (Tartus Univ) May 15, 1979, abstract, figures 1,2.

\* cited by examiner

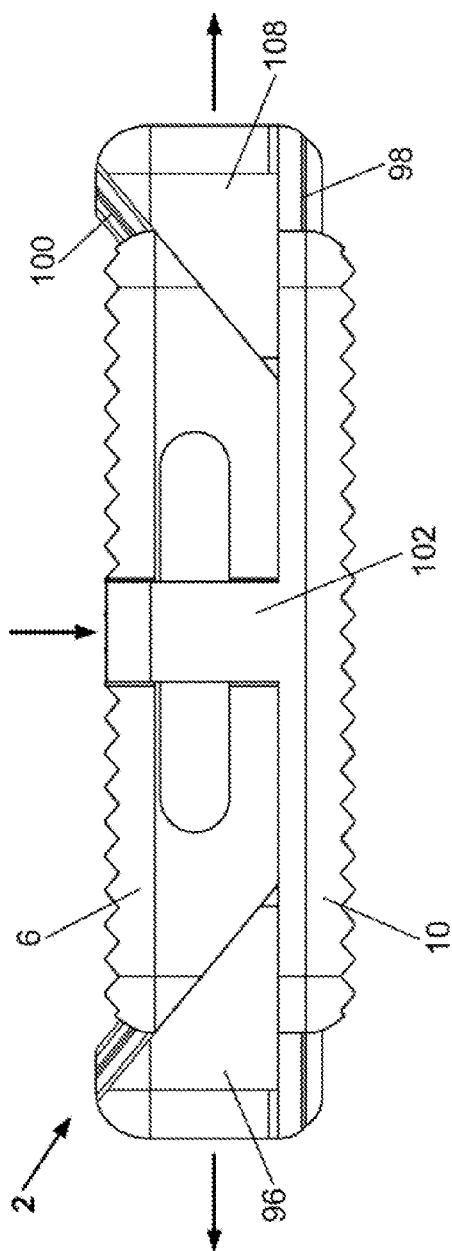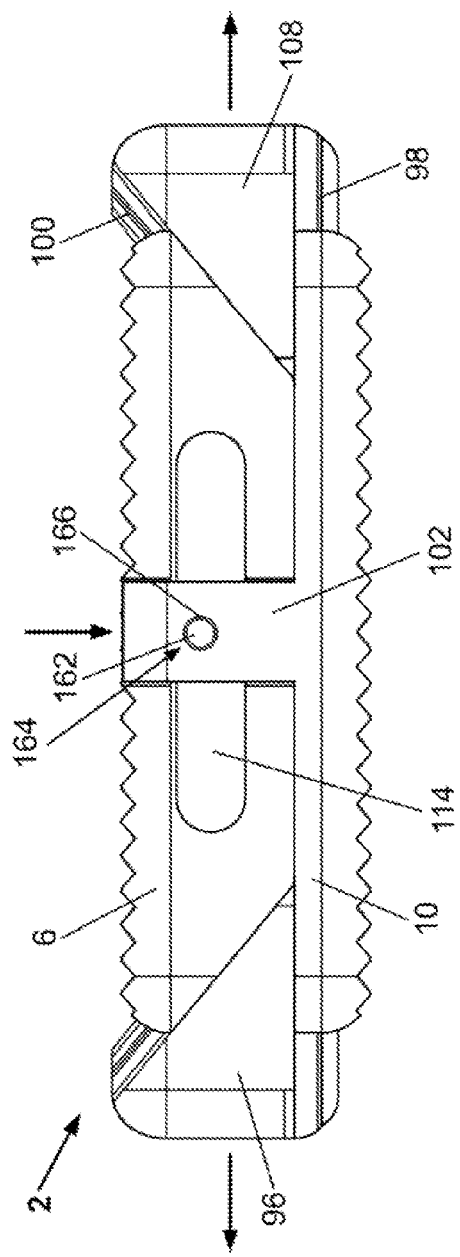

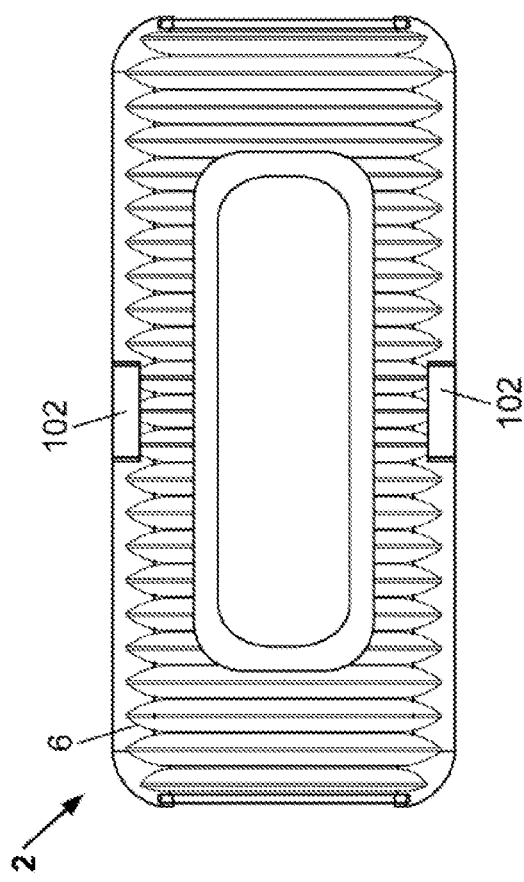
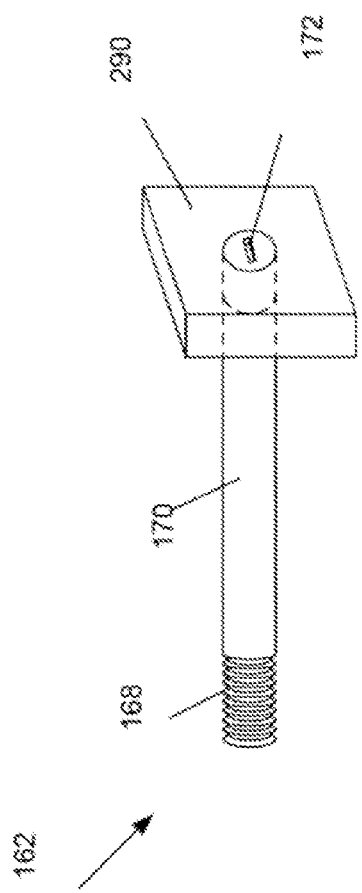

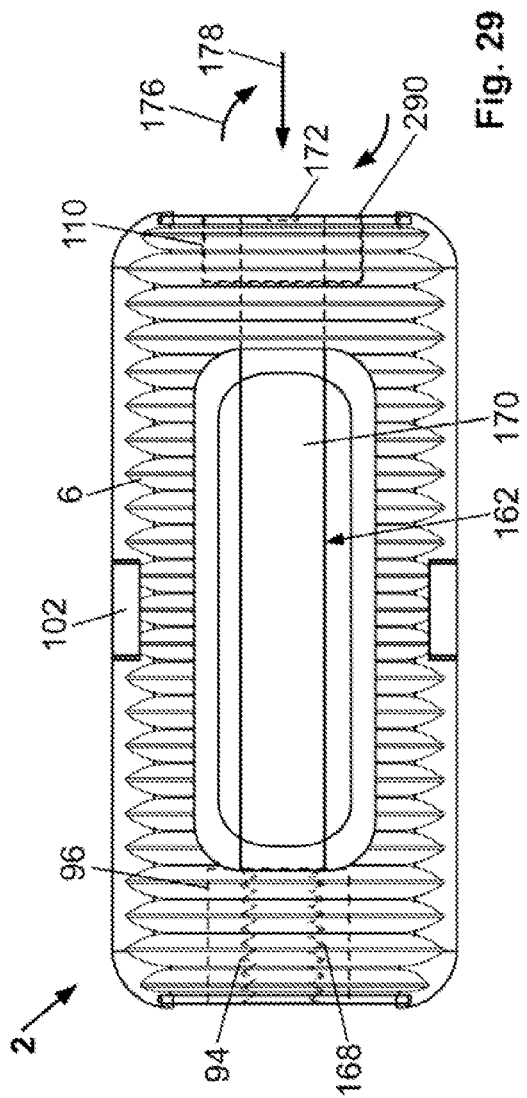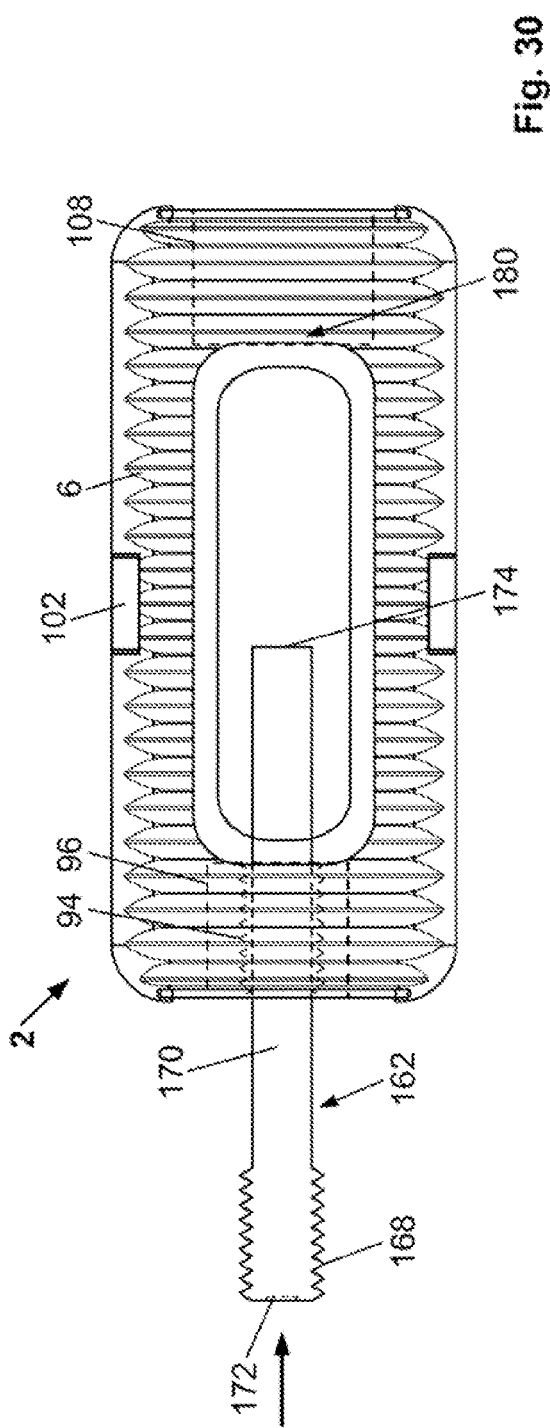

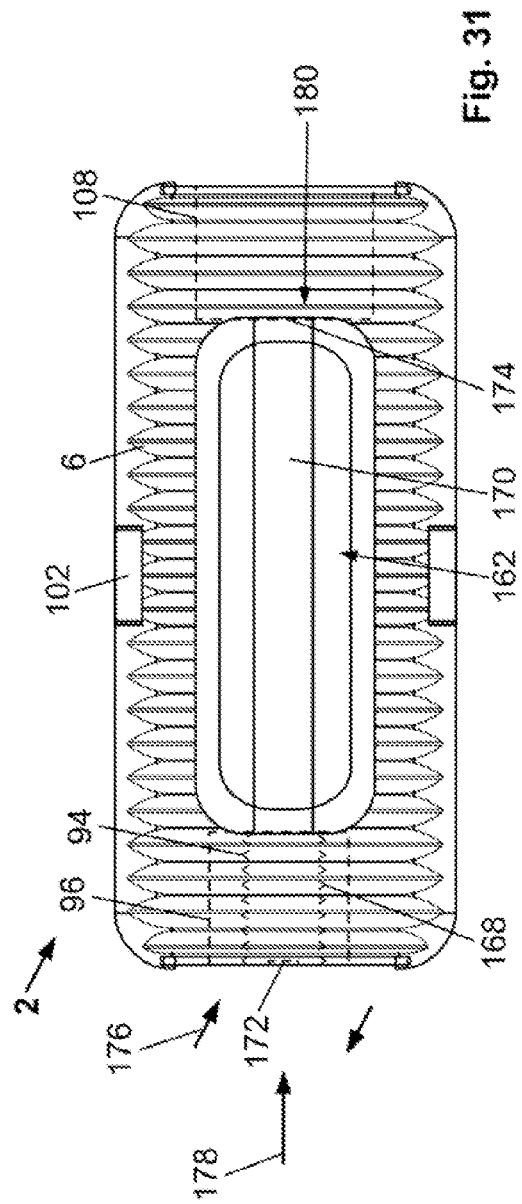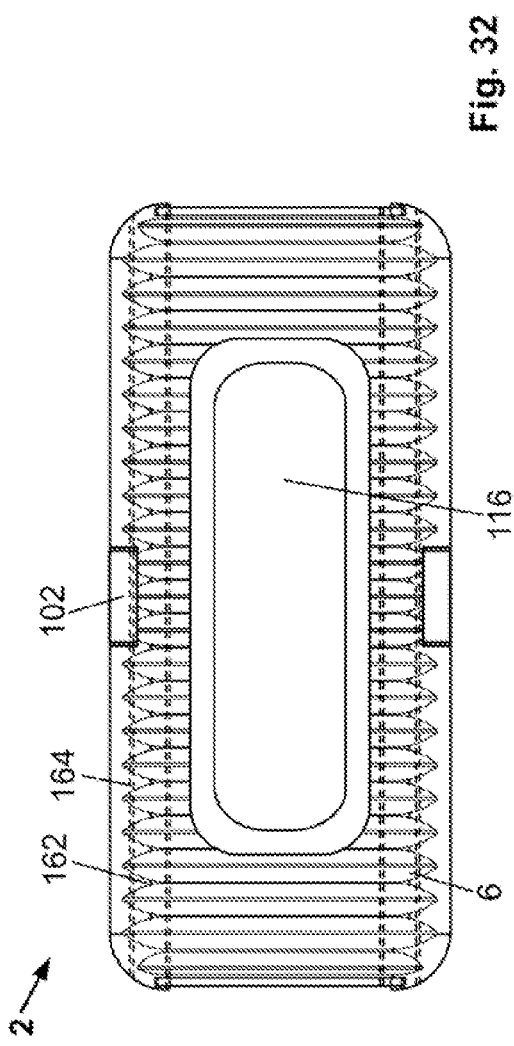

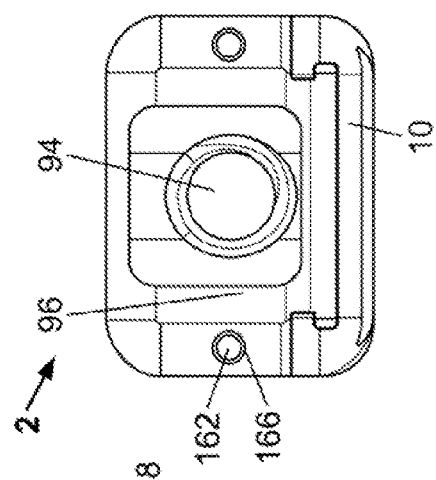
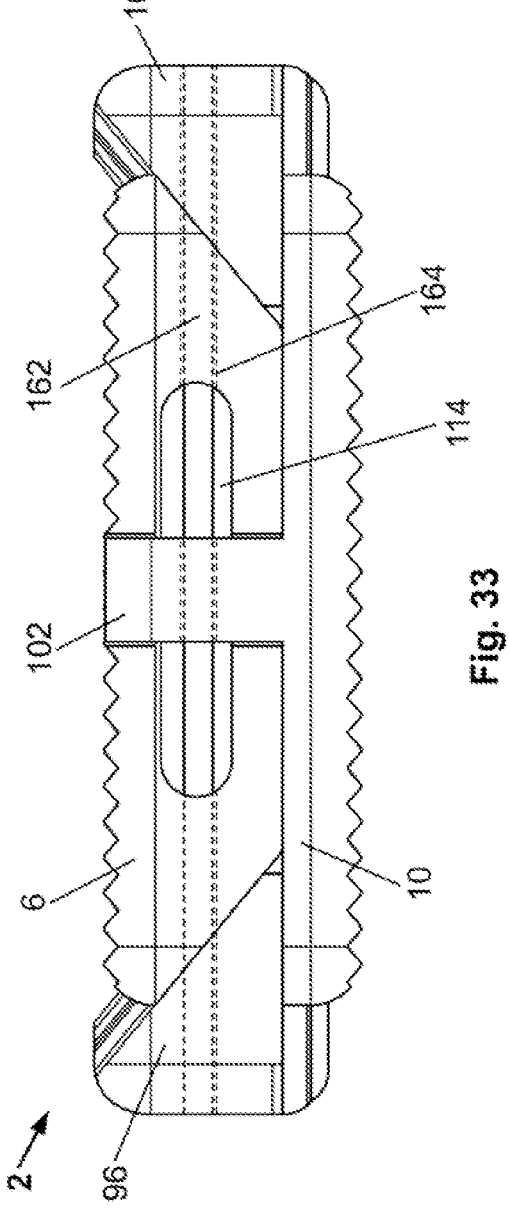

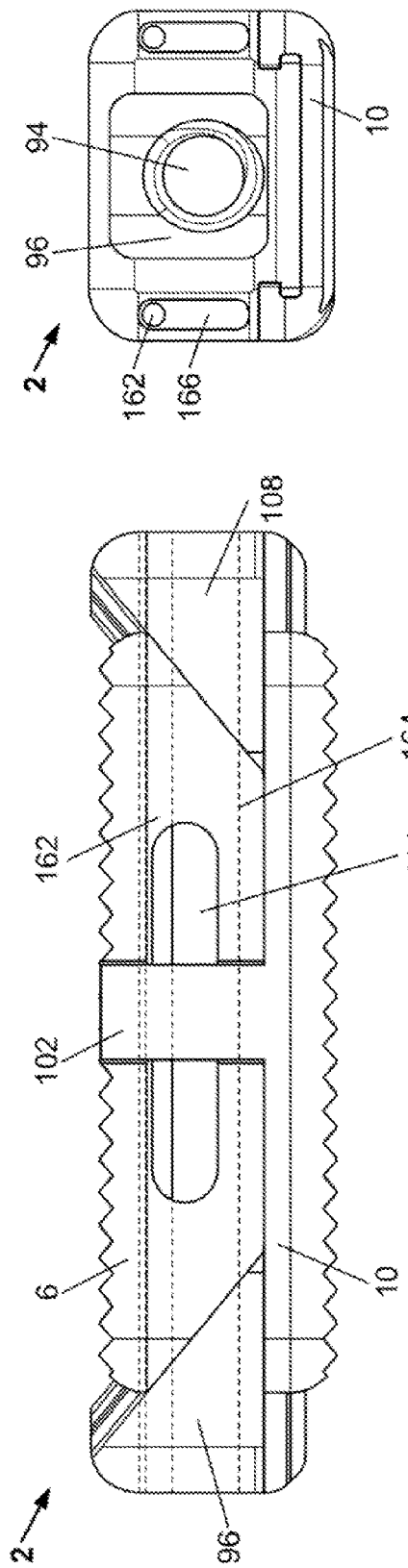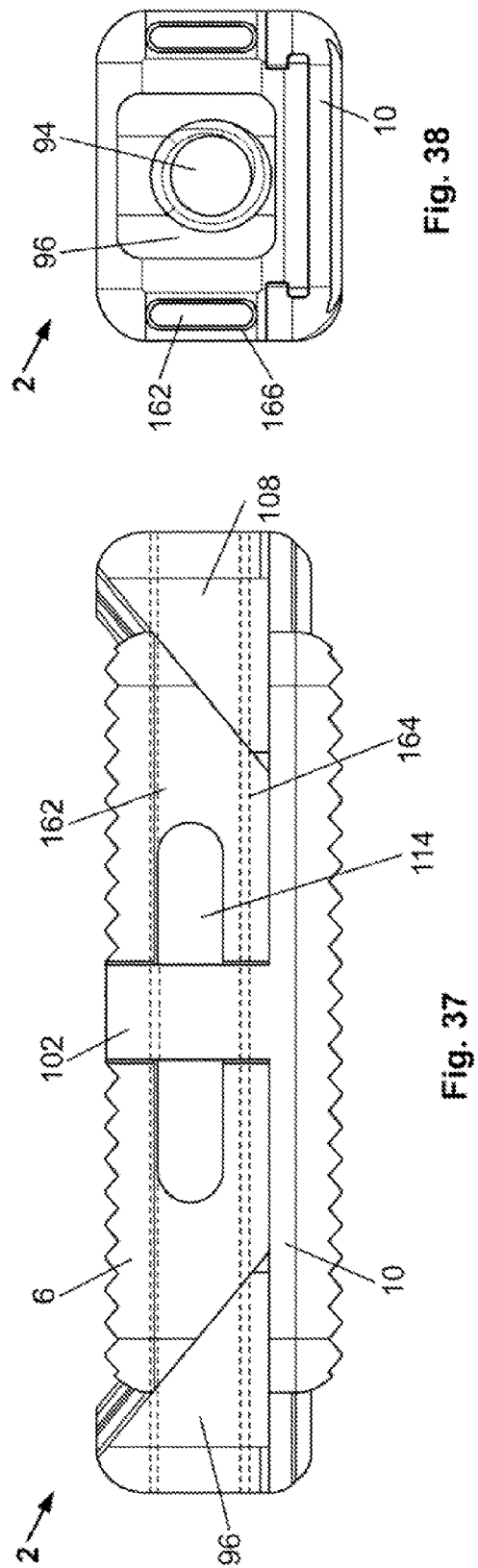

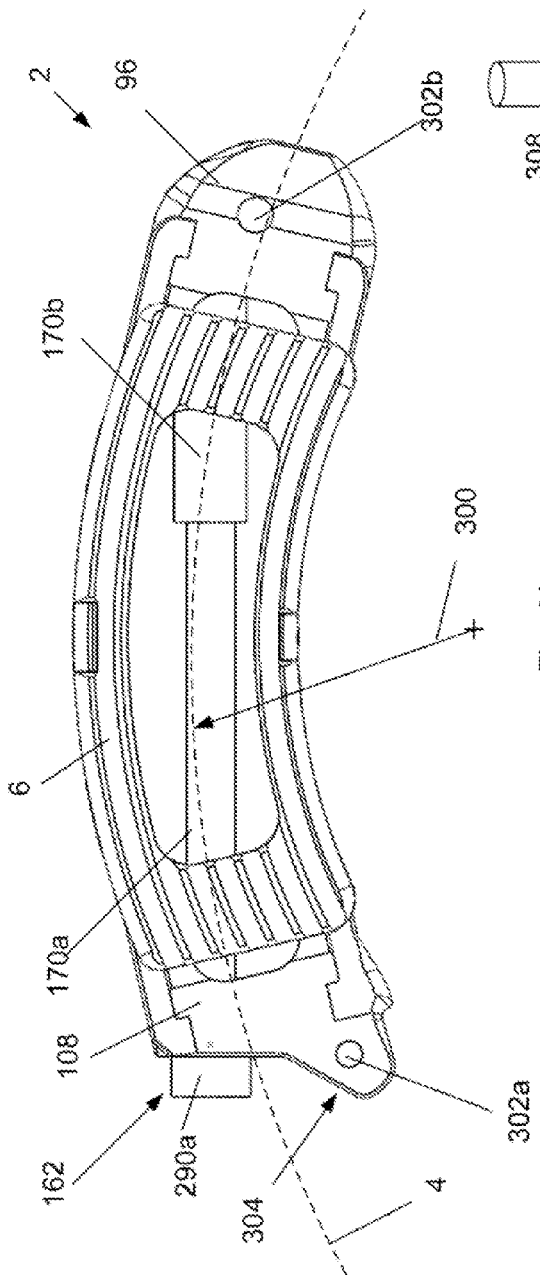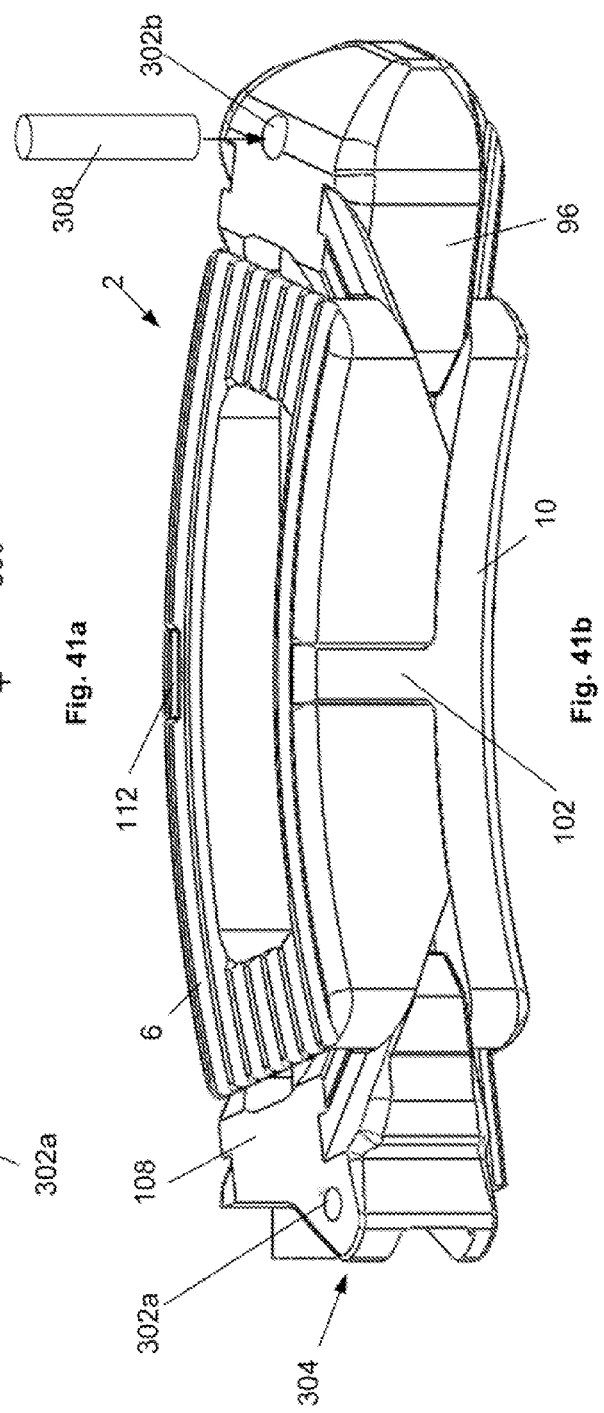

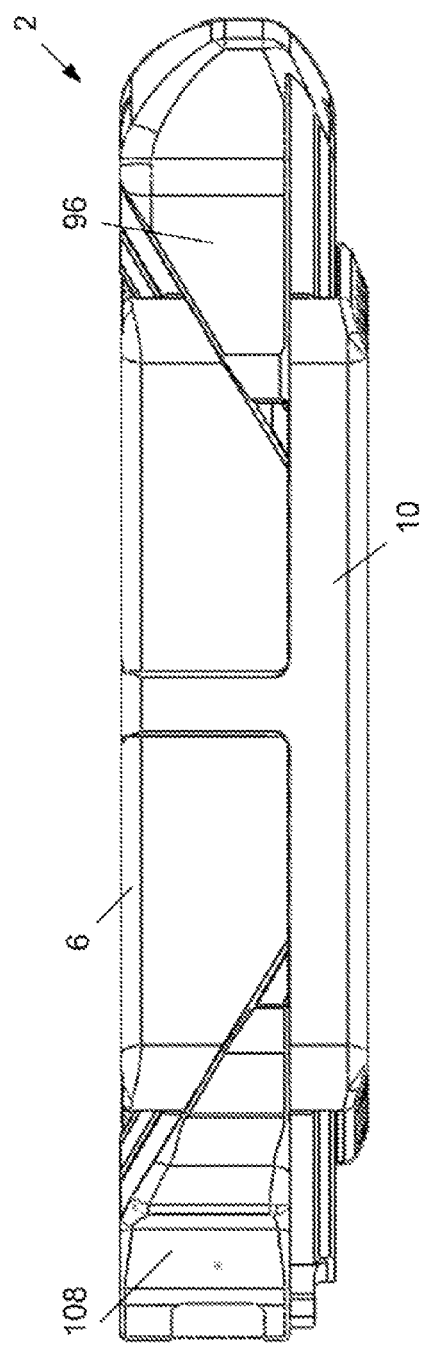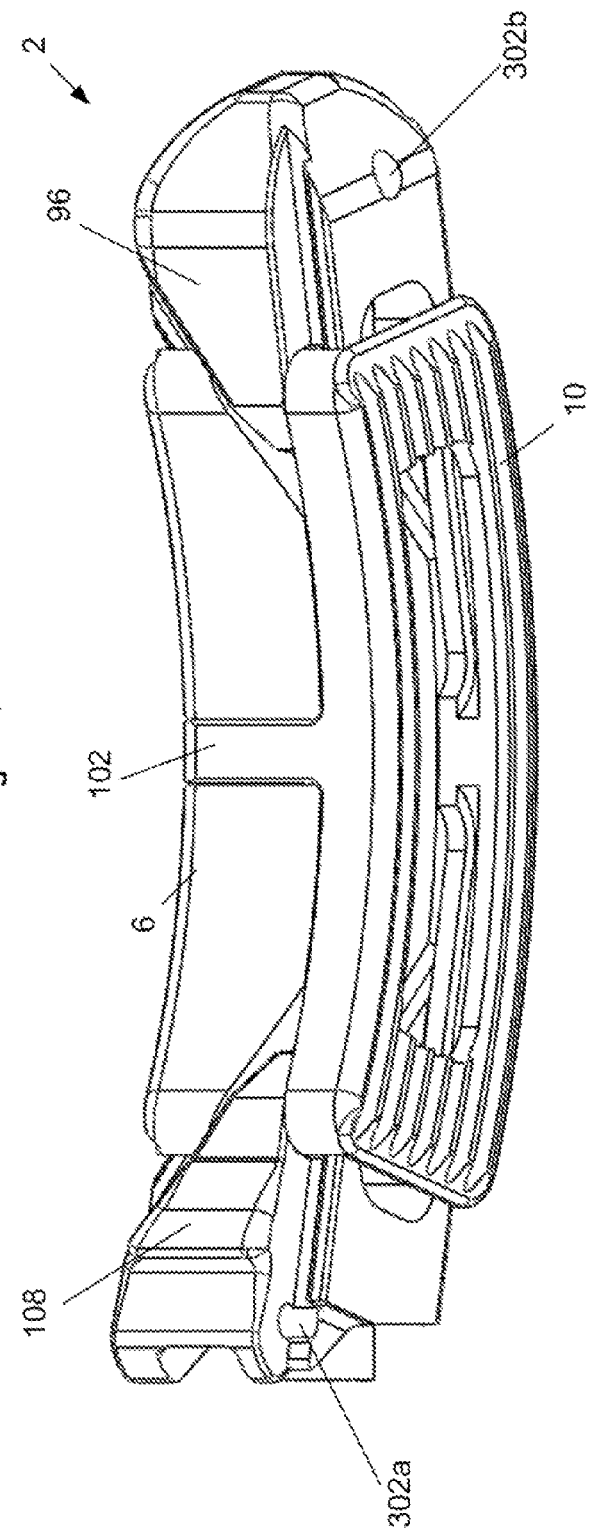

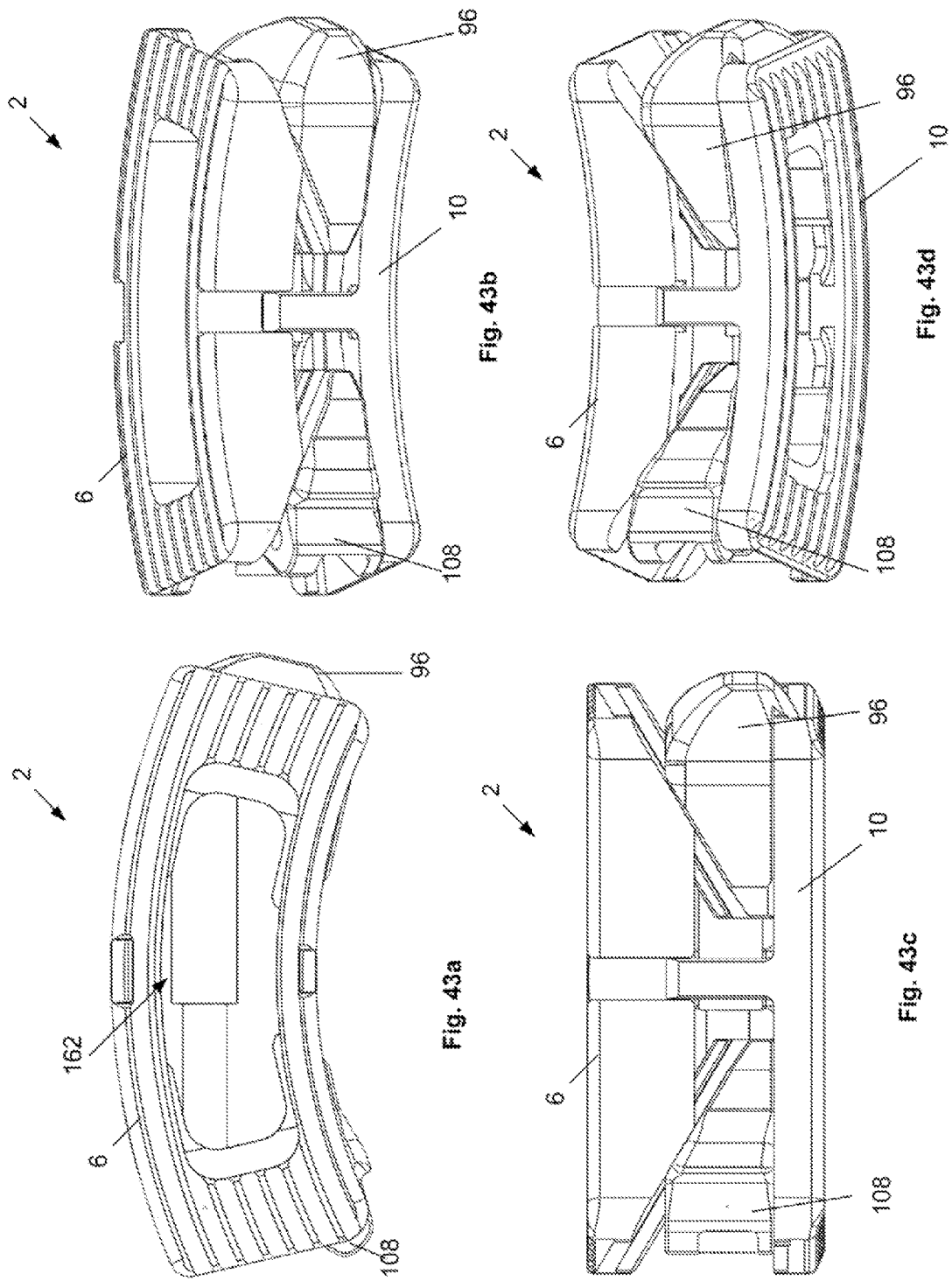

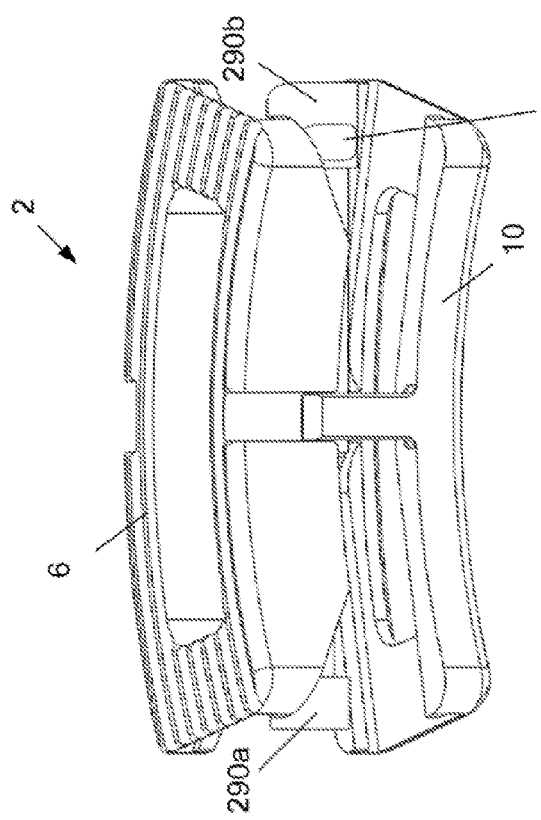
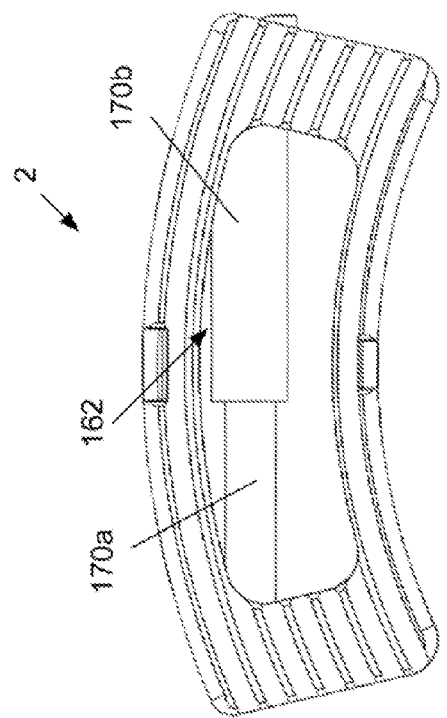
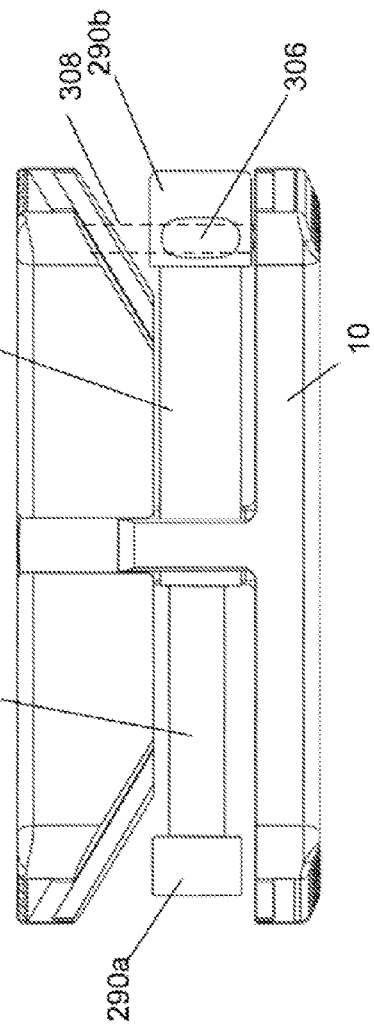

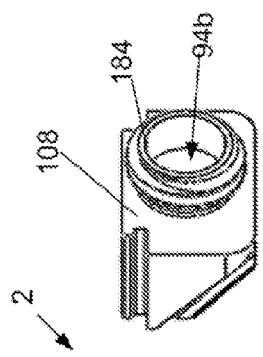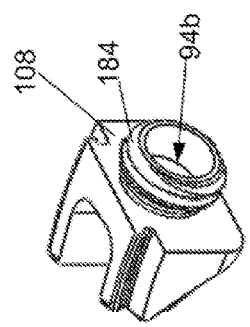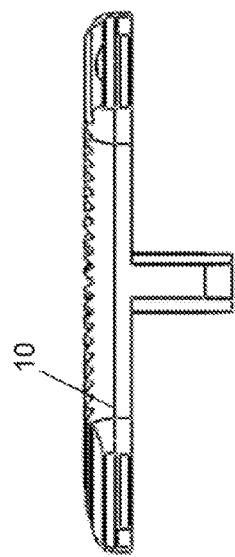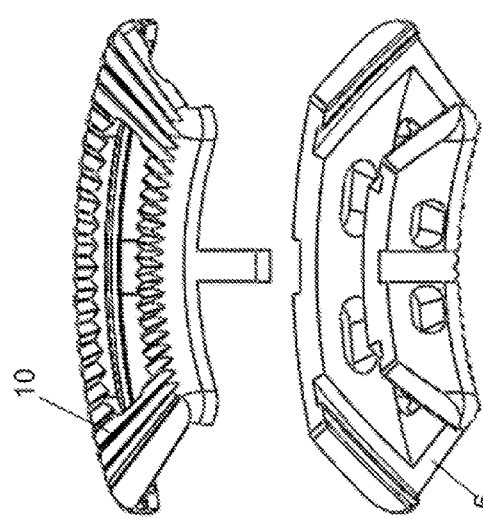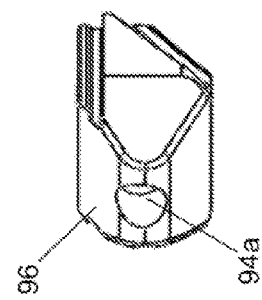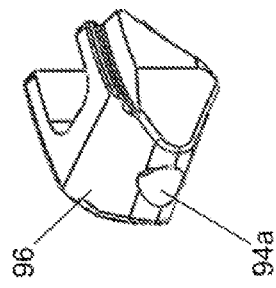
Fig. 53c
Fig. 53d

FIXATION DEVICE AND METHOD

BACKGROUND OF THE INVENTION

1. Technical Field

Devices and methods for fixation of tissue are disclosed. More specifically, the devices and methods can be for inter body vertebral fusion of vertebrae or fusion of other bones to one another.

2. Background of the Art

A vertebroplasty device and method that eliminates or reduces the risks and complexity of the existing art is desired. A vertebroplasty device and method that may reduce or eliminate the need to inject a liquid directly into the compression fracture zone is also desired.

Other ailments of the spine result in degeneration of the spinal disc in the intervertebral space between the vertebral bodies. These include degenerative disc disease and traumatic injuries. In either case, disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, adjacent vertebra can be fixated or fused to each other using devices or bone grafts. These may include, for example, screw and rod systems, interbody spacers (e.g., PEEK spacers or allograft bone grafts) threaded fusion cages and the like.

Some fixation or fusion devices are attached to the vertebra from the posterior side. The device will protrude and result in additional length (i.e., needed to overlap the vertebrae) and additional hardware to separately attach to each vertebrae. Fusion cages and allografts are contained within the intervertebral space, but must be inserted into the intervertebral space in the same dimensions as desired to occupy the intervertebral space. This requires that an opening sufficient to allow the cage or graft must be created through surrounding tissue to permit the cage or graft to be inserted into the intervertebral space.

A spinal fixation or fusion device that can be implanted with or without the need for additional hardware is desired. Also desired is a fixation or fusion device that can be deployed in a configuration where overlapping the fixated or fused vertebrae is not required.

Also desired is an intervertebral device the may be inserted in to the intervertebral space at a first smaller dimension and deployed to a second, larger dimension to occupy the intervertebral space. The ability to insert an intervertebral spacer at a dimension smaller than the deployed dimension would permit less disruption of soft and boney tissue in order to access the intervertebral space.

SUMMARY OF THE INVENTION

A device that can replace or supplement the screw or rod elements of a typical fusion system is disclosed. The device can be placed in the inter-vertebral space to fuse adjacent vertebrae and/or create a bone mass within the inter-vertebral space in a patient's spine.

The device can be less invasive than typical existing devices. For example, the device can be in a compacted (i.e., small) configuration when inserted into a patient and transformed into an expanded (i.e., large) configuration when positioned at the target site. For example, the device can be expanded when the device is between the inferior and superior vertebral body surfaces. The device can create less soft tissue (e.g., bone) disruption than a typical fusion system. The device in an expanded configuration can improve anchoring within the joint, structural stability, and create an environment for bone healing and growth leading to fusion between adjacent vertebrae.

During deployment into tissue (e.g., bone), one, two or more holes can be drilled into the target site to create a deployment hole in which to insert the device. The deployment hole can be round or non-round (e.g., by drilling more than one overlapping or adjacent hole, or crafting a square or rectangular hole), for example to substantially match the transverse cross-section of the device in a contracted configuration.

The device can be cannulated, for example having a lateral (i.e., transverse or latitudinal) and/or lengthwise (i.e., longitudinal) channel through the device. The device can be deployed over a wire or leader, such as a guidewire. The device can be slid over the guidewire, with the guidewire passing through the longitudinal channel of the device.

BRIEF DESCRIPTION OF THE DRAWINGS

FIGS. 17, 18, 20 and 21 are perspective, side, end and top views, respectively, of the variation of the device of FIG. 1 in a pre-deployment configuration.

FIGS. 19 and 22 are side and top views, respectively, of a variation of the device of FIG. 1 in a pre-deployment configuration.

FIGS. 24 and 25 are perspective and top views, respectively, of the variation of the device of FIG. 1 in a deployed configuration. FIG. 22 is illustrated with the top and the base in see-through views for illustrative purposes.

FIGS. 26 and 27 illustrate variations of the locking pin.

FIGS. 28 and 29 illustrate a variation of a method for using the variation of the locking pin of FIG. 26.

FIGS. 30 and 31 illustrate a variation of a method for using the variation of the locking pin of FIG. 27.

FIGS. 32, 33 and 34 are top, side and end views, respectively, of a variation of the device with the locking pin.

FIGS. 35 and 36 are side and end views, respectively, of a variation of the device with the locking pin.

FIGS. 37 and 38 are side and end views, respectively, of a variation of the device with the locking pin.

FIGS. 41a through 41d are top, top perspective, side, and bottom perspective views, respectively, of a variation of the device in a longitudinally expanded and radially contracted configuration.

FIGS. 43a through 43d are top, top perspective, side, and bottom perspective views, respectively, of the device of FIGS. 41a through 41d in a longitudinally contracted and radially (e.g., height) expanded configuration.

FIGS. 44a through 44c are top, side and top perspective views, respectively, of the variation of the device of FIGS. 43a through 43d with the side ramps not shown for illustrative purposes.

FIGS. 53a through 53d are top, top perspective, side, and bottom perspective exploded views, respectively, of the variation of the device of FIGS. 48a through 48d.

FIGS. 53c and 53d illustrate the device upside down compared to the orientation shown in FIGS. 53a and 53b.

DETAILED DESCRIPTION

A device 2 is disclosed that can be inserted into a target site 264 with the device 2 in a compressed or contracted (i.e., small) configuration. Once positioned in the deployment site, the device 2 can be transformed into an expanded (i.e., larger, bigger) configuration. The device 2 can be inserted and expanded in orthopedic target sites 264 for fixation and/or support. For example, the device 2 can be inserted and expanded over a guidewire between adjacent vertebral bodies.

Figure 1:
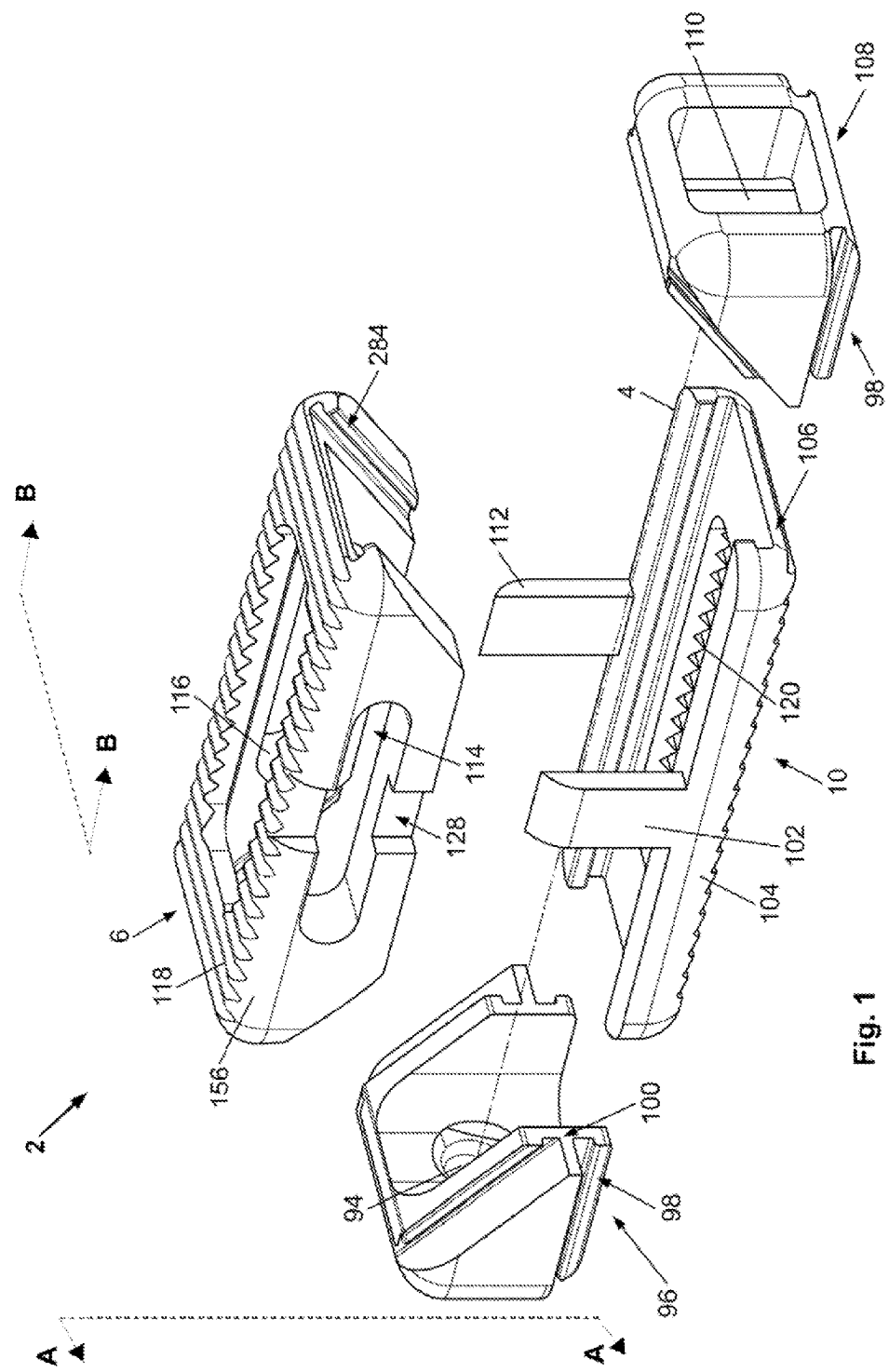
FIG. 1 is an exploded view of a variation of the expandable support device.

FIG. 1 illustrates that the device 2 can have a first longitudinal end and a second longitudinal end along a longitudinal axis 4. The longitudinal axis 4 can be straight or substantially straight. The device 2 can have a bottom or plate 286 (bottom and base plate are used interchangeably) and a top plate 6. The base 138 or bottom plate 10 and top plate 6 can be or have plates 286, panels, struts 216 (e.g., legs), ports, cells 88, and combinations thereof. The base plate 10 and top plate 6 can be configured to be slidably attachable to the other. For example, the base (or top) plate can have one or more stability bars 102. The top (or base) plate can have one or more stability grooves 128. The stability bars 102 can be configured to be slidably attachable to the stability grooves 128.

The slidable attachment of the top and base plates can permit the base 138 to move radially (with respect to the longitudinal axis 4) relative to the top and vice versa.

The top plate 6 can have a high-friction and/or low-friction texture extending radially away from the base 138. For example, the top plate 6 can have one or numerous rows of top teeth 118. The bottom plate 10 can have a high-friction and/or low-friction texture extending radially away from the base plate. For example, the bottom plate 10 can have one or numerous rows of bottom teeth 104. The top teeth 118 and the bottom teeth 104

The top plate 6 can have one or more side ports 114 and/or top ports. The base plate can have one or more base ports 120 and/or side ports 114. The base ports 120, side ports 114, and/or top ports can be ingrowth channels 28. The ports can be circular, square, triangular, oval, elongated in the longitudinal direction, elongated in the radial direction, or combinations thereof.

The top plate 6 can have a top chamfer 156. The base plate can have a base chamfer. The chamfers can be atraumatic edges. The chamfers can extend along the perimeter of the base 138 and/or top.

The device 2 can have one, two or more wedges, for example a first or distal side ramp 96 on a first longitudinal side (e.g., the distal side) of the base plate and a second or proximal side ramp 108 on a second longitudinal side (e.g., the proximal side) of the base plate. The side ramps 96 and 108 can be configured to be slidably attachable to the base plate 10 and/or the top plate 6. The wedges or ramps 96 and 108 can be separate from each other. The ramps 96 and 108 can move independent of each other. The ramps 96 and 108 can be constrained by the top and bottom plates 6 and 10 to move concurrently and at the same rate in opposite directions. The angled faces of the ramps 96 and 108 can face each other. The "pointed" ends of the ramps 96 and 108 can point toward each other.

The ramps 96 and 108 and top plate 6 can be brought within proximity of the base plate 10. The ramps 96 and 108 can be slidably attached to the base plate 10. The ramps 96 and 108 can have ramp second tongues and grooves 98. The base plate 10 can have one or more base tongues and grooves 106. The ramp second tongues and grooves 98 can be configured to slidably attach to the base tongues and grooves 106.

The ramps 96 and 108 can be configured to be slidably attachable to the top plate 6. For example, the ramps 96 and 108 can have ramp first tongues and grooves 100. The top plate 6 can have top tongues and grooves 284. The ramp first tongues and grooves 100 can slidably engage the top tongues and grooves 284.

The first tongues and grooves can be at a ramp angle 136 with respect to the second tongues and grooves. The ramp angle 136 can be from about 15° to about 75°, more narrowly from about 30° to about 60°, for example about 45°.

One or more of the ramps 96 and 108 can have a ramp locking plate port 110. The ramp locking plate ports 110 can each be configured to receive a ramp locking plate. The ramps 96 and 108 can each have ramp ports, such as the threaded ramp ports. The threaded ramp ports can pass through the ramps 96 and 108, for example opening into the ramp locking plate port 110.

Figure 2:
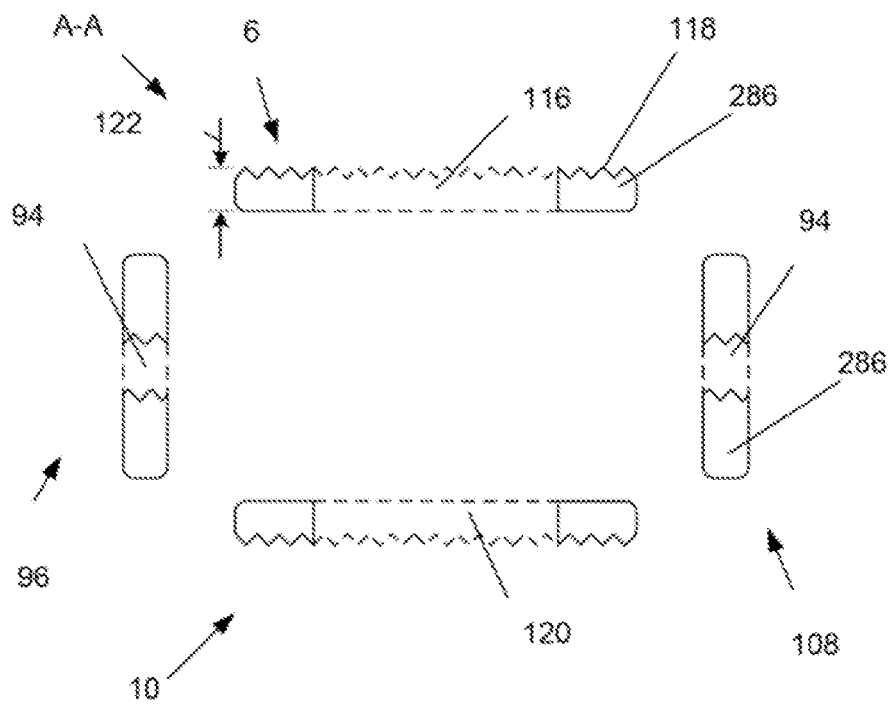
FIGS. 2 through 4 illustrate variations of cross-section A-A of FIG. 1.

FIG. 2 illustrates that each of the top, or base 138 or bottom plates can have a plate thickness 122. The plates 286 can be thinned adjacent to some or all ports. The plate thickness 122 can be substantially constant along the length of the top or base 138. The plate thickness 122 can be non-constant, for example along the length and/or width of the top port or base port 120 and the top teeth 118 or base teeth. Each plate 286 of the first side ramp 96 and the second side ramp 108 can have a substantially constant plate thickness 122 along the height of the plate 286 save for the respective ramp ports.

Figure 3:
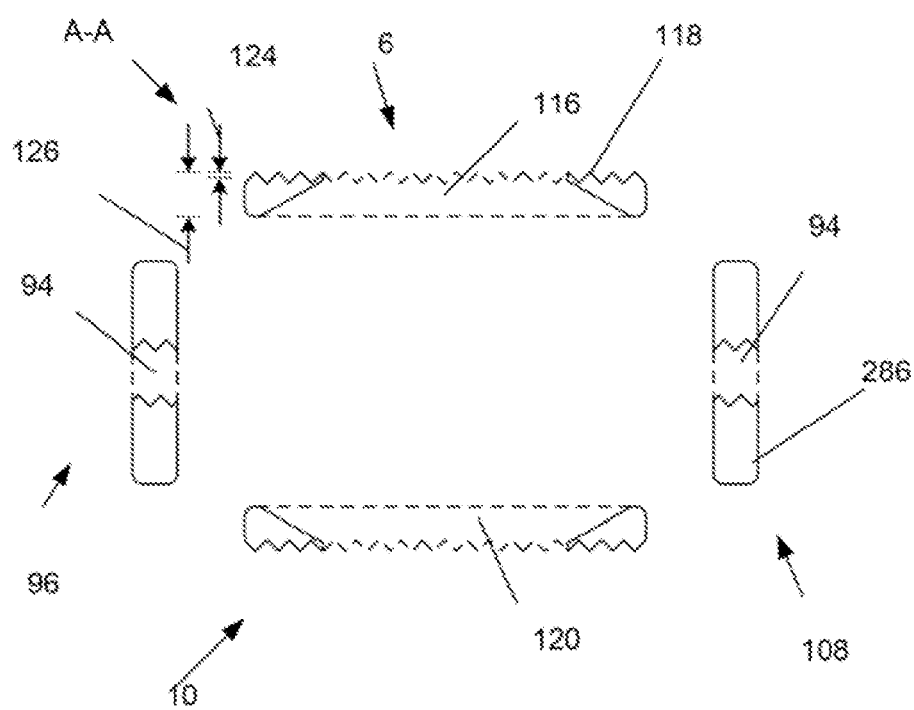

FIG. 3 illustrates that the top and/or bottom plates can thin as the plate 286 nears the port. For example, the plate 286 can have a maximum plate thickness 126 and a minimum plate thickness 124. The maximum plate thickness 126 and minimum plate thickness 124 can be measured with or without accounting for the change in thickness due to the teeth. The minimum plate thickness 124 can be substantially less than the maximum thickness 126. The minimum plate thickness 124 can be substantially 0. The plate 286 can slope outward (as shown), inward, or a combination of both (e.g., sloping inward and outward concurrently to form the rim of the port at a radius from the longitudinal axis between the radii of the outer and inner surfaces of the plate 286).

When the device 2 is in a deployed configuration in vivo, the device 2 can be partially or substantially filled with a liquid, gel, or solid (e.g., in small parts or granules) filler 262 material, or combinations thereof, such as bone morphogenic powder or any other material disclosed herein or combinations thereof. The filler 262 material can contact or be in near contact with the surrounding tissue near the edge of the ports, for example where the plate 286 is thinned. The filler 262 can be inserted into the device 2 before, and/or during (i.e., prepacked), and/or after the device 2 is inserted and/or expanded in the target site.

As the device 2 is expanded and contracted, the volume of the interior channel of the device (i.e., defined between the top and base plates and the opposing ramps) can remain constant. For example, filler can be inserted into the device 2 before the device is radially expanded. The device 2 can be longitudinally contracted and radially expanded (e.g., expanded in height). The ratio of the volume of filler to the volume of the interior channel of the device can then remain substantially constant as the device is radially expanded. For example, the decrease in volume of the interior channel of the device caused by the contracting ramps can be substantially equivalent to the increase in volume of the interior channel of the device 2 caused by the radially expanding top and base plates.

Figure 4:
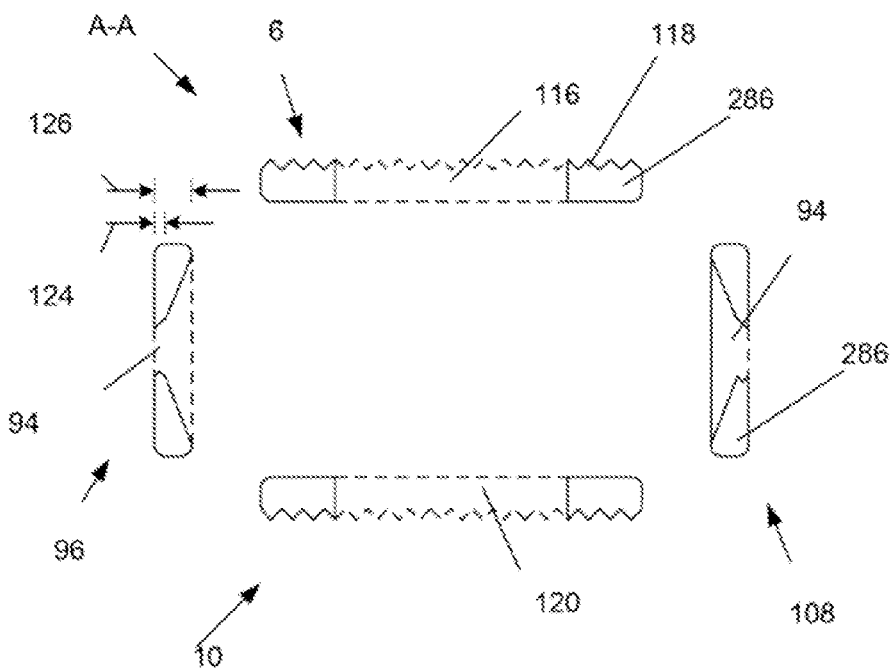

FIG. 4 illustrates that the plates 286 of the first side ramp 96 and/or the second side ramp 108 can thin as the plate 286 nears the threaded ramp port(s). The minimum plate thickness 124 can be substantially less than the maximum plate thickness 126. The minimum plate thickness 124 can be substantially 0. The plate 286 can slope outward (as shown), inward, or a combination of both (e.g., sloping inward and outward concurrently to form the rim of the port at a radius from the longitudinal axis between the radii of the outer and inner surfaces of the plate 286).

Figure 5:
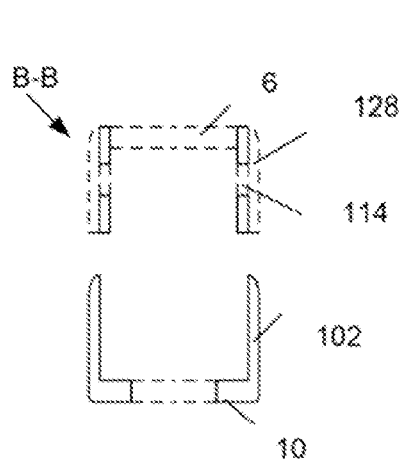
FIGS. 5 and 6 illustrate variations of cross-section B-B of FIG. 1.

FIG. 5 illustrates that the stability bars 102 can be configured to slide into the stability groove 128 when the top and base plates intersect. The radially inner surface of the stability bar 102 can be substantially the same or a greater radius from the longitudinal axis of the expandable support device 188 as the radius of the radially outer surface of the top plate 6 adjacent to the side port 114 (i.e., within the stability groove 128). The stability bar 102 can be configured to not directly attach to the top plate 6 when the top is translated into the base plate, or the stability bars 102 can be configured to bias inward against and frictionally hold the top when the top plate 6 is translated into the base plate.

Figure 6:
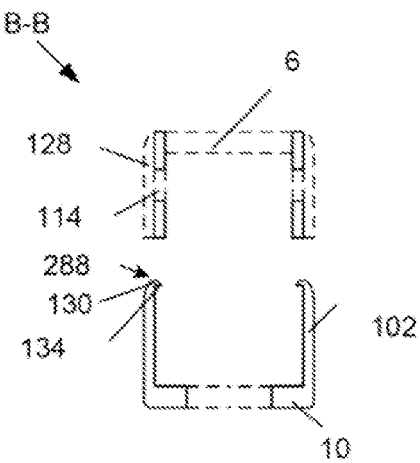

FIG. 6 illustrates that the stability bars 102 can have one or more latches 130 along the length of the stability bar 102, for example at the terminal end of the stability bars 102, as shown. The latch 130 can be configured to attach to the top plate 6. The latch 130 can protrude radially inward. The latch 130 can have a latch top 288 and a latch bottom 134.

The latch top 288 can be configured to allow the top to pass over the latch 130. For example, the latch top 288 can be rounded and configured to push radially outward and clear of the top plate 6 when the top is pressed down into the latch top 288. The latch bottom 134 can be configured to grasp or otherwise attach to the top when the top is translated to a particular location into the base plate.

The stability bars 102 can be configured to resiliently bend radially outward and/or inward.

Figure 7:
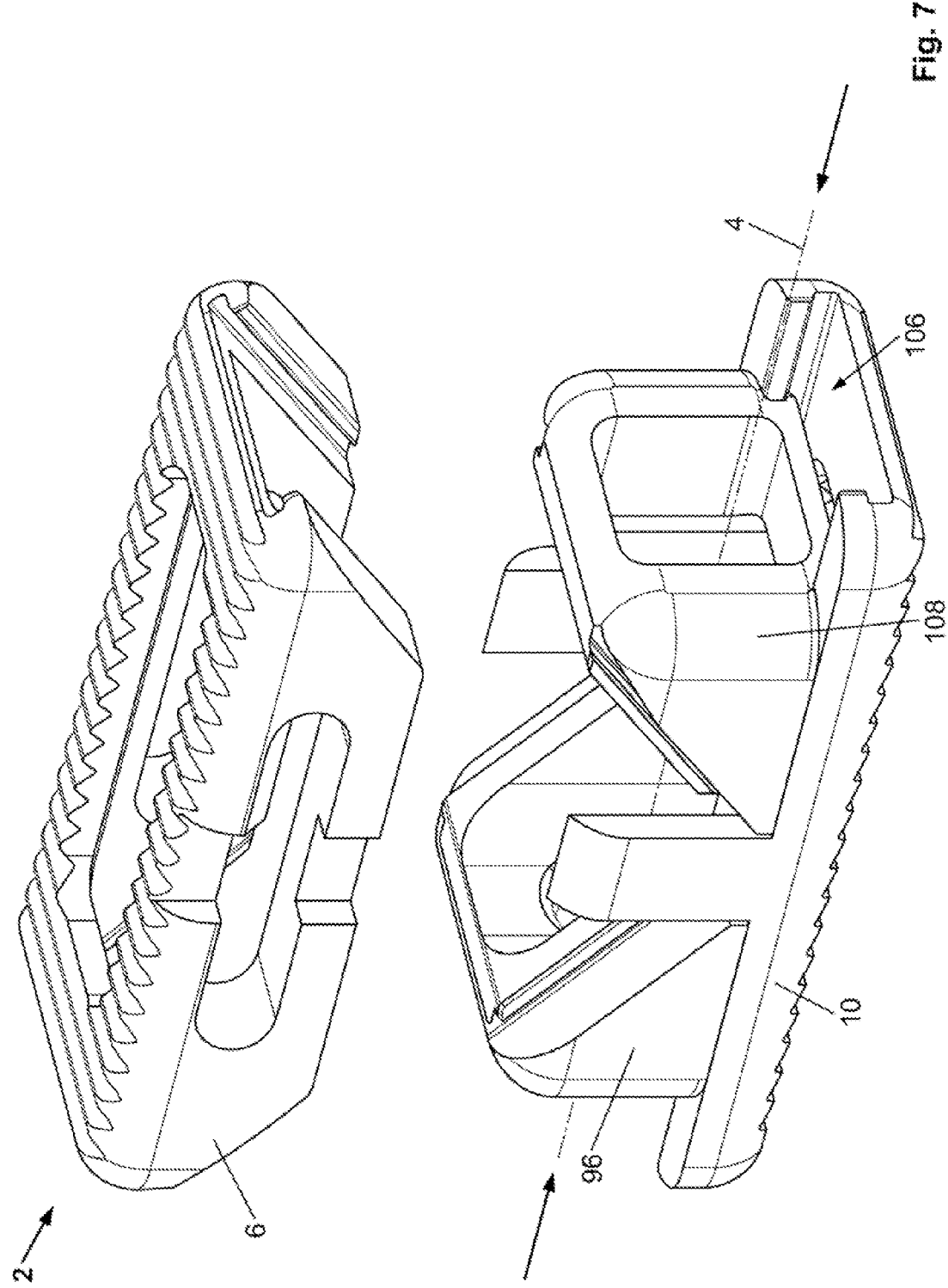
FIG. 7 illustrates the variation of the expandable support device of F*igure* 1 with the ramps slidably attached to the base.

FIG. 7 illustrates that the ramps 96 and 108 can be slidably attached, as shown by arrows, to the base plate 10 before the ramps 96 and 108 are slidably attached to the top plate 6. The ramp second tongues and grooves 98 can be slidably engaged with the base tongues and grooves 106, as shown in FIGS. 12, 13 and 14.

Figure 8:
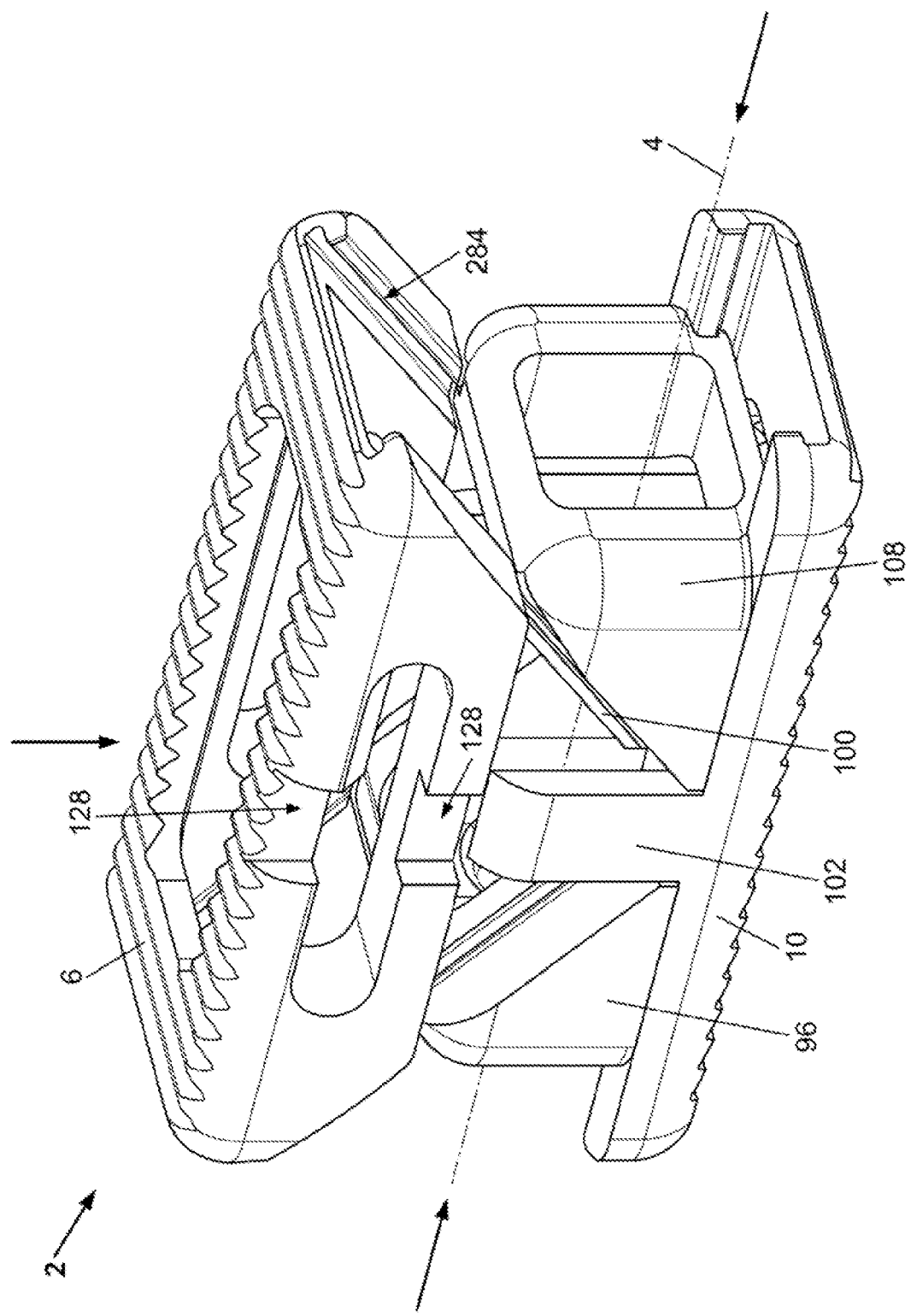
FIGS. 8 and 9 are perspective and side views, respectively, of the variation of the expandable support device of FIG. 7 with the top and ramps in pre-assembly positions.
Figure 9:
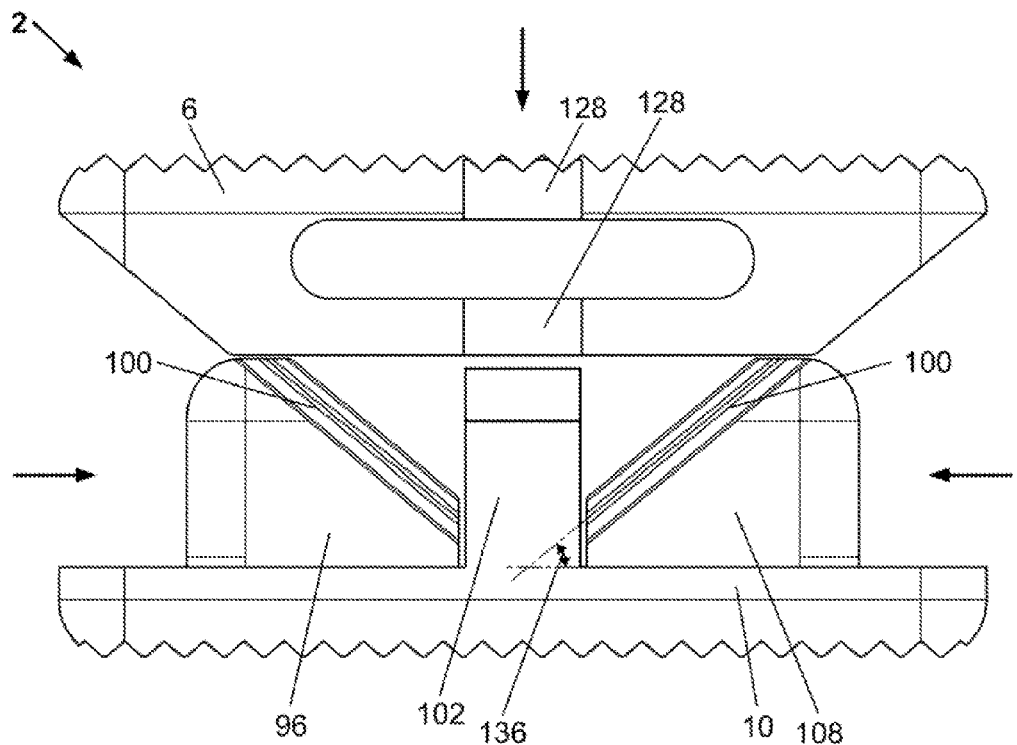

FIGS. 8 and 9 illustrate that the ramps 96 and 108 can be positioned, as shown by arrows, so that one or both ramp first tongues and grooves 100 can be aligned to slidably engage the top tongues and grooves 284 as the top plate 6 is translated toward the base plate, as shown by arrows. The stability bar 102 can be slid into the stability groove 128.

Figure 11:
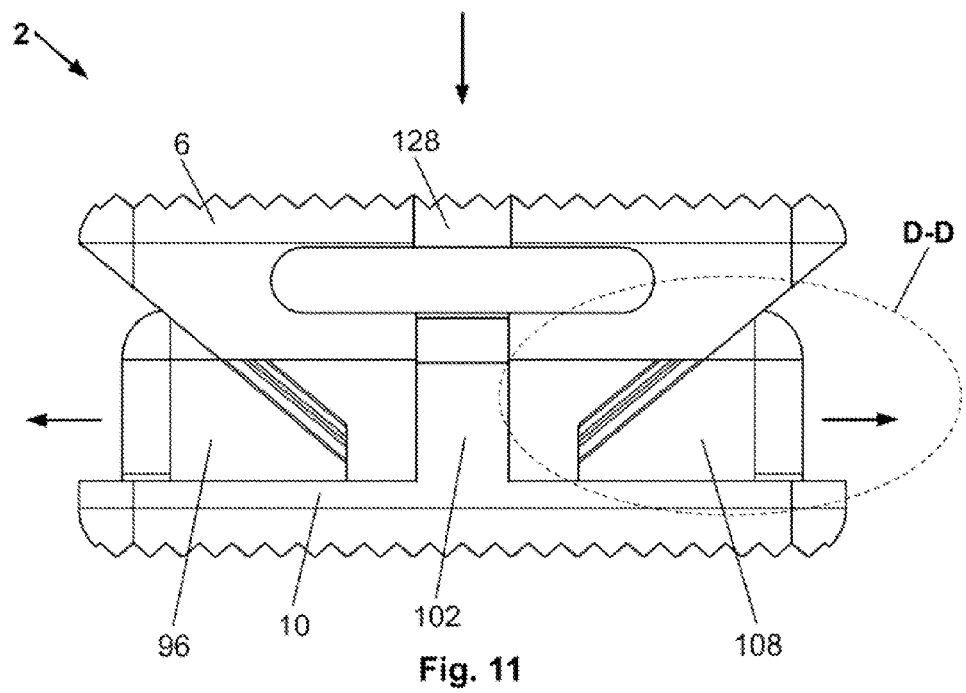
FIGS. 10, 11 and 12 are perspective, side and end views, respectively of the variation of the device of FIG. 1 in an assembled configuration.
Figure 10:
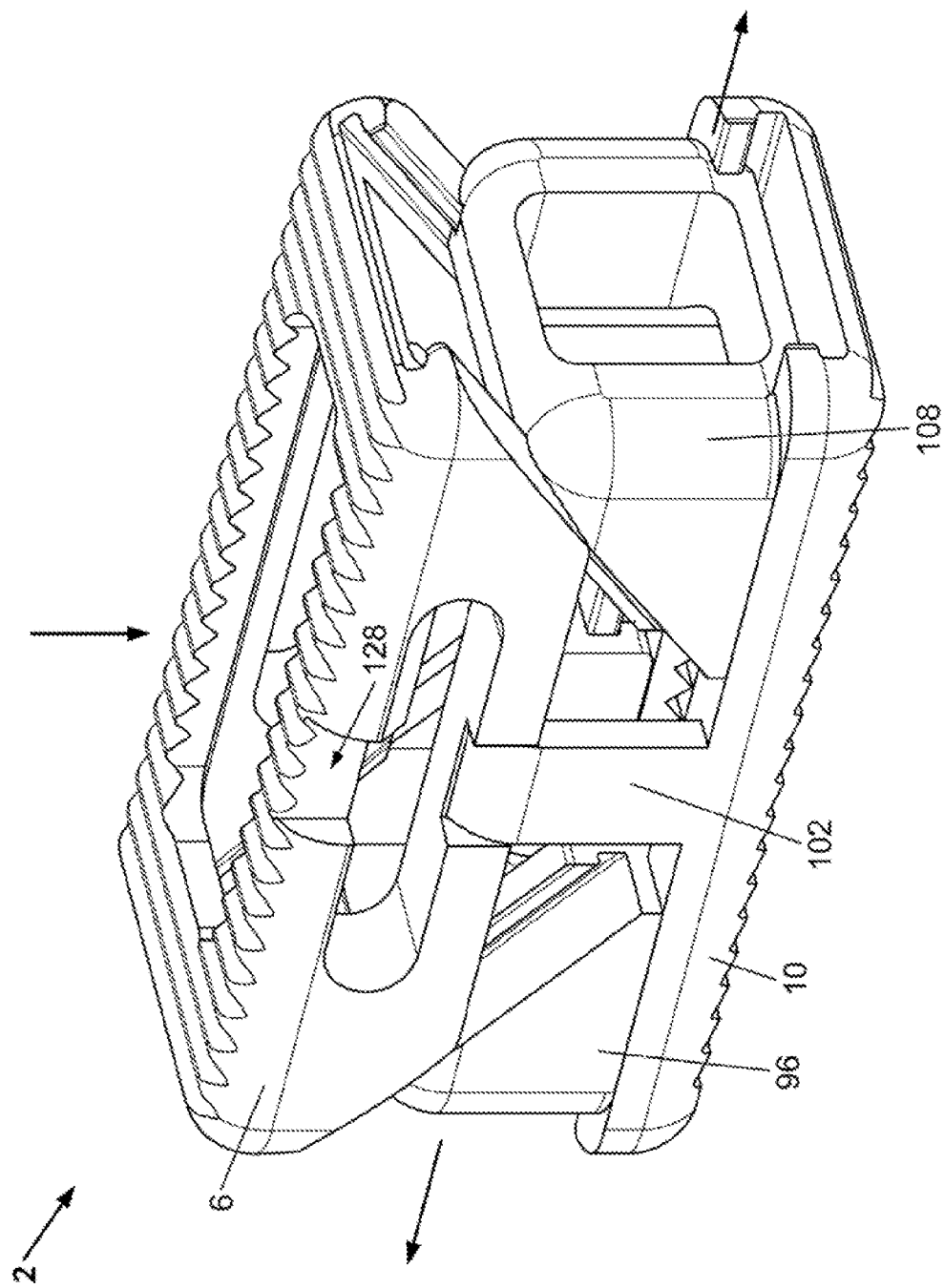
Figure 12:
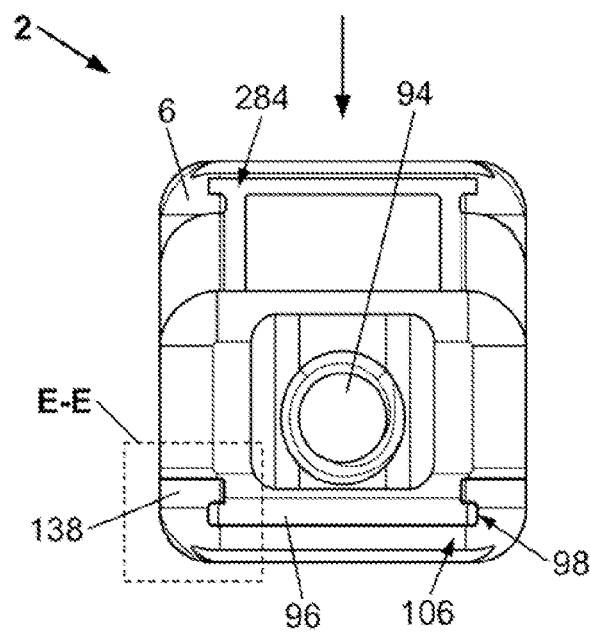

FIGS. 10 through 12 illustrate that as the top plate 6 is translated toward the base plate, as shown by arrows, the top plate 6 can slidably engage one or more of the ramps 96 and 108. The first tongues and grooves can slidably engage the top tongues and grooves 284.

Figure 13:
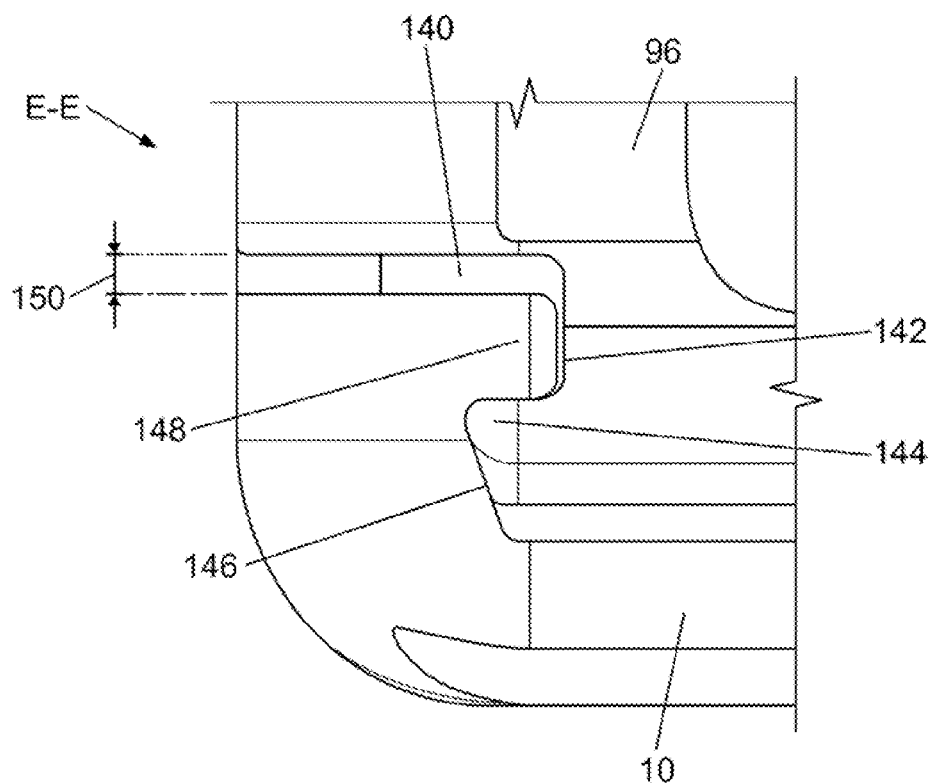
FIG. 13 is a variation of close-up section E-E of FIG. 12 in a first configuration.
Figure 14:
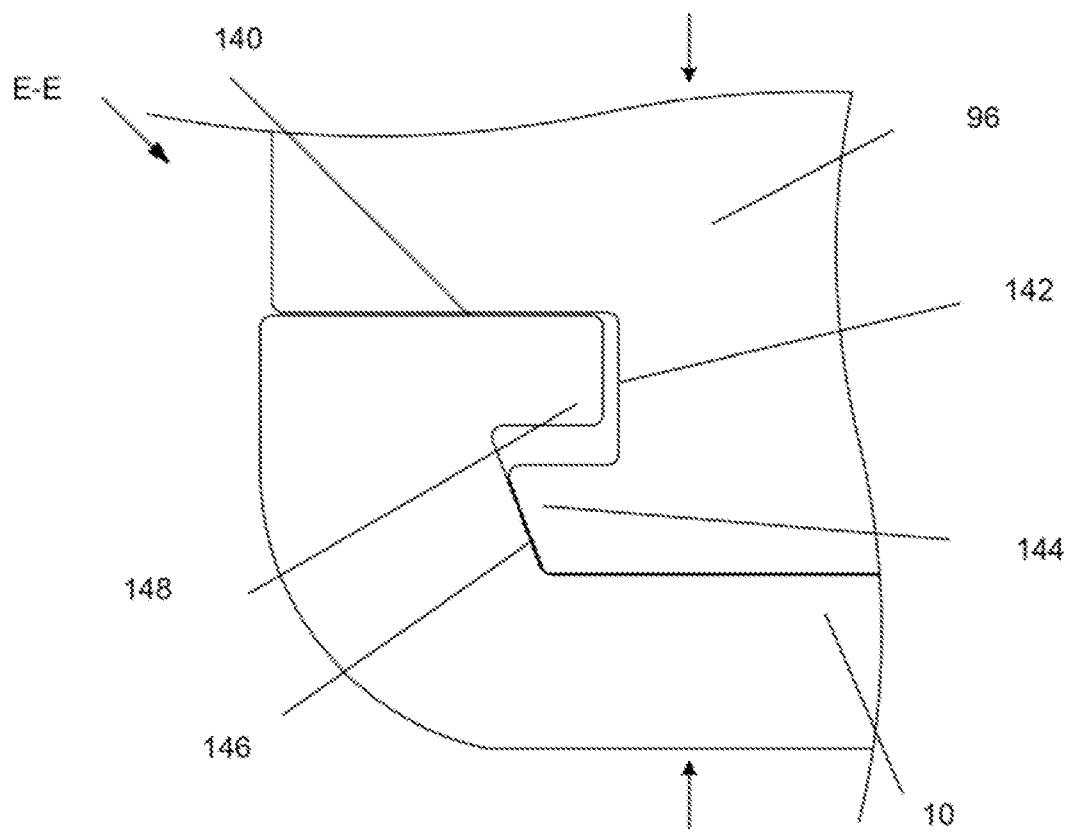
FIG. 14 is a variation of close-up section E-E of FIG. 12 in a second configuration.

FIG. 13 illustrates that there can be a substantial ramp gap 140 between the side ramp and the base plate, for example before the expandable support device 188 is completely deployed. The ramp gap 140 can have a ramp gap height 150. The ramp gap height 150 can vary, for example, from about 0 mm (0 in.) to about 4 mm (0.2 in.). The side ramps can substantially slide along the base plate. For example, the ramp second tongue and groove 98 can slide along the base tongue and groove 106, separated by the ramp gap 140. Most or all of the friction in this configuration can be created by the ramp second tongue in contact with the base tongue 148 and/or side of the base groove 146.

The wall of the base groove 146 can have an outwardly slanted configuration relative to the height of the wall of the base groove 146 from the bottom of the base plate.

FIG. 14 illustrates that the first side ramp 96 and the base 138 can be pressed into or otherwise translated toward each other. For example, after implantation of the device 2, the surrounding tissue in the in vivo environment can naturally compress the device 2.

The ramp gap 140 can be substantially closed. The ramp gap height 150 can be substantially about 0. The side ramps can be substantially friction fit along the base plate. For example, the friction in this configuration can be created along the top surface of substantially the entire base plate including the top of the base tongue 148, and the bottom surface of substantially the entire side ramps.

As the side ramp is pushed, as shown by arrows, toward the base plate, the ramp second tongues 144 can be pressed between the base grooves 146, for example, frictionally fitting the side ramps into the base plate. The base grooves 146 can be tapered, as shown, to force the ramp second tongues 144 to wedge fit or press fit into the base grooves 146 when the side ramp is pushed towards the base plate.

The side ramps can have less friction with the base plate in the configuration of the expandable support device 188 of FIG. 13 than in the configuration of the expandable support device 188 of FIG. 14.

Figure 15:
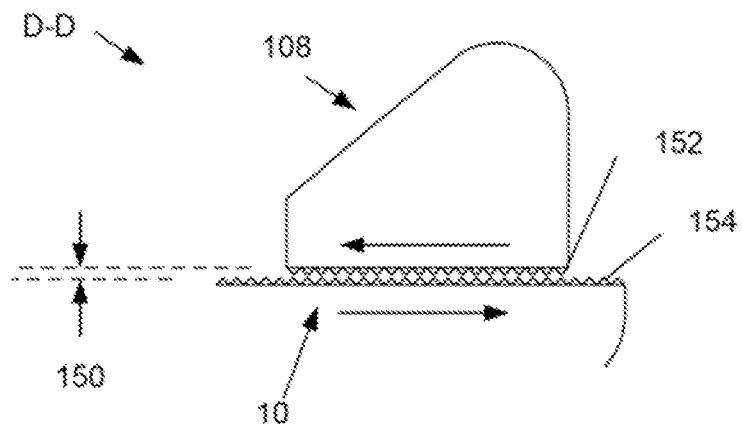
FIGS. 15 and 16 are a variation close-up section D-D of FIG. 11 in first and second configurations, respectively.

FIG. 15 illustrates that the second side ramp 108 (and/or the first side ramp 96, not shown) can have ramp bottom teeth 152 on the side of the second side ramp 108 (and/or first side ramp 96) facing the base plate. The ramp bottom teeth 152 can extend into the ramp gap 140. Either or both side ramps can have teeth on any and/or all sides of the side ramp, for example the surfaces that contact the base plate and the top plate 6. The top plate 6 can have additional teeth, not shown, along surfaces that contact the side ramps.

The ramp bottom teeth 152 and/or base interior teeth 154 can be unidirectionally or bidirectionally oriented (i.e., providing additional resistance against movement in one direction, or substantially the same resistance against movement in either direction).

As the side ramp translates, as shown by arrows, with respect to the base plate, the ramp gap height 150 is substantially non-zero, as shown in FIGS. 13 and 15. When the ramp gap height 150 is substantially non-zero, the ramp bottom teeth 152 can slide over the base interior teeth 154.

Figure 16:
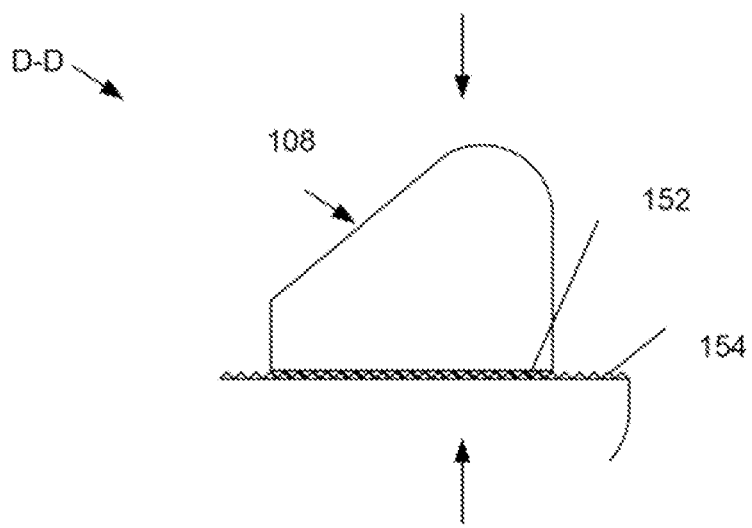

FIG. 16 illustrates that when the side ramp and base plate are pressed together, as shown by arrows, for example when deployed in vivo, the ramp gap height 150 can be minimized, for example approaching about 0 mm (0 in.). The ramp bottom teeth 152 can interlock with the base interior teeth 154. The interlocked ramp bottom teeth 152 and base interior teeth 154 can provide an interference fit or otherwise prevent or minimize the side ramp translating relative to the base plate.

In place of, or in addition to, the ramp bottom teeth 152 and/or the base top teeth, the respective surfaces can have high friction surfaces, for example a textured (e.g., knurled) surface and/or coated with a high friction material. The respective surfaces can also be smooth, having no teeth or texturing.

The side ramp can be pulled away from the base plate by reducing the compressive force between the side ramp and the base plate and pulling or pushing the side ramp.

The side ramp can have a belt and suspenders lock with the base plate.

Figure 17:
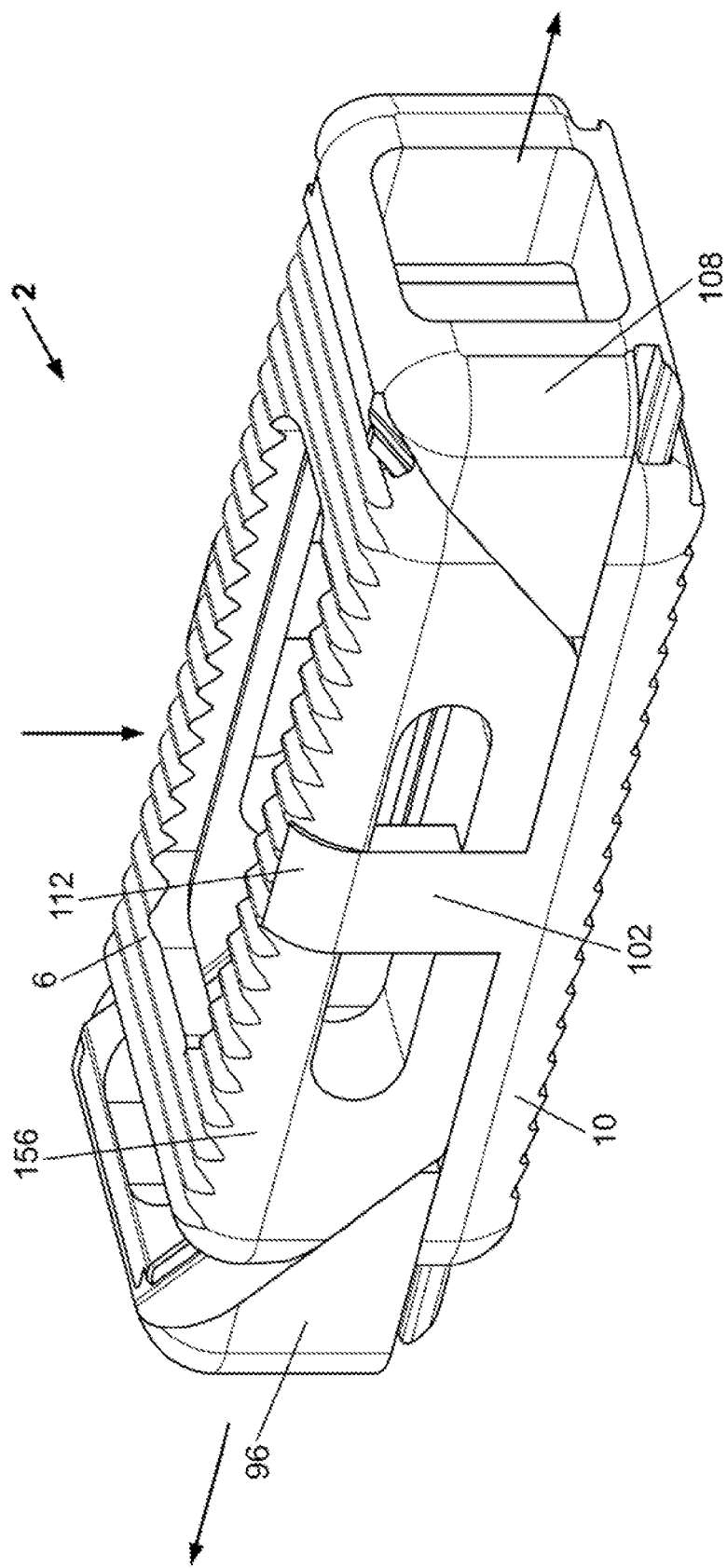
Figure 20:
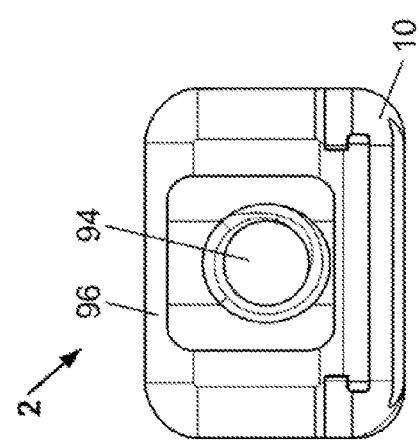
Figure 21:
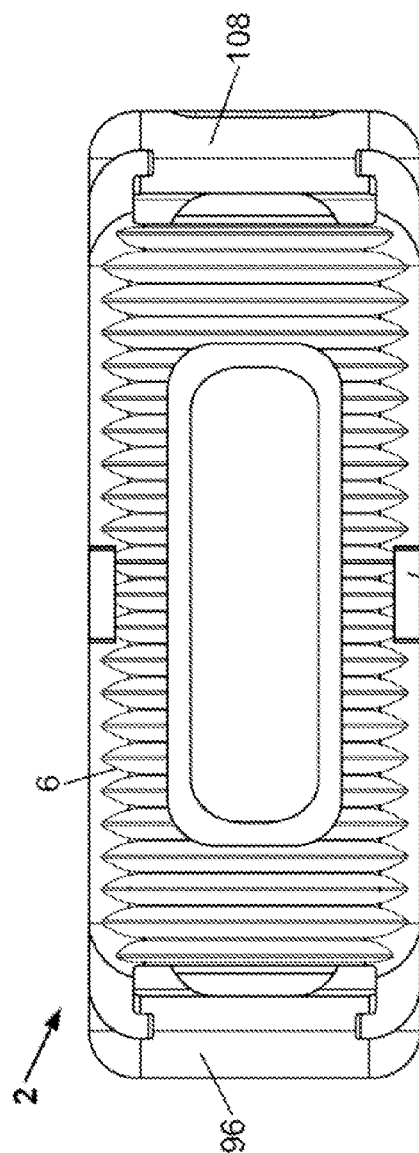

FIGS. 17, 18, and 20 illustrate that the ramps can be pushed outward, as shown by arrows, toward each ramp's respective longitudinal side of the base plate. The ramps 96 and 108 can be pushed outward, for example, by a deployment or other tool. When the ramps 96 and 108 are slid outward, as shown, the top plate 6 and base plate can translate toward each other, as shown by arrow. The top plate 6 and base plate can then have a radially compressed (e.g., only in the "y"-axis or from the top of the page to the bottom of the page of FIGS. 17, 18, and 20) configuration. The top plate 6 can interference fit against the bottom plate 10 when the expandable support device 188 is fully radially compressed, as shown. The interference fit of the top against the bottom plate, and the slidable attachment of the ramps 96 and 108 to the top and the bottom plate 10 can lock the top plate 6, base plate and ramps 96 and 108 together (e.g., not allowing any to separate). The device 2 can be attached to a deployment tool 80 (e.g., by removably attaching to one or more ramp ports) and/or delivered to a target site 264 in the radially compressed configuration.

Figure 22:
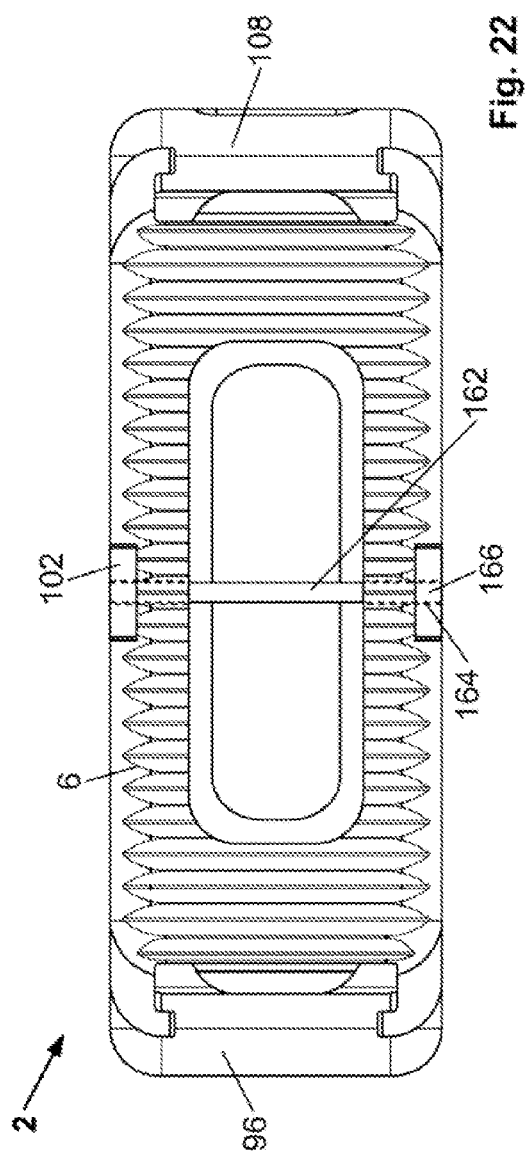

FIGS. 19 and 22 illustrate that one or more locking pin channels 164 can be defined transversely through the device 2. A locking pin 162 can be inserted through each locking pin channel 164. The locking pin 162 can be inserted through the locking pin channel 164 after the device 2 has been inserted at the target site 264 and expanded. The locking pin channel 164 can be defined by locking pin ports 166 on the stability bars 102 and the side port 114. The locking pin ports 166 can be circular, as shown, oval, or combinations thereof.

The locking pin 162 can be configured to limit the vertical expansion of the device 2. For example, the locking pin 162 can be configured to substantially prevent the device 2 from disassembling.

Figure 23:
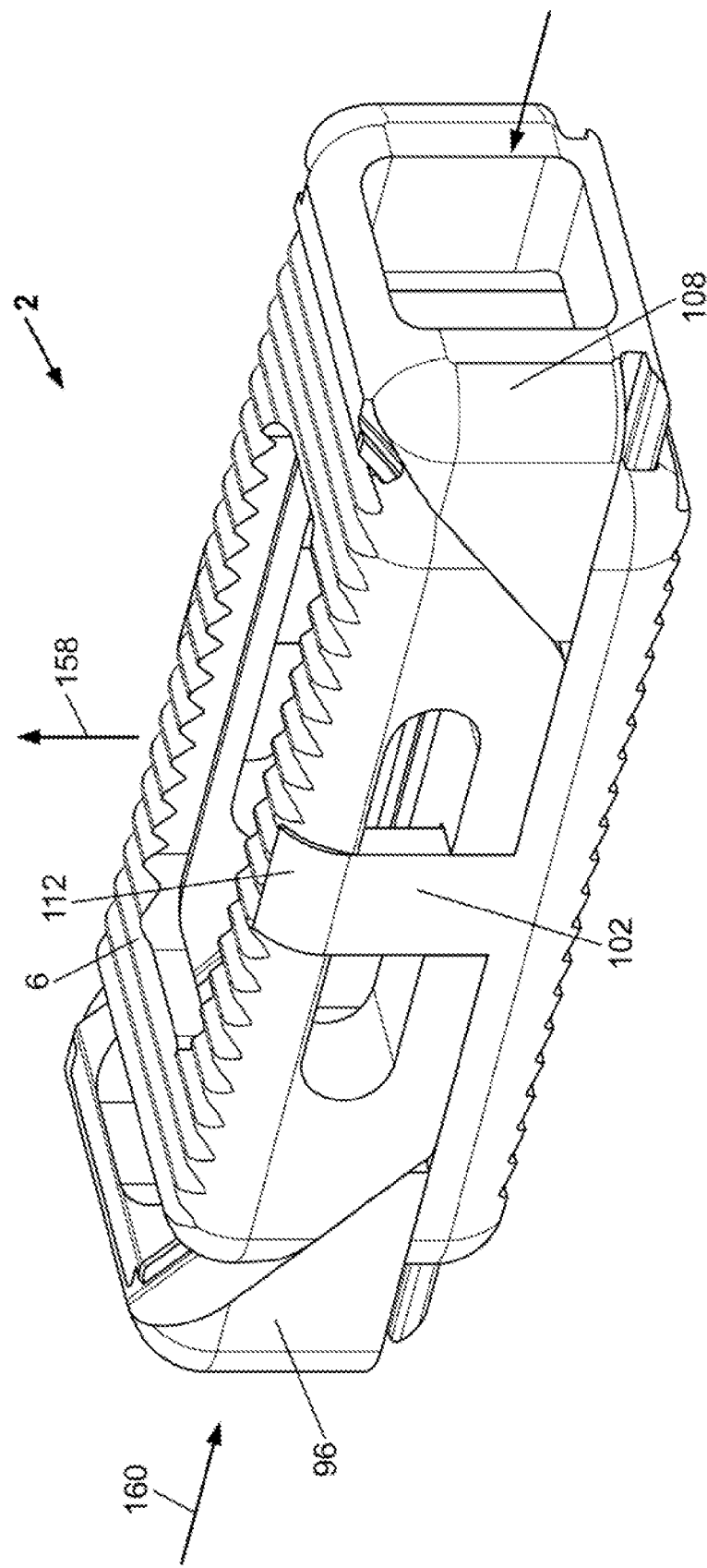
FIG. 23 illustrates a method of longitudinally compression and radially expanding the variation of the device of FIG. 17, for example after deployment at a target site.

FIG. 23 illustrates that the device 2 can be longitudinally compressed, as shown by arrows, resulting in radial and/or vertical expansion, as shown by arrow, for example performed after the device 2 is positioned within a vertebra or between vertebrae. The ramps 96 and 108 can be slidably translated along the longitudinal axis and inward and/or toward the center of the device 2. The expansion of the device 2 can increase the height and provide structure support for a compressed or otherwise damaged vertebra (e.g., when the device 2 is deployed within a vertebra) and/or return adjacent vertebrae to a more natural/physiological configuration (e.g., when the device 2 is deployed between adjacent vertebrae).

Figure 24:
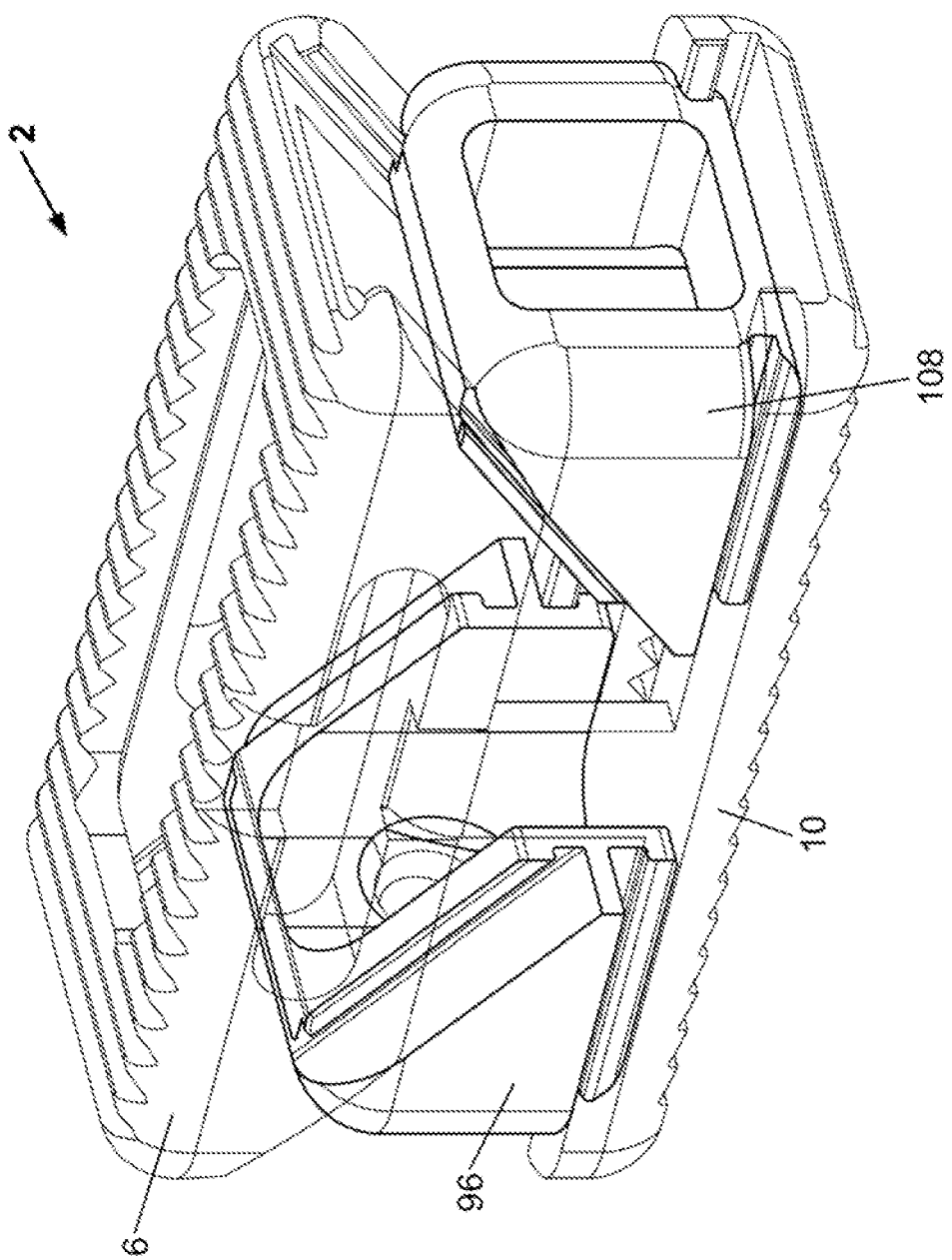

FIGS. 24 and 25 illustrate the device 2 in a deployed configuration, for example after completion of the longitudinal compression 160 and radial and/or vertical expansion as shown in FIG. 23.

FIG. 26 illustrates a variation of the locking pin 162 that can have a pin shaft 170 with a driver slot 172, for example, configured to receive a screw driver or drill bit. The pin shaft 170 can have pin thread 168 configured to releasably or fixedly attach to one or both of the ramp ports. The pin thread 168 can extend along all or part of the length of the pin shaft 170. The pin shaft 170 can be rotatably or fixedly attached to or integral with a locking plate 290. The locking plate 290 can be at the end of the pin shaft 170 with the driver slot 172. The locking plate 290 can be at the same or opposite end of the pin shaft 170 from the thread.

Figure 27:
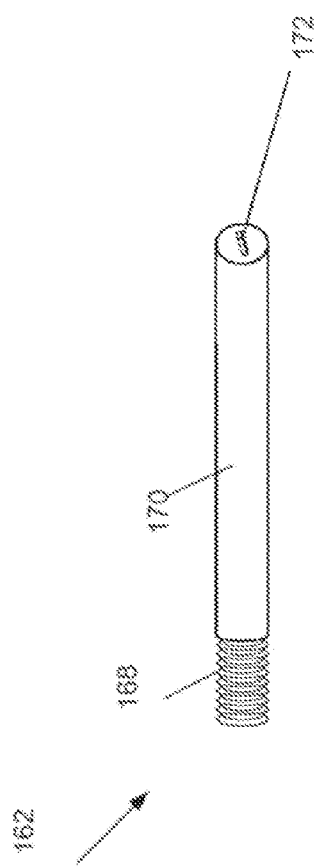

FIG. 27 illustrates that the pin shaft 170 can have no locking plate 290. The pin thread 168 can be at the end of the pin shaft 170 with the driver slot 172. One end of the pin shaft 170, for example opposite the driver slot 172, can be an abutment end 174.

Figure 28:
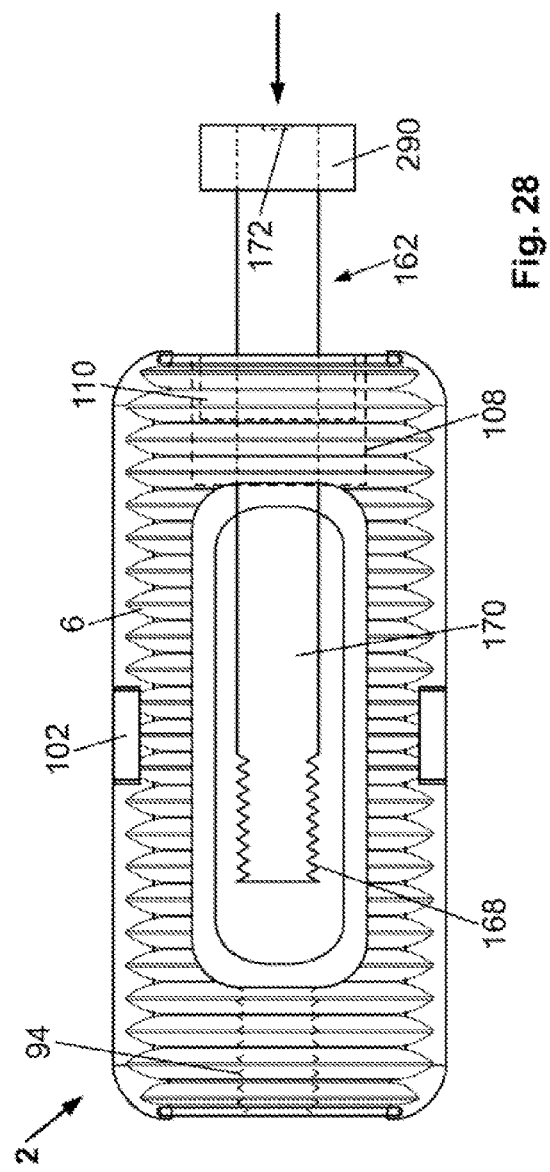

FIG. 28 illustrates that the locking pin 162 can be inserted, as shown by arrow, through the second side ramp 108. FIG. 29 illustrates that the pin shaft 170 can be translated and rotated, as shown by arrows, to screw the pin thread 168 into the threaded distal ramp port 94 in the first side ramp 96. The ramp locking plate can fit into the ramp locking plate port 110. The locking pin 162 can be screwed tightly enough to substantially fix the locking pin 162.

FIG. 30 illustrates that the locking pin 162 can be inserted, as shown by arrow, through the threaded ramp port. The second side ramp 108 and/or the top and/or the bottom plates can have a ramp abutment section 180. The ramp abutment section 180 can be configured to interference fit with and/or fixedly attach to the abutment end 174.

FIG. 31 illustrates that the pin shaft 170 can be translated and rotated, as shown by arrows. The abutment end 174 can interference fit and/or fixedly attach to the ramp abutment section 180.

A biocompatible adhesive or epoxy can be applied to the pin thread 168, threaded ramp port, abutment end 174, ramp abutment section 180, or combinations thereof.

FIGS. 32, 33 and 34 illustrate that one, two or more locking pin channels 164 can be defined longitudinally through the device 2. One, two or more locking pins 162 can be inserted in each locking pin channel 164, for example during or after deployment of the remainder of the device 2. The locking pins 162 can prevent overexpansion and/or overcompression and/or disassembly of the device 2.

The locking pin channel 164 can have locking pin ports 166 through the top, and/or bottom plates, and/or either or both side ramps.

Two locking pin channel 164 can be located on opposite sides of the threaded ramp port. The locking pin channels 164 and ports can have a circular cross-section (i.e., be cylindrical), as shown in FIG. 34.

FIGS. 35 and 36 illustrates that the locking pin 162 can be cylindrical. The locking pin channel 164 and locking pin port 166 can have elongated cross-sections, such as an oval or rectangular or oblong cross-sections. The locking pin 162 can be free to move vertically within a range of motion within the locking pin port 166.

FIGS. 37 and 38 illustrate that the locking pin 162 can be a substantially similar shape and size as the locking pin channel 164. The locking pin 162 can be substantially unmovable within the locking pin port 166. The locking pin 162, locking pin channel 164 and locking pin port 166 can all have elongated cross-sections, such as an oval or rectangular or oblong cross-sections.

One or both of the ramps 96 and 108 can have first fixing teeth 192. The first fixing teeth 192 can be in contact with the top and/or the bottom. The top and/or the bottom (shown as bottom only) plates 286 can have second fixing teeth 190.

The first fixing teeth 192 can mechanically interact with the second fixing teeth 190 to allow relative translation in a first direction. The first fixing teeth 192 and the second fixing teeth 190 can interact to obstruct (e.g., by interference fitting the first fixing teeth 192 against the second fixing teeth 190) relative translation in a second direction. For example, the fixing teeth can obstruct the side ramps from moving longitudinally away from each other (i.e., and obstruct the top from moving closer to the bottom). Also for example, the fixing teeth can allow relative translation of the side ramps toward each other (i.e., and allow the top to move away from the bottom).

The second side ramp 108 can have a first end 186. The first end 186 can be configured to dissect tissue. The first end 186 can have a blunt or sharp point.

The second side ramp 108 can have a tool connector 184, such as an externally and/or internally threaded cylinder extending longitudinally from the second side ramp 108 away from the first side ramp 96. The tool connector 184 can be configured to removably attach to a deployment tool 80.

The first side ramp 96 and second side ramp 108 can be longitudinally compressed toward each other. For example, an external deployment tool 80 can be attached to the first side ramp 96 and second side ramp 108 and apply a compressive force. The base 138 and top plates 6 can expand away from each other.

The first fixing teeth 192 can unidirectionally interference fit the second fixing teeth 190. The unidirectional interference fit of the first fixing teeth 192 and the second fixing teeth 190 can substantially impede or prevent the opposite ramps 96 and 108 from moving longitudinally away from each other, for example, therefore impede or preventing compression 196 of the top toward the bottom and vice versa.

The unidirectional interference fit of the first fixing teeth 192 and the second fixing teeth 190 can allow the opposite ramps 96 and 108 to move longitudinally toward each other, for example, therefore allowing the top to expand away from the bottom and vice versa.

The expandable support devices 188 can have textured and/or porous surfaces for example, to increase friction against bone surfaces, and/or promote tissue ingrowth. The expandable support devices 188 can be coated with a bone growth factor, such as a calcium base 138.

Figure 39A:
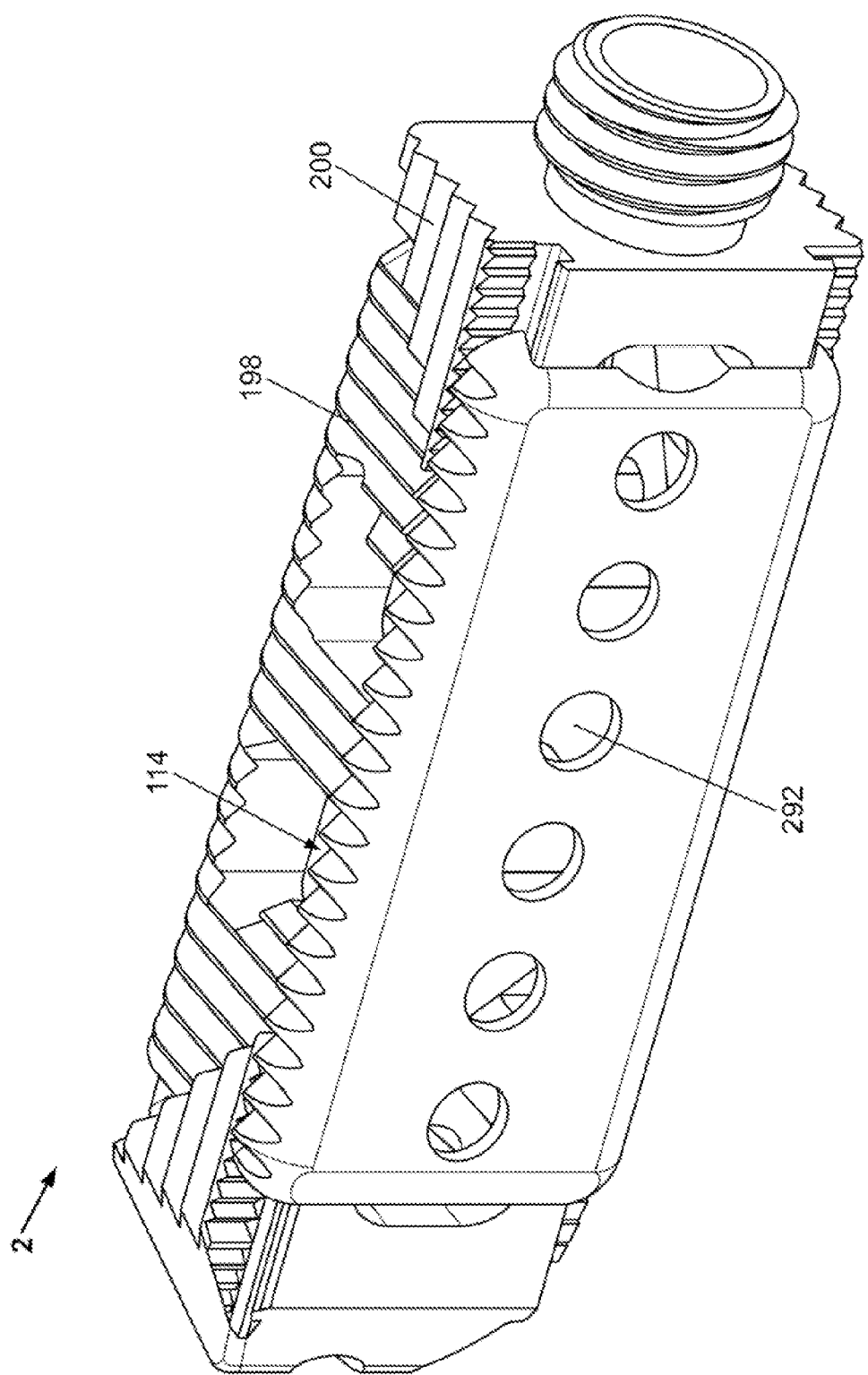
FIGS. 39a, 39b and 39c are bottom perspective, end and side views, respectively, of a variation of the device in a longitudinally expanded configuration.
Figure 39B:
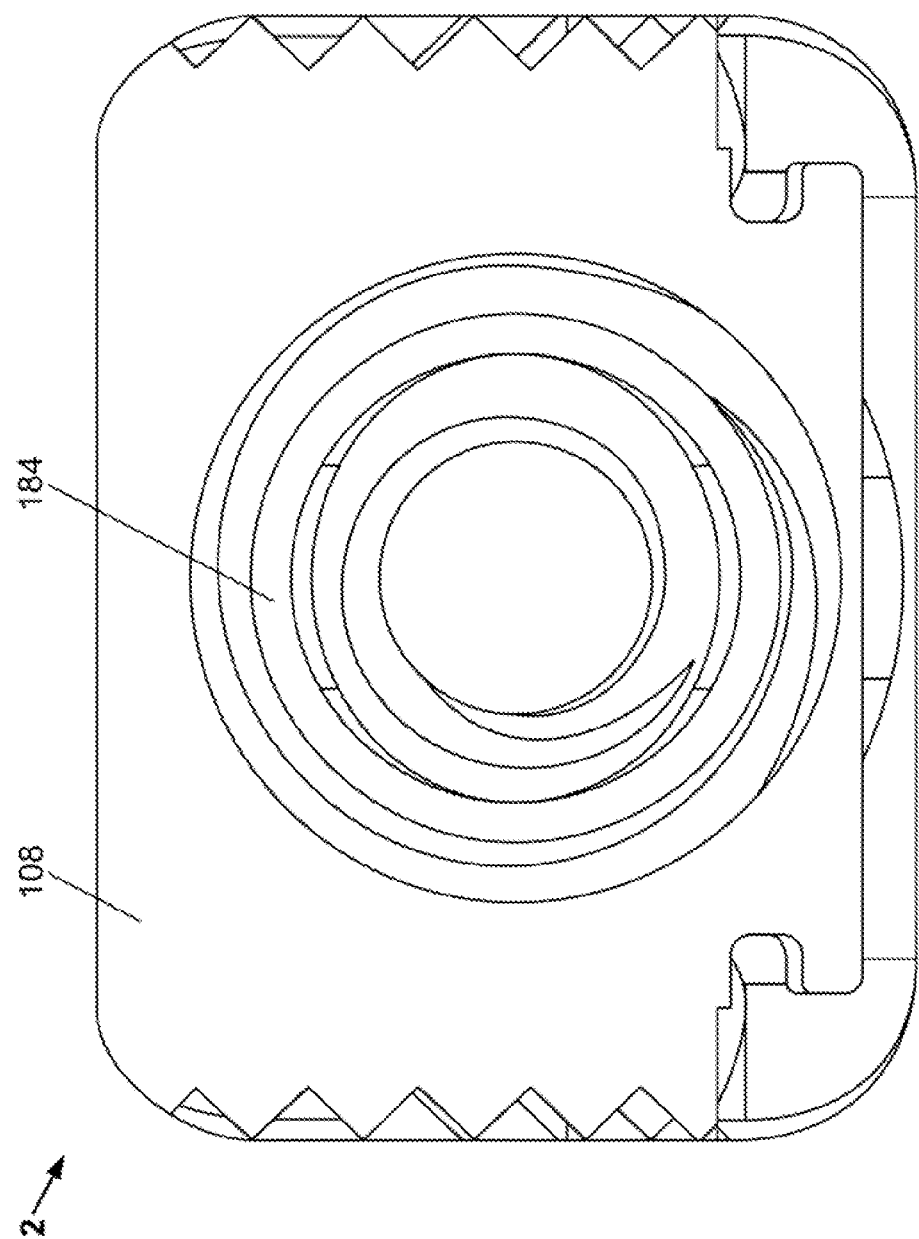
Figure 39C:
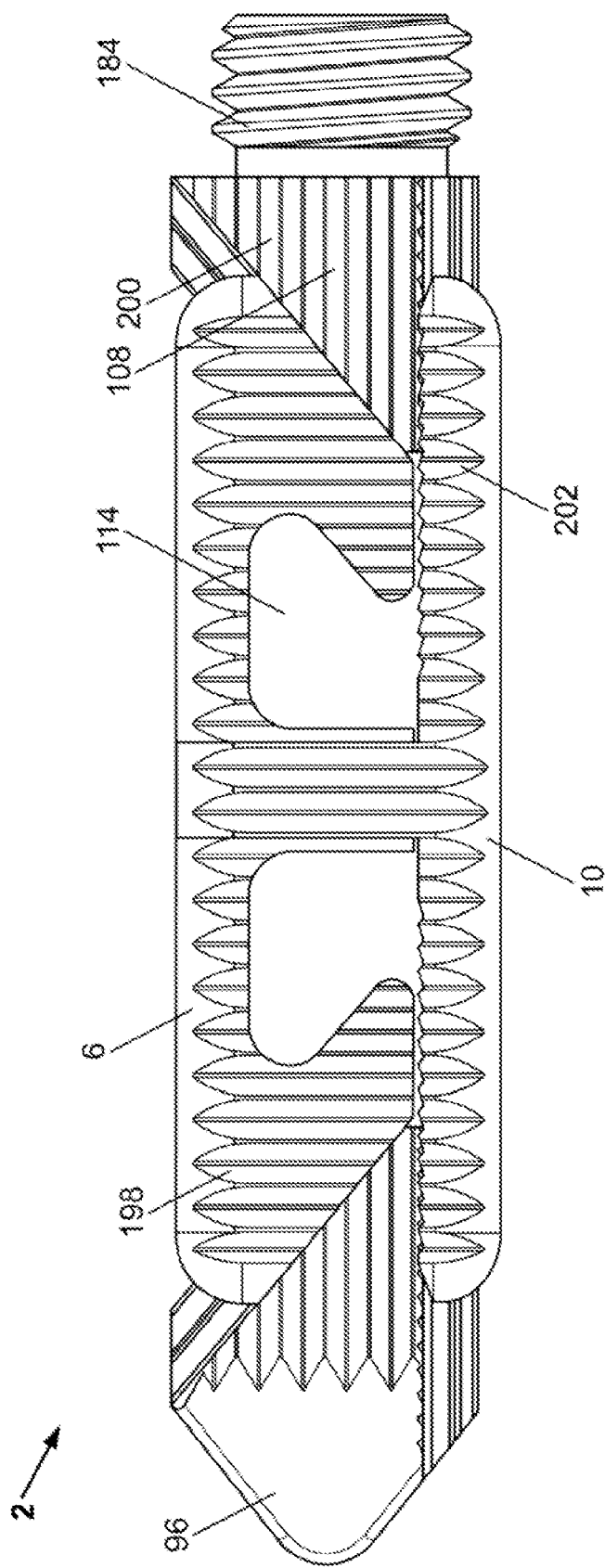

FIGS. 39a through 39c illustrate that the bottom ports can be one or more circular ports, for example six ports. The bottom ports can be aligned in a single row parallel with the longitudinal axis of the device 2.

The side ports 114 can open against the edge of the top plate 6 on one or more sides (e.g., the bottom sides, as shown) of the side ports 114.

The top plate 6 can have top plate side teeth 198 on the external lateral sides of the top plate 6. The bottom plate 10 can have bottom plate side teeth 202 on the external lateral sides of the bottom plate. The top plate side teeth 198 and/or the bottom plate side teeth 202 can be oriented from the top to the bottom of the device 2 (i.e., perpendicular to the longitudinal axis of the device 2). The top plate side teeth 198 can be aligned with the bottom plate side teeth 202.

The external lateral sides of the first side ramp 96 and/or second side ramp 108 can have ramp side teeth 200. The ramp side teeth 200 can be oriented parallel with the longitudinal axis of the device 2. The top plate side teeth 198 and/or the bottom plate side teeth 202 can be oriented perpendicular to the orientation of the ramp side teeth 200.

Figure 40A:
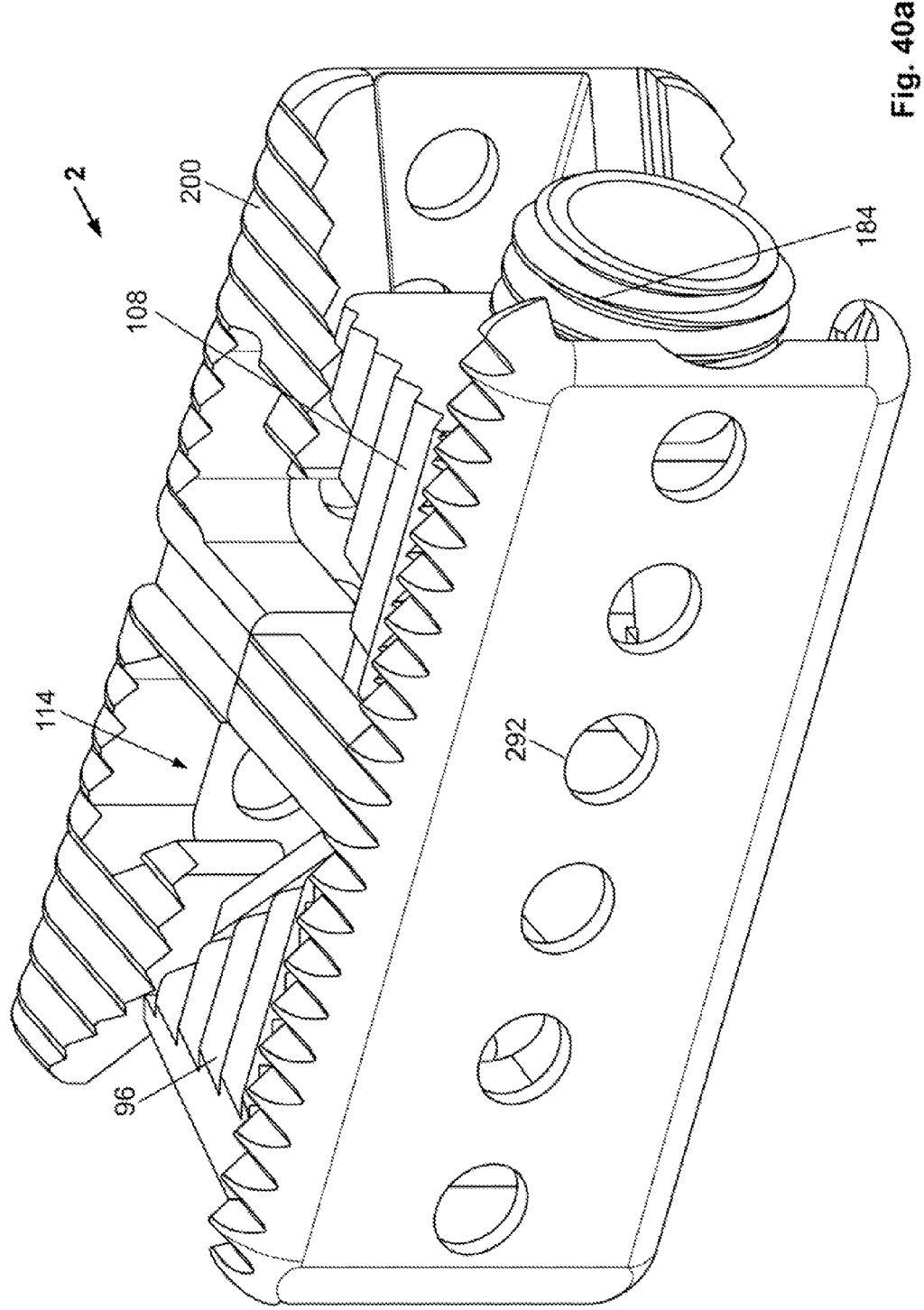
FIGS. 40a, 40b, and 40c are bottom perspective, end and side views, respectively, of the device of FIGS. 39a through 39c in a longitudinally compressed and radially expanded configuration.
Figure 40B:
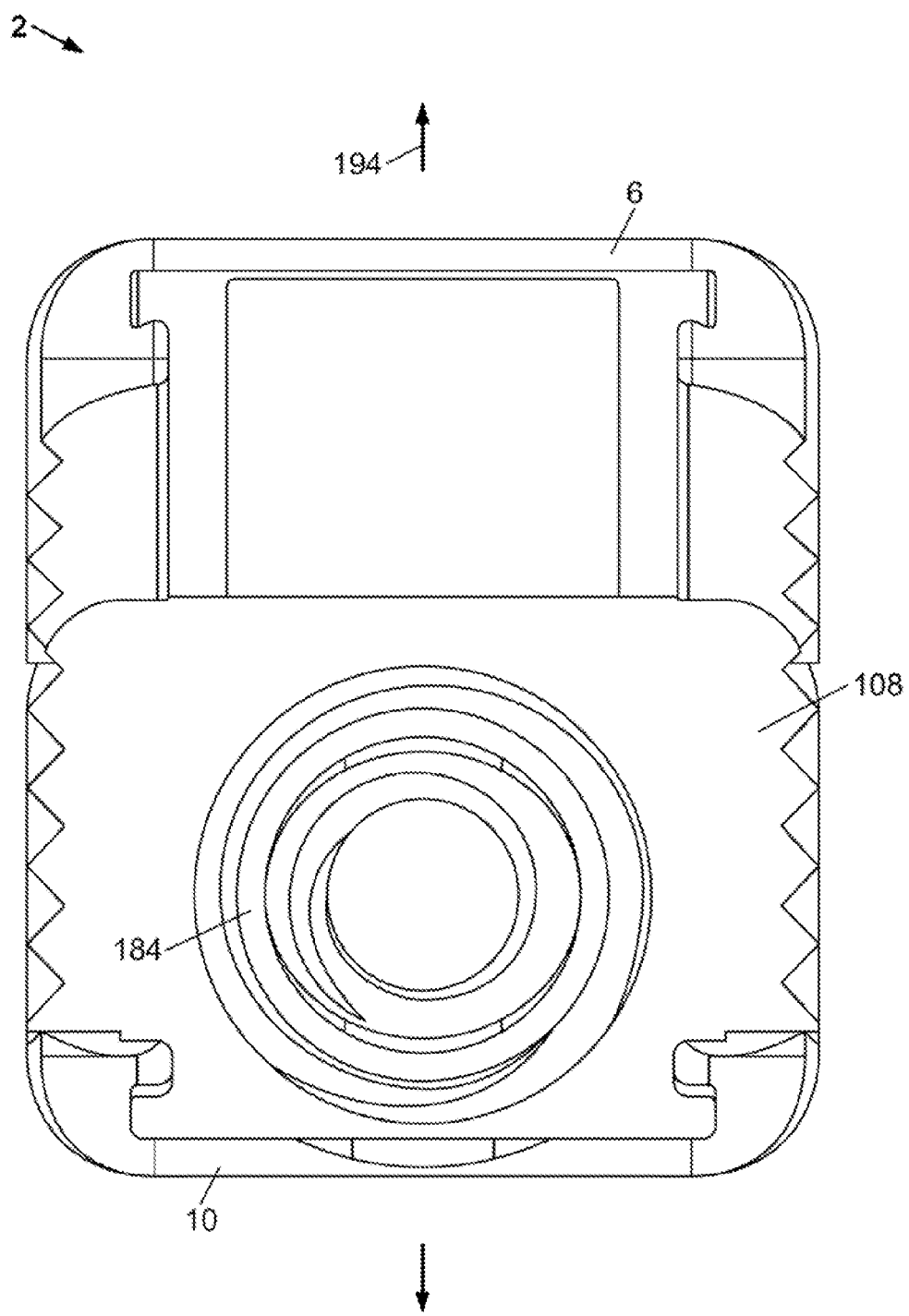
Figure 40C:
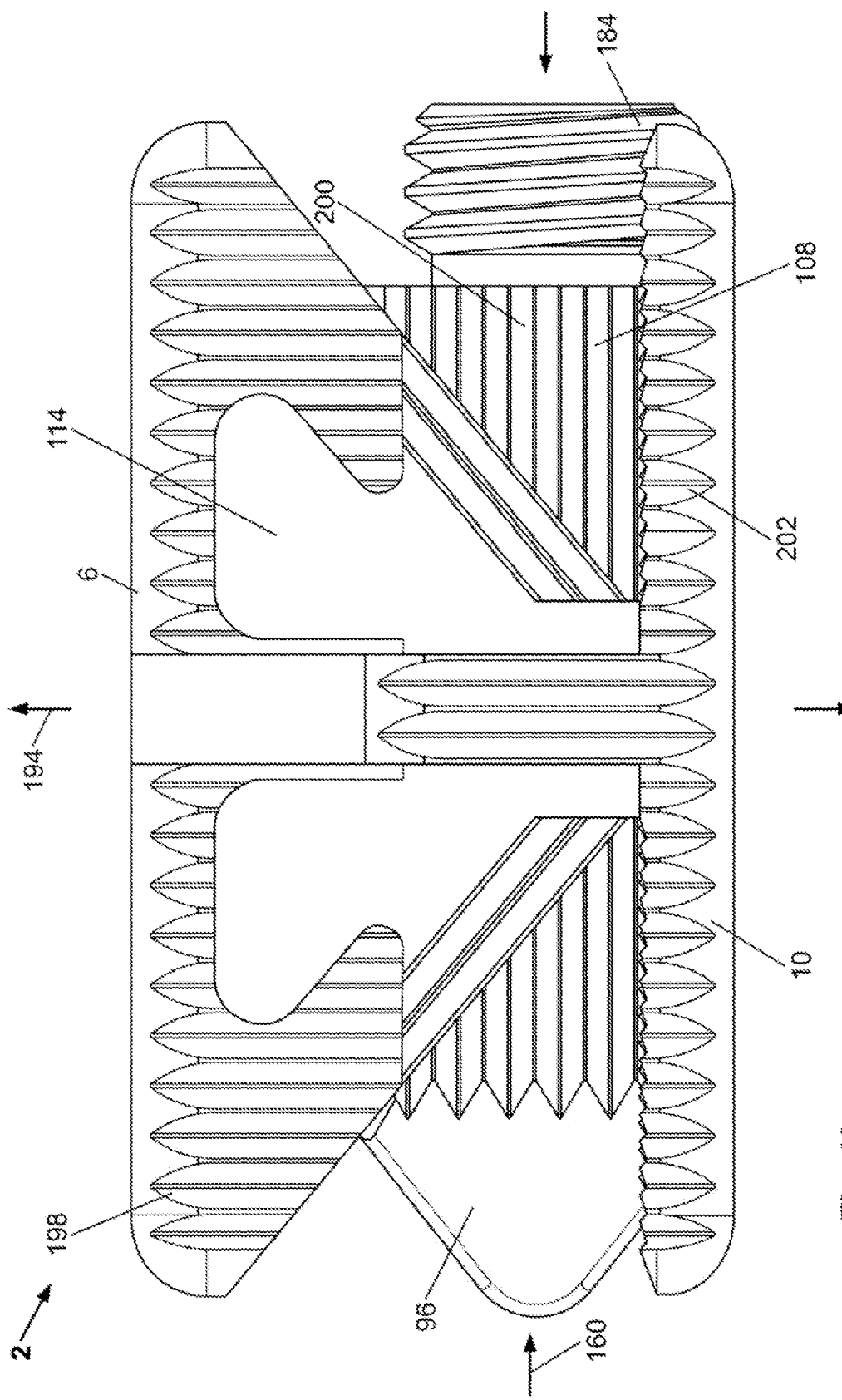

FIGS. 40a through 40c illustrate that the top plate 6 and/or bottom plate 10 can be expanded away from each other in the directions of the orientation of the longitudinal axes of the top plate side teeth 198 and the bottom plate side teeth 202. The first and/or second side ramps 108 can be contracted toward one another in the direction of the orientation of the longitudinal axis of the ramp side teeth 200 of the first and second side ramps 108. The top plate side teeth 198, bottom plate side teeth 202, and ramp side teeth 200 can act as low-friction rails 42 against surrounding tissue when the device 2 is radially expanded at the target site 264.

The side ports 114 that open to the bottom edge of the top plate 6 can create a single side port 114 that can extend to the bottom plate.

The plates 286 and wedges can be rigid or exhibit ductile or deformable expansion during deployment. The transverse cross-section of the device 2 can be non-round. For example, the device 2 can have a square or rectangular transverse cross-section. The device 2 can have a substantially triangular or quadrilateral (e.g., trapezoidal) cross-section. The device 2 can have a round, hexagonal, octagonal, or other transverse cross-sectional configuration.

FIGS. 41a through 41d illustrate that the device 2 can be curved, rounded (e.g., a continuous curvature along the entire length) or bent (e.g., at one or more angles at specific, discrete positions along the length). Any or all of the components of the device 2 can be curved, for example the top plate 6, bottom plate 10, a distal ramp 96, the proximal ramp 108, and combinations thereof. During use, the device 2 can be inserted into a target site, for example intervertebrally, rotating and translating the device 2, so the concave aspect of the curvature can be positioned to miss nearby sensitive tissue (e.g., the spinal cord) during placement.

The longitudinal axis of the device 2 can have a device radius of curvature 300. The device radius of curvature 300 can be from about 0.5 cm (0.2 in.) to about 40 cm (16 in.), more narrowly from about 1 cm (0.4 in.) to about 20 cm (8 in.), yet more narrowly from about 1.9 cm (0.75 in.) to about 7.0 cm (2.75 in.), for example about 3.2 cm (1.25 in.).

The proximal ramp 108 can have one or more proximal protrusions 304. For example, a single protrusion can extend proximally from the proximal ramp 108 centered with or asymmetric or off-center (as shown) to the longitudinal axis 4. The protrusion 304 can have a proximal ramp hole 302a, for example extending from the top of the protrusion 304 part or all of the way through the protrusion 304.

A deployment tool can releasably or fixedly attach to the proximal ramp hole 302a and/or protrusion 304. For example, the deployment tool can be rotatably attached to the proximal ramp hole 302a. For example, the deployment tool can have a removable pin that can be inserted into the hole proximal ramp hole 302a. The pin, still fixed to the deployment tool, can then be press fit (e.g., friction fit or interference fit) or rotated inside of the hole 302a, acting as a rotatable hinge. The pin can rotationally stabilize the device 2.

The pin can act as a stabilization device. The deployment tool can press on one or both sides of the protrusion 304 to rotate the device 2 about the proximal ramp hole 302a.

The distal ramp 96 can have a distal ramp keyhole 302b. The distal ramp keyhole 302b can extend from the top of the distal ramp 96 part or all the way through the distal ramp 96. The distal ramp keyhole 302b can be cylindrical (as shown), square, triangular, oval, rectangular, or star-shaped in cross section. An attachment key 308 can be inserted into the distal ramp key hole 302b, as shown by arrow in FIG. 41b. The inserted attachment key 308 can abut against the larger cylinder 170b and the distal The attachment key 308 can have the same cross-section as the distal ramp key hole 302b.

The locking pin 162 can be straight (as shown) or curved, such as having a substantially equal radius of curvature to the longitudinal axis. The locking pin 162 can have a proximal locking head plate or tool interface proximal section 290a that can extend proximally of the proximal ramp 108 when the device 2 is in a radially contracted and longitudinally expanded configuration. The locking pin 162 can be fixedly or detachably attached to the distal ramp 96.

Figure 42A:
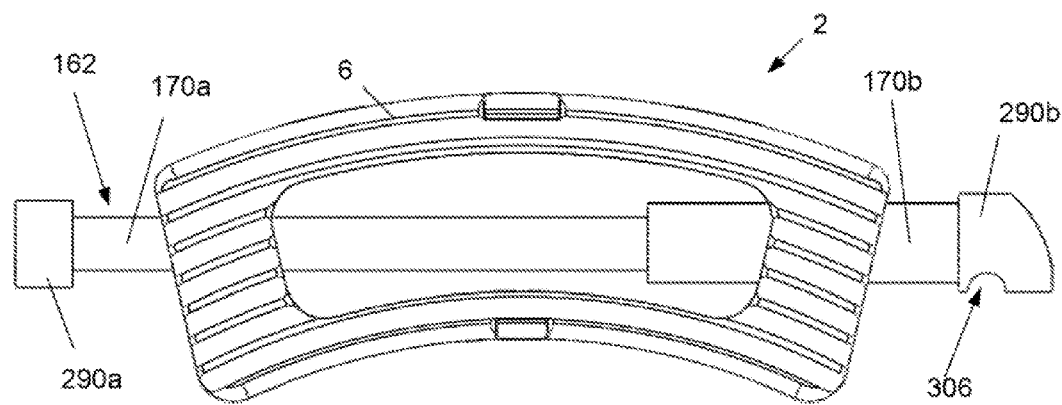
FIGS. 42a through 42c are top, side and top perspective views, respectively, of the variation of the device of FIGS. 41a through 41d with the side ramps not shown for illustrative purposes.
Figure 42B:
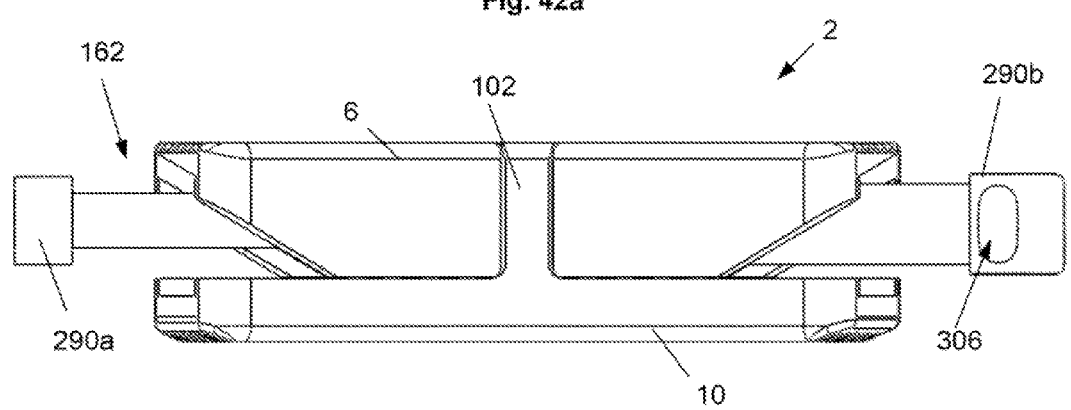
Figure 42C:
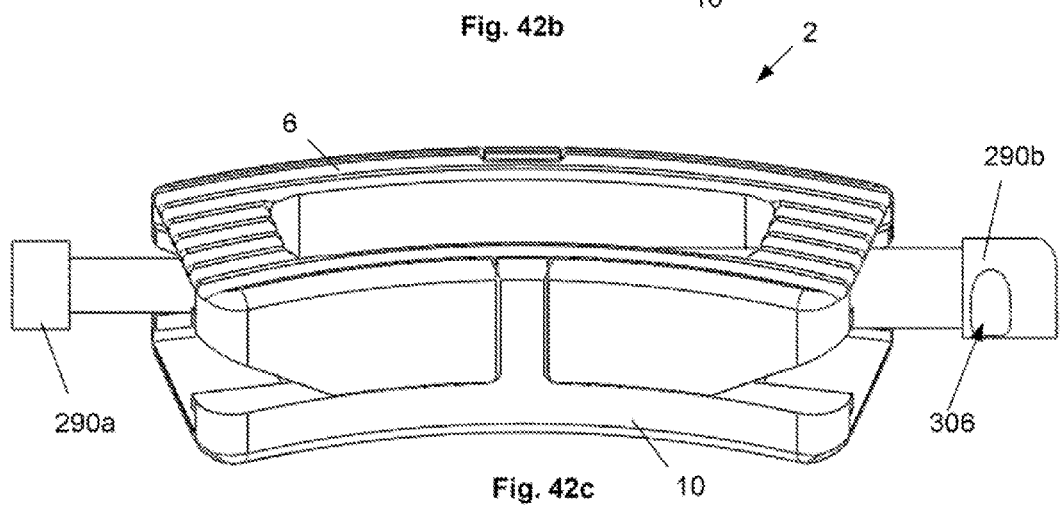

FIGS. 42a through 42c illustrate that the locking pin 162 can have an adjustable length. The locking pin 162 can have a smaller cylinder or proximal locking pin shaft 170a with radially outer threads and a larger outer cylinder or distal locking pin shaft 170b with radially inner threads. The smaller cylinder 170a can helically (e.g., threadably, as a screw or bolt) engage the larger cylinder 170b (e.g., as a nut).

The outside of the smaller cylinder 170a and the inside of the larger cylinder 170b can have a set of slidably engaging longitudinal ribs, slides, rails, guides, or combinations thereof.

The smaller cylinder 170a can be spring loaded with respect to the larger cylinder 170b. The inside of the locking pin 162 can have hydraulic fluid and an internal seal and/or piston so the locking pin 162 can act as a hydraulic damper or shock absorber.

The locking pin 162 can have a distal locking head or plate 290b. The distal locking head 290b can have a larger diameter than the diameter of the distal locking pin shaft 170b and distal ramp port 94a. The distal locking head 290b can be releasably attached to or fixed in or distal to the distal ramp port 94a.

The locking pin 162 can have a proximal locking head or plate 290a. The proximal locking head 290a can have a larger diameter than the diameter of the proximal locking pin shaft 170a and the proximal ramp port 94b. When the locking pin 162 is shortened, the proximal locking pin head 170a can abut or interference fit with the proximal ramp 108, pushing the proximal ramp 108 toward the distal ramp 96, longitudinally contracting and radially expanding the device 2.

The distal locking head 290b can have a key interface 306. The key interface 306 can be a notch, divot, threads, other engagement feature, or combinations thereof. The key interface 306 can slidably receive the attachment key 308, for example after the attachment key 308 is delivered into the distal keyhole 302b. The attachment key 308 can fix the locking pin 162 to the distal ramp 96, for example transferring force from the distal locking plate 290a to the distal ramp, capable of translating the distal ramp 96 proximally and distally with respect to the proximal ramp 108 when the length of the locking pin 162 is expanded and contracted.

FIGS. 43a through 43d and 44a through 44c illustrate that the locking pin 162 can be attached to the distal ramp 96. The locking pin 162 can be longitudinally shortened. The distal ramp 96 can be contracted toward the proximal ramp 108, resulting in a longitudinal contraction of the device and a radial (e.g., height) expansion between the top plate 6 and the bottom plate 10. The ramps 96 and 108 can longitudinally contract along a straight or curved path (e.g., correlating with the shape of the grooves in the top plate, ramps and base plate) toward the center of the device 2.

The top plate 6 can extend in a parallel or non-parallel plane away from the bottom plate 10. A compressive force can be exerted between the proximal and distal ramps 108 and 96 along the longitudinal axis 4.

The attachment key 308 is not shown in FIG. 44b and shown in phantom lines in FIG. 44c for illustrative purposes.

Figure 45A:
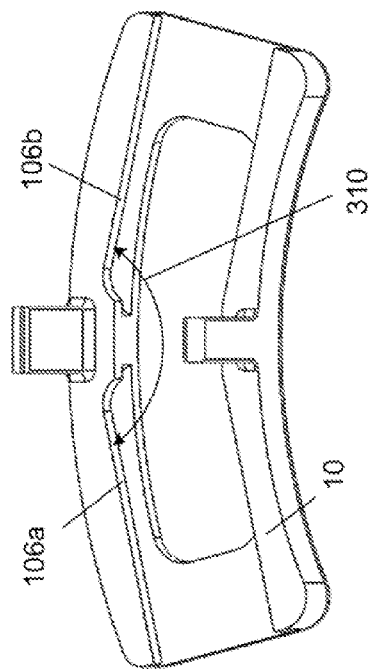
FIGS. 45a and 45b are top and top perspective views, respectively, of a variation of the bottom plate.
Figure 45B:
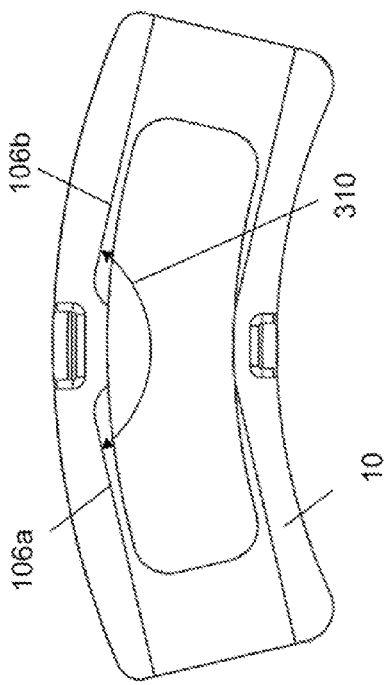

FIGS. 45a and 45b illustrate that the base plate 10 can have proximal base grooves 106a and distal base grooves 106b. The proximal base grooves 106a can be a separate groove than the distal base grooves 106b. The proximal and distal base grooves 106a and 106b can be substantially straight (as shown) or curved.

The longitudinal axis of the proximal base grooves 106a and the longitudinal axis of the distal base grooves 106b can form a base groove angle 310. The base groove angle 310 can be from about 125° to about 175°, more narrowly from about 140° to about 160°, for example about 154°.

Figure 46A:
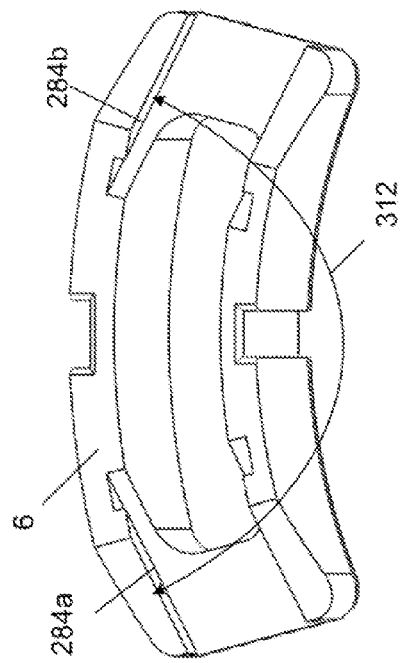
FIGS. 46a and 46b are bottom and bottom perspective views, respectively, of a variation of the top plate.
Figure 46B:
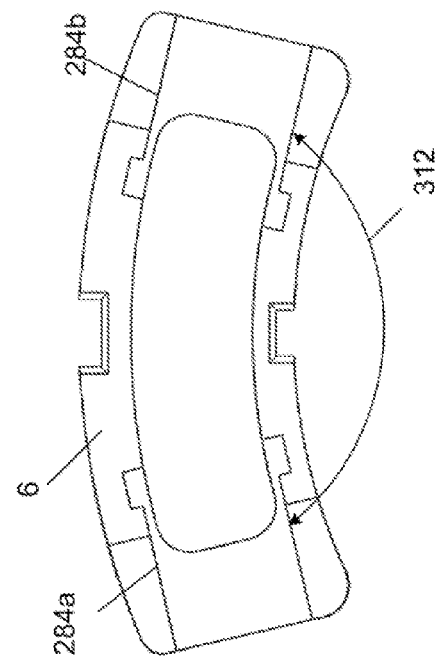

FIGS. 46a and 46b illustrate that the top plate 6 can have proximal top grooves 284a and distal top grooves 284b. The proximal top grooves 284a can be separate from the distal top grooves 284b. The top grooves 284a and 284b can be substantially straight (as shown) or curved.

The longitudinal axis of the proximal top grooves 284a and the longitudinal axis of the distal top grooves 294b can form a top groove angle 312. The top groove angle 312 can be equal to the bottom groove angle 310.

Figure 47A:
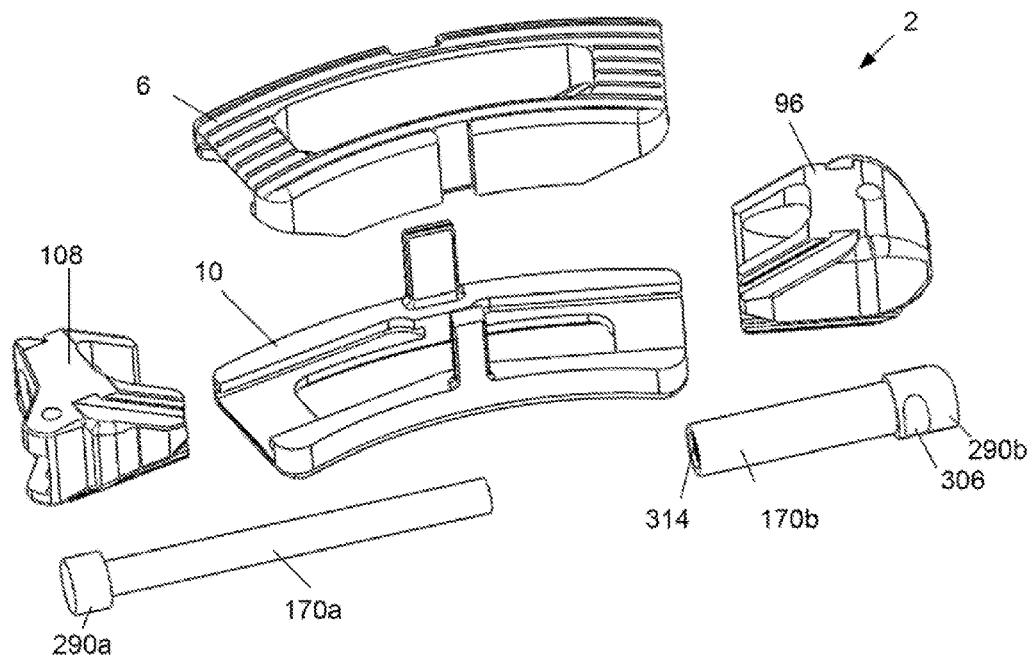
FIGS. 47a and 47b are top perspective and bottom perspective exploded views, respectively, of the variation of the device of FIGS. 41a through 41d.
Figure 47B:
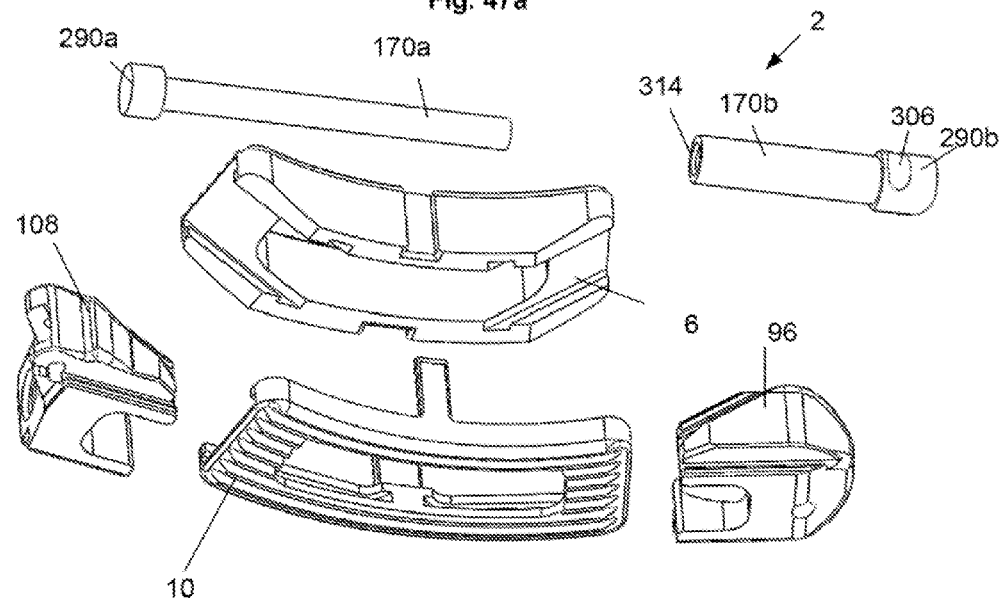
Figure 48A:
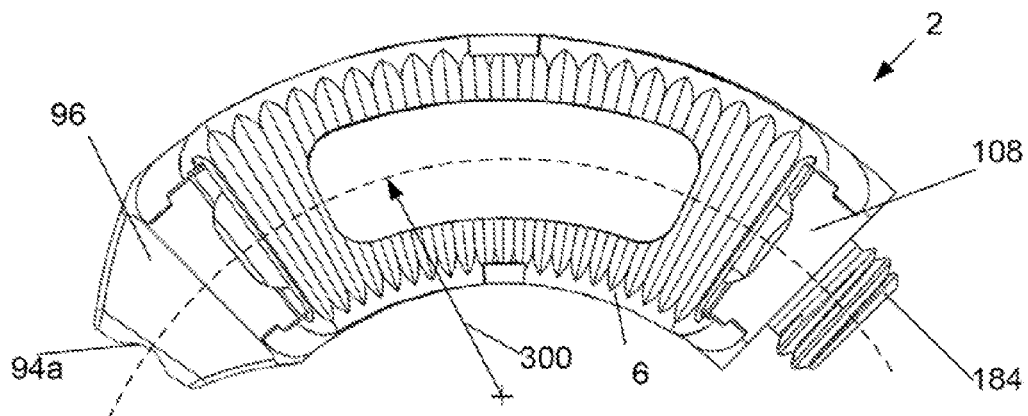
FIGS. 48a through 48d are top, top perspective, side, and bottom perspective views, respectively, of a variation of the device in a longitudinally expanded and radially contracted configuration.
Figure 48B:
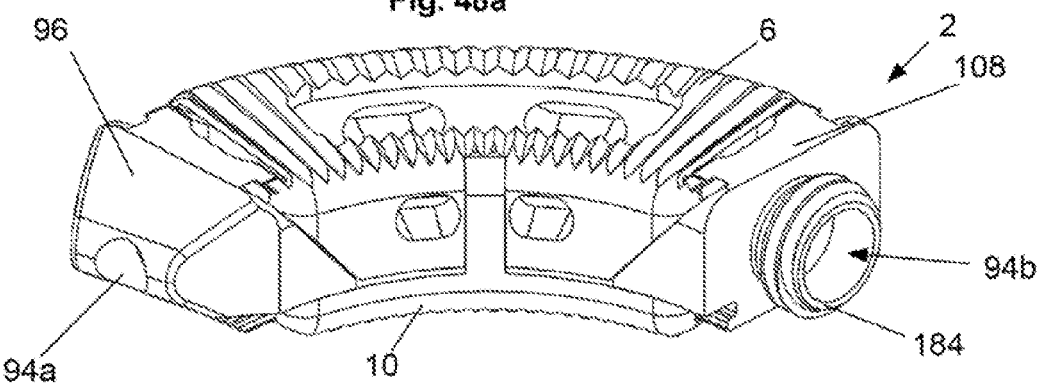
Figure 48C:
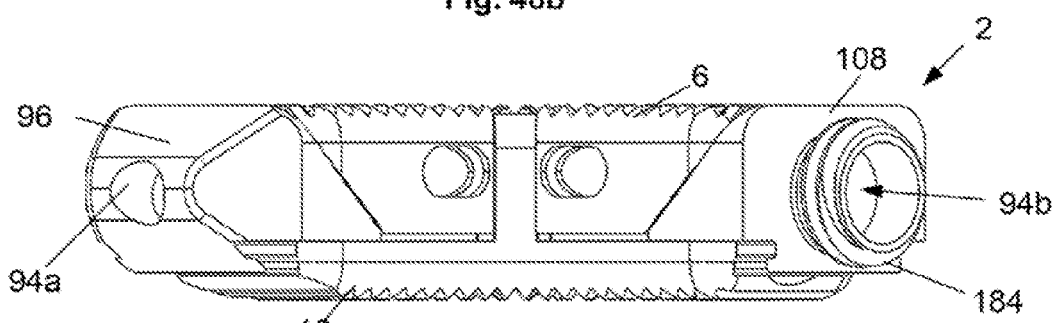
Figure 48D:
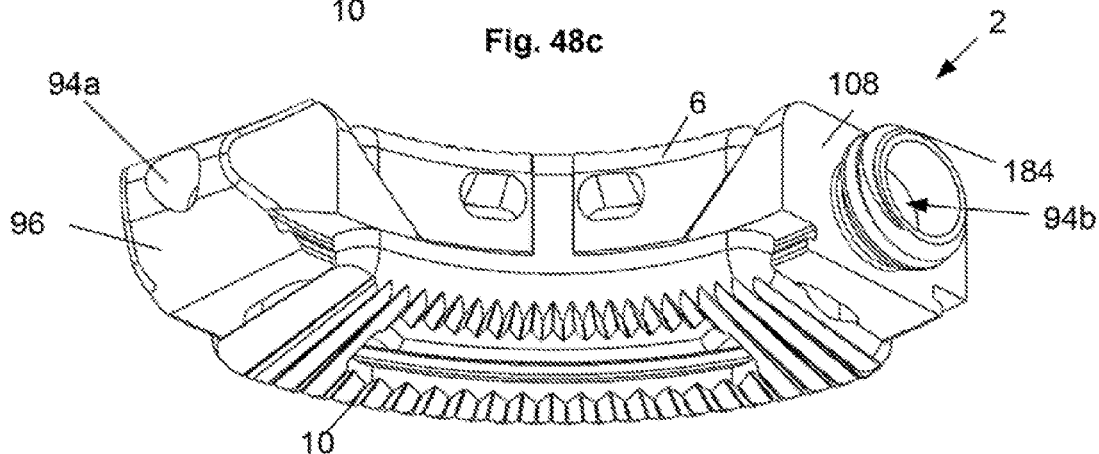
Figure 49A:
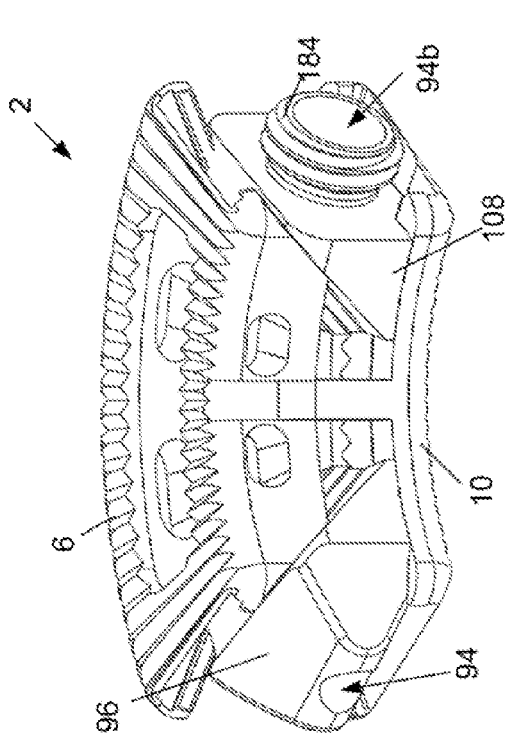
FIGS. 49a through 49d are top, top perspective, side, and bottom perspective views, respectively, of the device of FIGS. 48a through 48d in a longitudinally contracted and radially (e.g., height) expanded configuration.
Figure 49B:
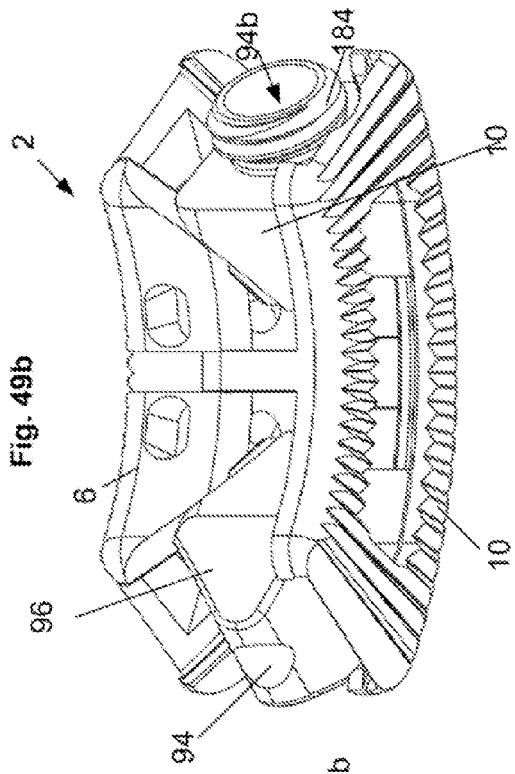
Figure 49C:
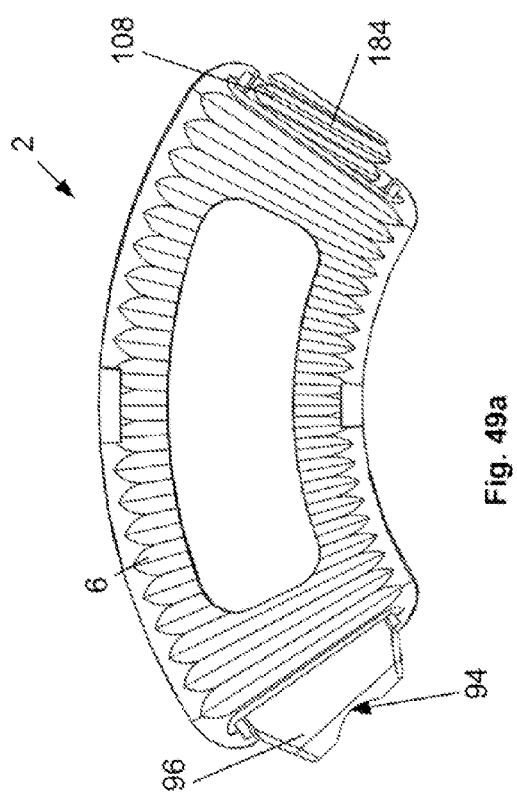
Figure 49D:
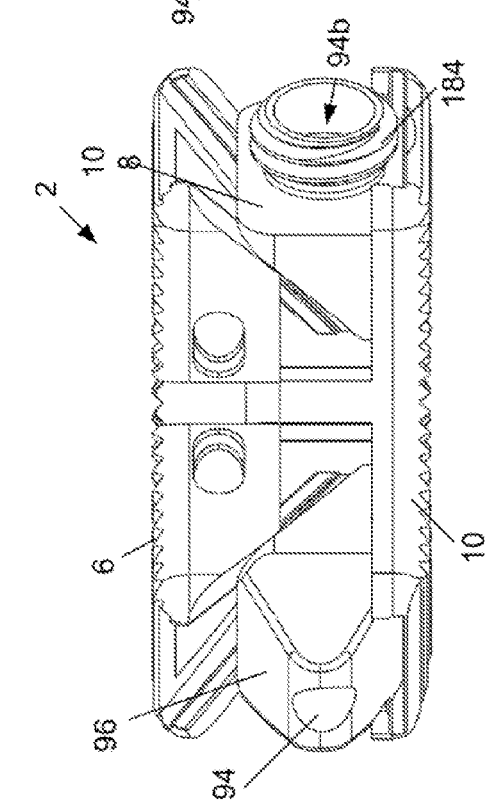

FIGS. 47a and 47b illustrate that the components of the device 2 can be slidably and rotatably assembled.

The outer locking pin shaft 170b can have an outer locking pin shaft channel 314. The inner locking pin shaft 170a can screw, slide, clip or otherwise engage into the outer locking pin shaft channel 314. The inner locking pin shaft 170a can be longitudinally translated within the locking pin shaft channel 314, for example by rotating the inner locking pin shaft 170a with respect to the outer locking pin shaft 170b. The total length of the locking pin 162 can be adjusted.

FIGS. 48a through 48d and 49a through 50a illustrate that the device can have a radius of curvature 300. A compressive force can be exerted onto the ramps 96 and 108 along the longitudinal axis 4. For example, the locking pin and/or deployment tool can be flexible and/or have a rigid shape with a radius of curvature that matches the radius of curvature 300 of the device 2.

The ramps 96 and 108 can longitudinally contract along a curved path, such as along the longitudinal axis 4, toward the center of the device 2. During radial expansion, the top plate 6 can extend in a parallel plane away from the bottom plate 10.

The distal ramp 96 can have threading on inside of a distal ramp port 94a. The distal ramp port 94a can be aligned with the longitudinal axis 4.

The proximal ramp 108 can have threading on the radial exterior and/or interior of the tool connector 184. The proximal ramp 108 can have the tool connector 184, for example extending proximally from the remainder of the device 2. The tool connector 184 can be a cylindral proximal extension from the proximal ramp 108. The threading on the radial outside of the tool connector 184 can, for example, removably attach to a deployment tool.

Figure 50A:
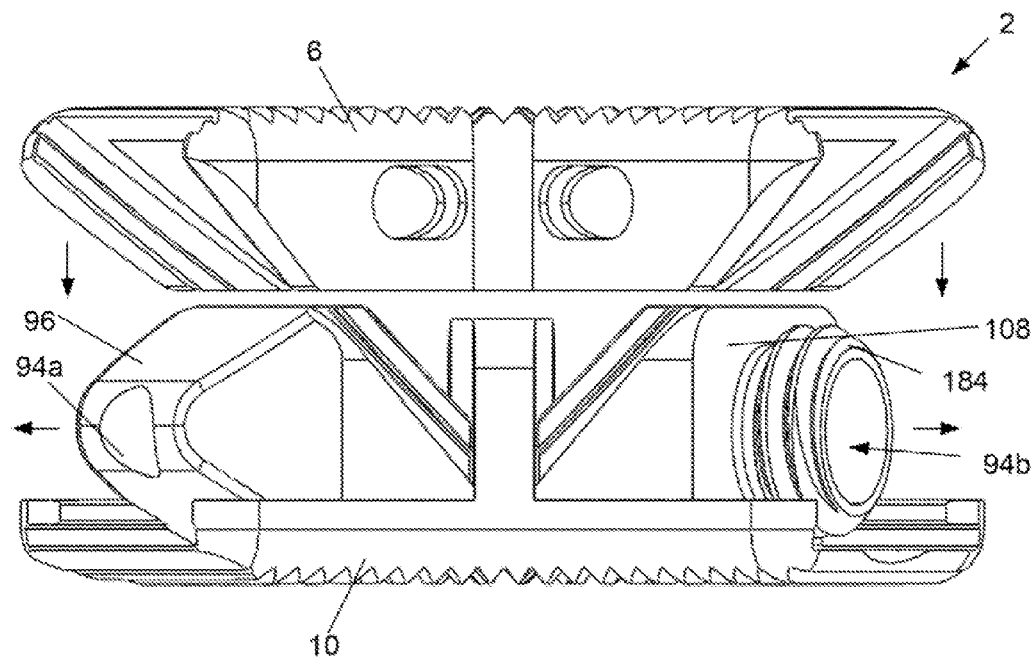
FIGS. 50a and 50b are side and top perspective views of the device of FIGS. 49a through 49d in a longitudinally contracted configuration, with the top plate exploded away from the rest of the device.
Figure 50B:
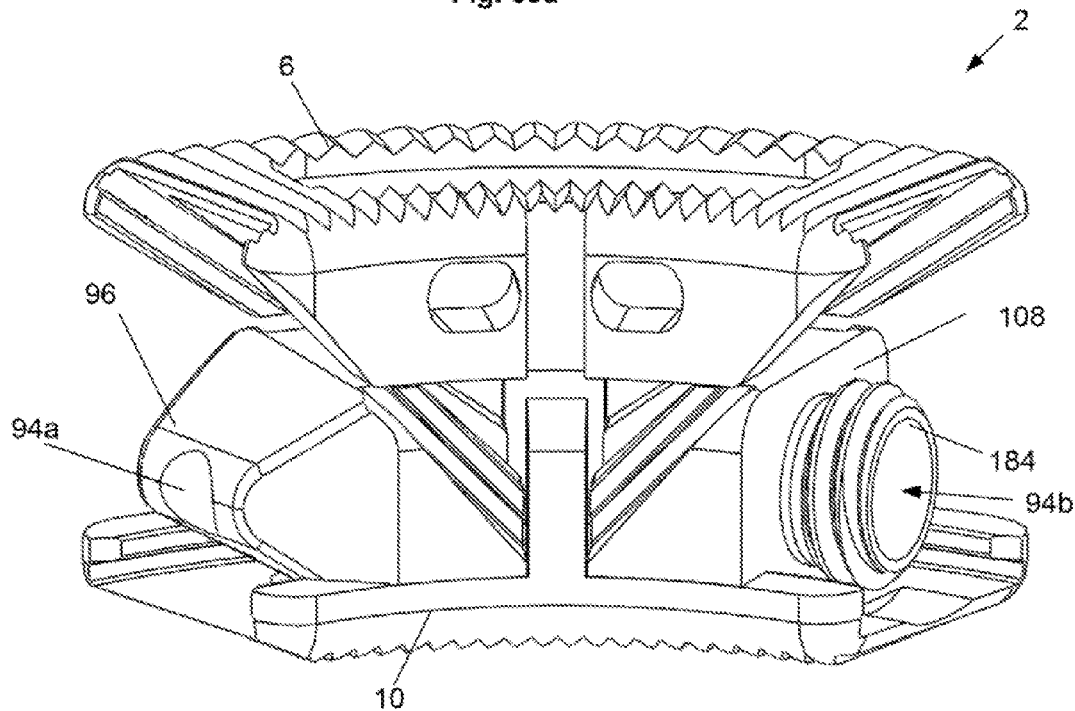

FIGS. 50a and 50b illustrate that the device can be assembled by sliding the iramps 96 and 108 onto the base plate. The ramps 96 and 108 can then be contracted to close to or at their respective inner-most positions on the base plate 10. The top plate 6 can then be delivered, as shown by arrow, onto the ramps 96 and 108. The ramps 96 and 108 can then be slid outward, extending away from the opposite ramp, as shown by arrows, engaging the top plate and pulling the top plate and the bottom plate together.

Figure 51A:
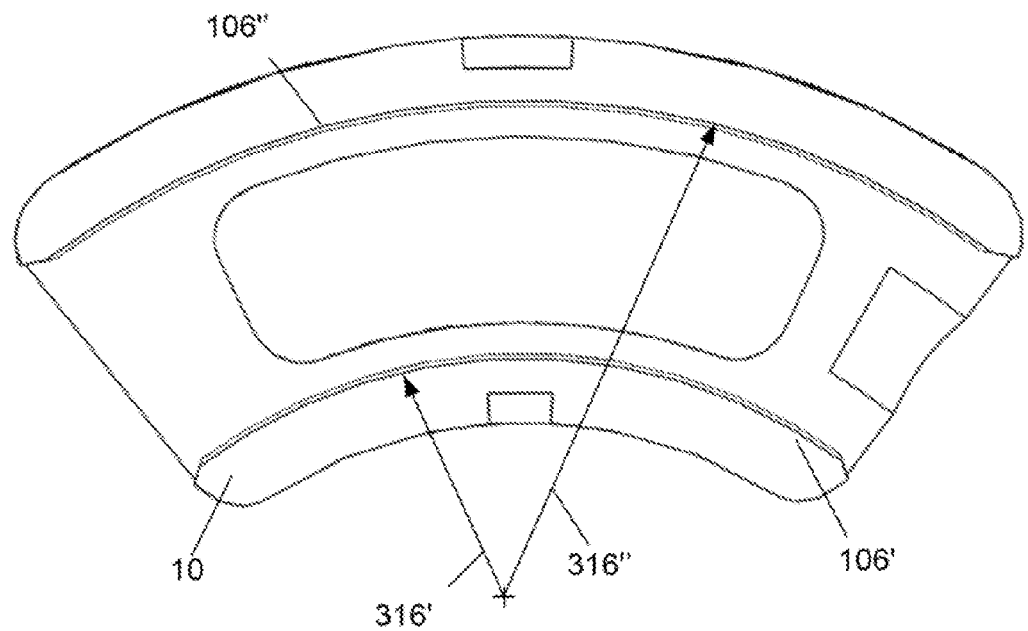
FIGS. 51a and 51b are top and top perspective views, respectively, of a variation of the bottom plate.
Figure 51B:
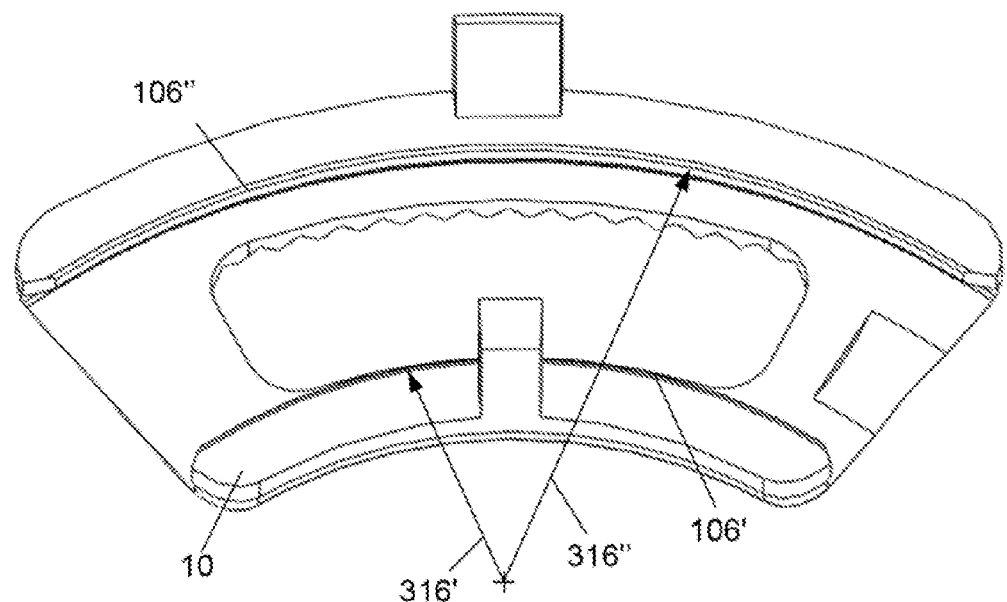

FIGS. 51a and 51b illustrate that the inner base groove 106' and/or outer base groove 106" can be curved along a part or the entire length of the respective base grooves 106. The inner base groove 106' can have an inner base groove radius of curvature 316" from about 1.3 cm (0.5 in.) to about 6.4 cm (2.5 in.) for example about 2.5 cm (1.0 in.). The outer base groove 106" can have an outer base groove radius of curvature 316" from about 2.5 cm (1.0 in.) to about 7.6 cm (3.0 in.), for example about 3.8 cm (1.5 in.).

Figure 52A:
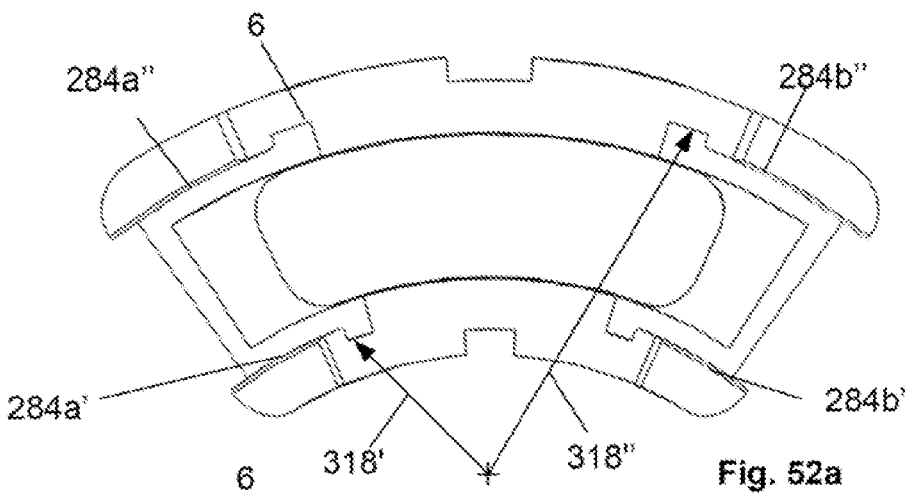
FIGS. 52a through 52c are bottom, bottom perspective, and end perspective views, respectively, of a variation of the top plate.
Figure 52B:
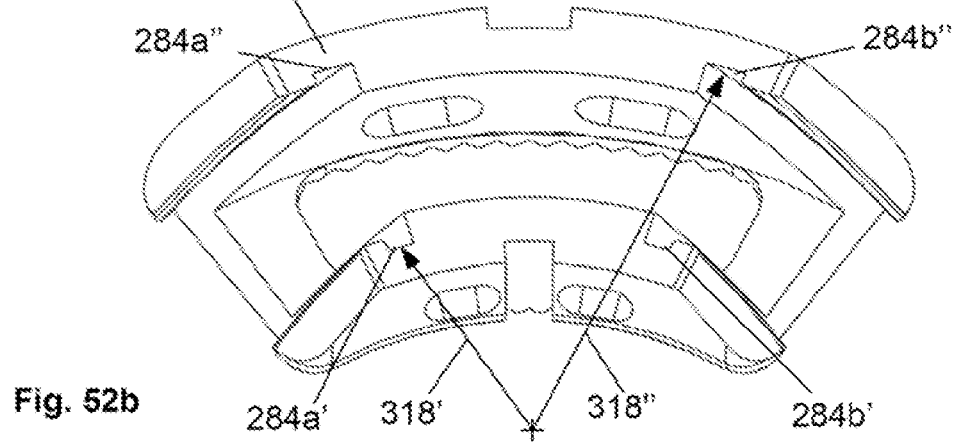
Figure 52C:
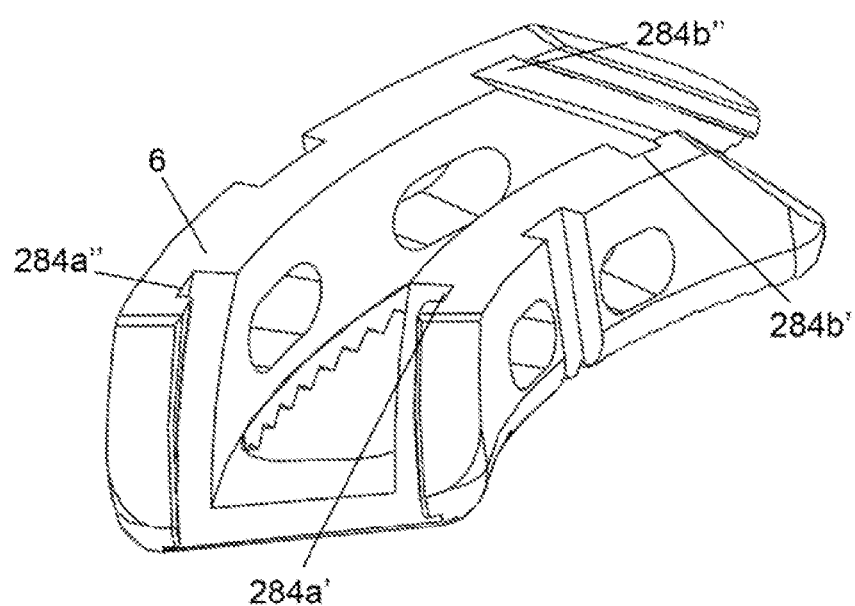
Figures 53A, 53B:
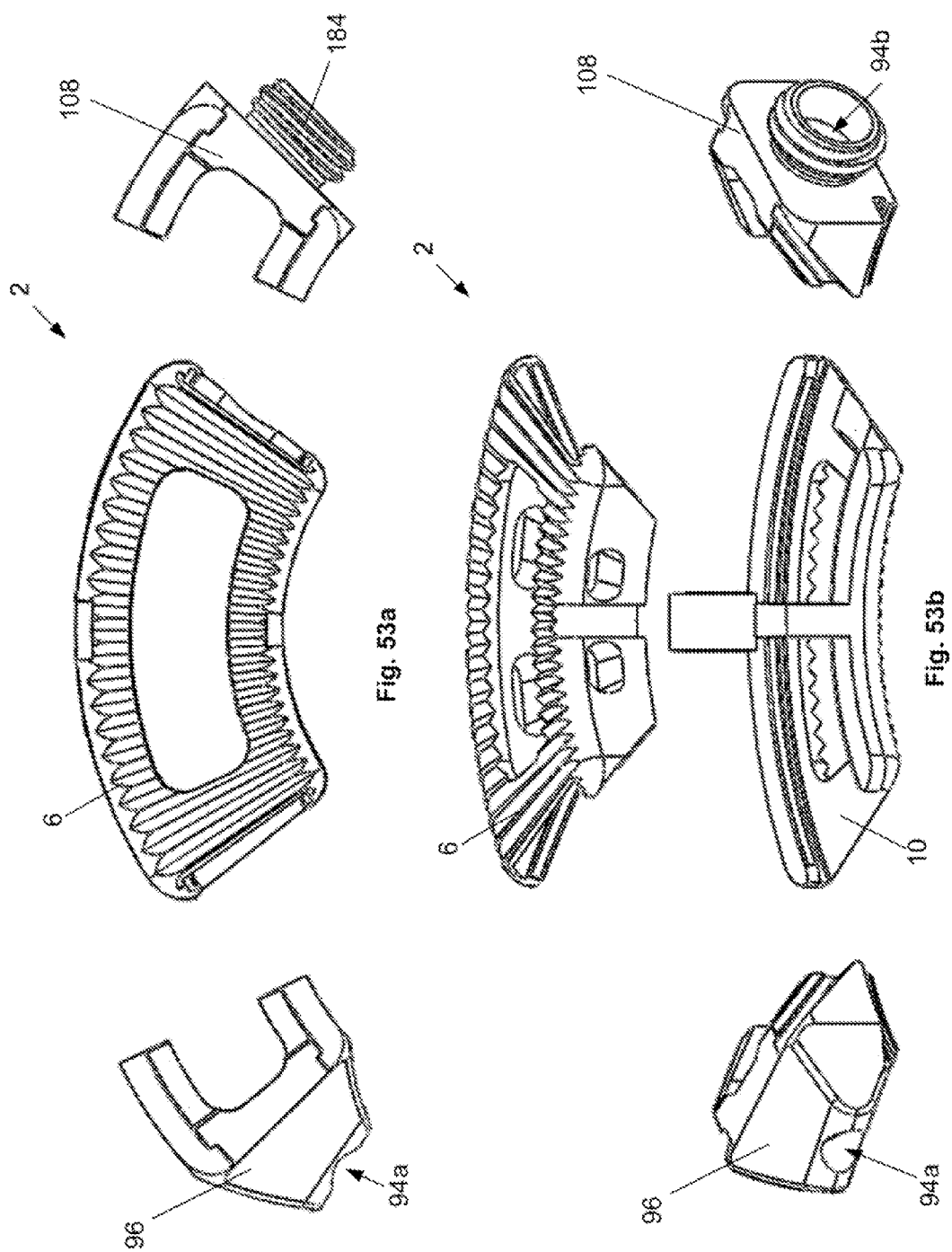

FIGS. 52a through 52c illustrate that the inner proximal and distal top grooves 284a' and 284b' and outer proximal and distal top grooves 284a" and 284b" can be curved along a part or the entire length of the respective grooves.

The inner top grooves 284a' and 284b' can have inner top groove radii of curvature 318' from about 1.3 cm (0.5 in.) to about 6.4 cm (2.5 in.) for example about 2.5 cm (1.0 in.). The inner top groove radii of curvature 318' can be the same or different for the inner proximal and distal top grooves 284a' and 284b'.

The outer top grooves 284a" and 284b" can have outer top groove radii of curvature 318" from about 2.5 cm (1.0 in.) to about 7.6 cm (3.0 in.), for example about 3.8 cm (1.5 in.). The outer top groove radii of curvature 318" can be the same or different for the outer proximal and distal top grooves 284a" and 284b".

FIGS. 53a through 53d illustrate that that the components of the device 2 can be slidably assembled. A deployment tool and/or fixation rod can be inserted into the device after the component are assembled.

The device 2 can have one or more radiopaque and/or echogenic markers. For example, the device 2 can have aligned markers on the top plate 6, middle plate of ramps 108 and 96 and bottom plate. When the device 2 is in a contracted pre-deployment configuration, the markers can be located immediately adjacent to one another, for example appearing as a single marker. When the device 2 is in an expanded configuration, the markers can move apart from each other, indicating to a doctor performing the implantation and deployment procedure using visualization (e.g., x-ray or ultrasound-based) that the device 2 has expanded. Under visualization the markers can also indicate the location and orientation of the device 2.

Method of Using

The devices can be made from PEEK, any medical grade polymer or metal, or any other material disclosed herein. For example, the side ramps can be made from titanium and/or a titanium alloy and the bottom and/or top plates can be made from PEEK. The device can be coated, for example with bone morphogenic protein (BMP), ceramic, and/or any other material disclosed herein, before, during or after deployment into the target site. The device can be deployed less (e.g., minimally) invasively, over the wire, percutaneously, used with a vertebral body replacement or fusion cage, or combinations thereof. The device can be expandable and un-expandable for removal or repositioning.

Figure 54:
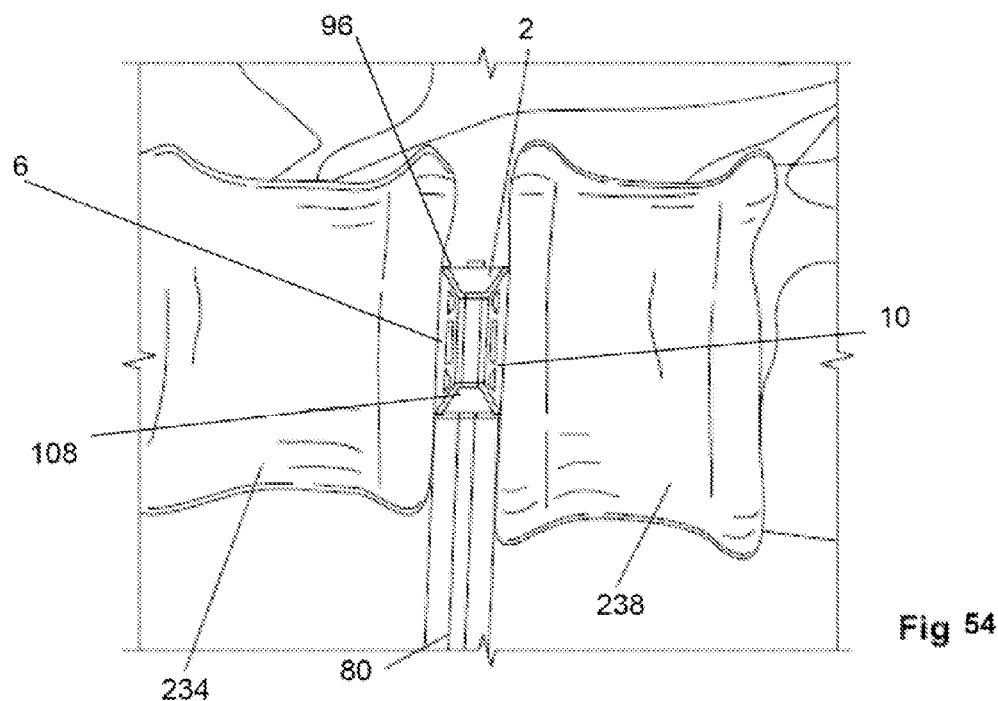
FIG. 54 illustrates a visualization of a variation of a method for deploying the device into the spine between adjacent vertebrae.

FIG. 54 illustrates that the device can be removably attached to a delivery system or deployment tool. The deployment tool can insert the device into the target site. For example the deployment tool can be pushed over a guidewire.

When the device is positioned as desired (e.g., between adjacent vertebral plates) and expanded and/or locked, the deployment tool can then be releases from the device. The device can be configured to lock itself into place with outward expansion, wedging, or interference force when receiving a release force from the deployment tool or otherwise. For example, the device can have unidirectionally sliding teeth oppositely located on the adjacent surfaces of the wedges and plates.

A leader or wire, such as a guidewire, can be inserted or otherwise deployed into the target site, for example, the wire can be percutaneously inserted in a minimally invasive procedure. The wire can be inserted into the intervertebral space, for example between a first vertebral plate and an adjacent, second, vertebral plate. The wire can be anteriorly and/or posteriorly inserted. The wire can be laterally inserted.

Whether or not the device is inserted over or along the wire, the device can be inserted into the target site (e.g., between adjacent vertebral bodies) from an anterior, lateral, posterior, transforaminal approach, or combinations thereof.

FIG. 54 illustrates the deployment tool inserted to a target site in vivo between a first vertebra and a second vertebra. For example, the device can be placed at the target site after a partial or complete discectomy. When the device is in a contracted configuration, the tool can position the device between a first vertebral body of the first vertebra and a second vertebral body of the second vertebra. The device can be inserted into the target site a direction substantially parallel to the surfaces of the vertebral body end plates. The device can be placed between a first vertebral end plate of the first vertebral body and the adjacent second vertebral end plate of the second vertebral body. In this inter-vertebral location, the top plate of the device can be in contact with or directly adjacent to the first vertebral end plate. The bottom plate of the device can be in contact with or directly adjacent to the second vertebral end plate.

Figure 55A:
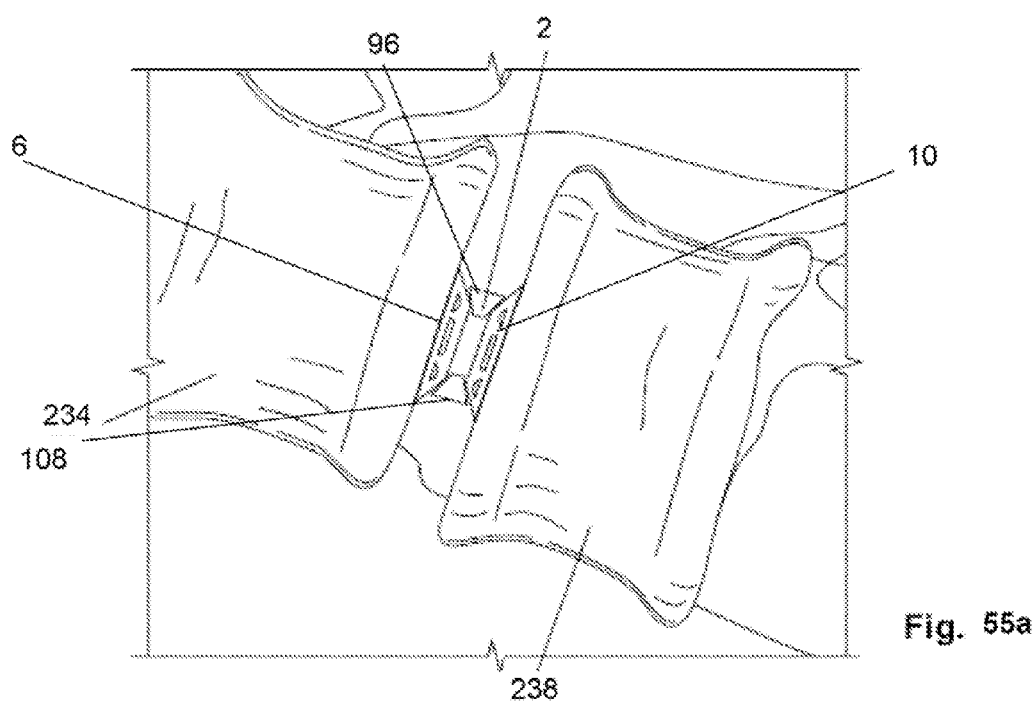
FIGS. 55a and 55b illustrate visualizations of variations of the device deployed into the spine between adjacent vertebrae.
Figure 55B:
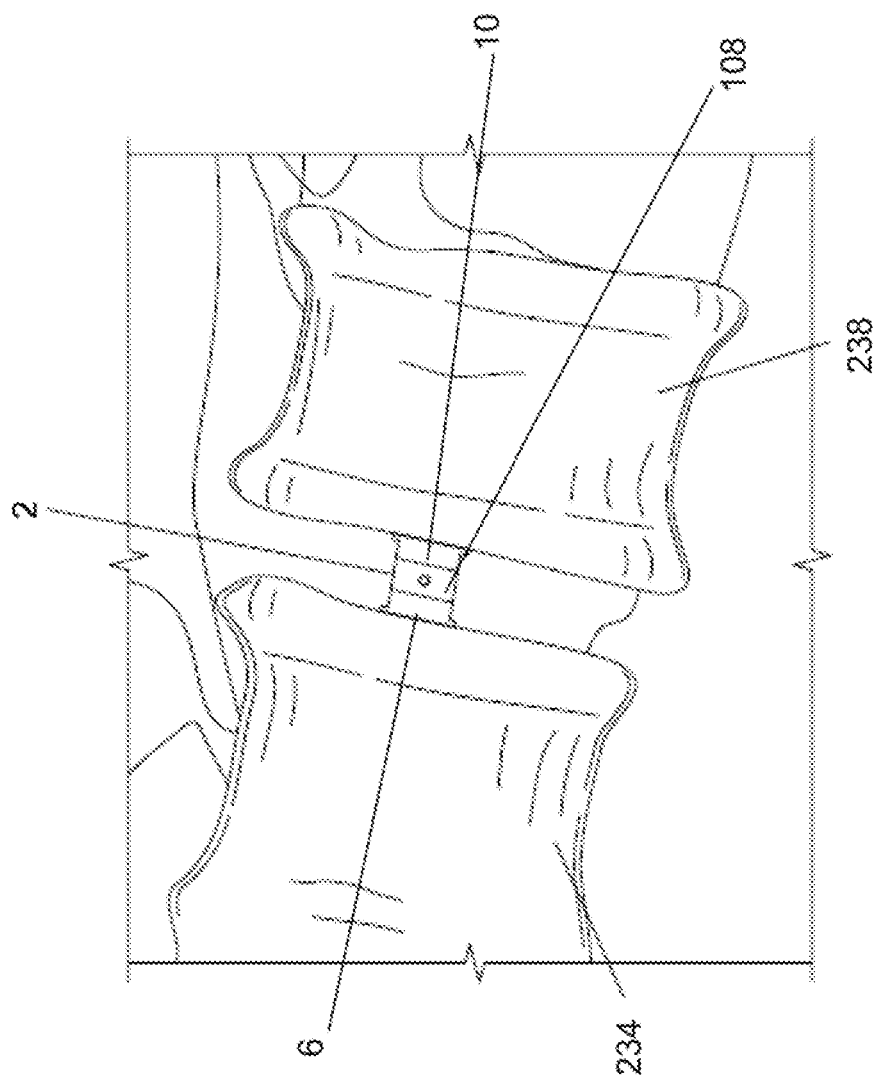

FIGS. 55a and 55b illustrate that the deployment tool can radially expand the device between the first vertebral end plate and the second vertebral end plate. The top plate 6 can press against and/or embed into the first vertebral end plate 234. The bottom plate 10 can press against and/or embed into the second vertebral end plate 238. The device 2 can fuse or fix the first vertebra 234 to the second vertebra 238.

Figure 56A:
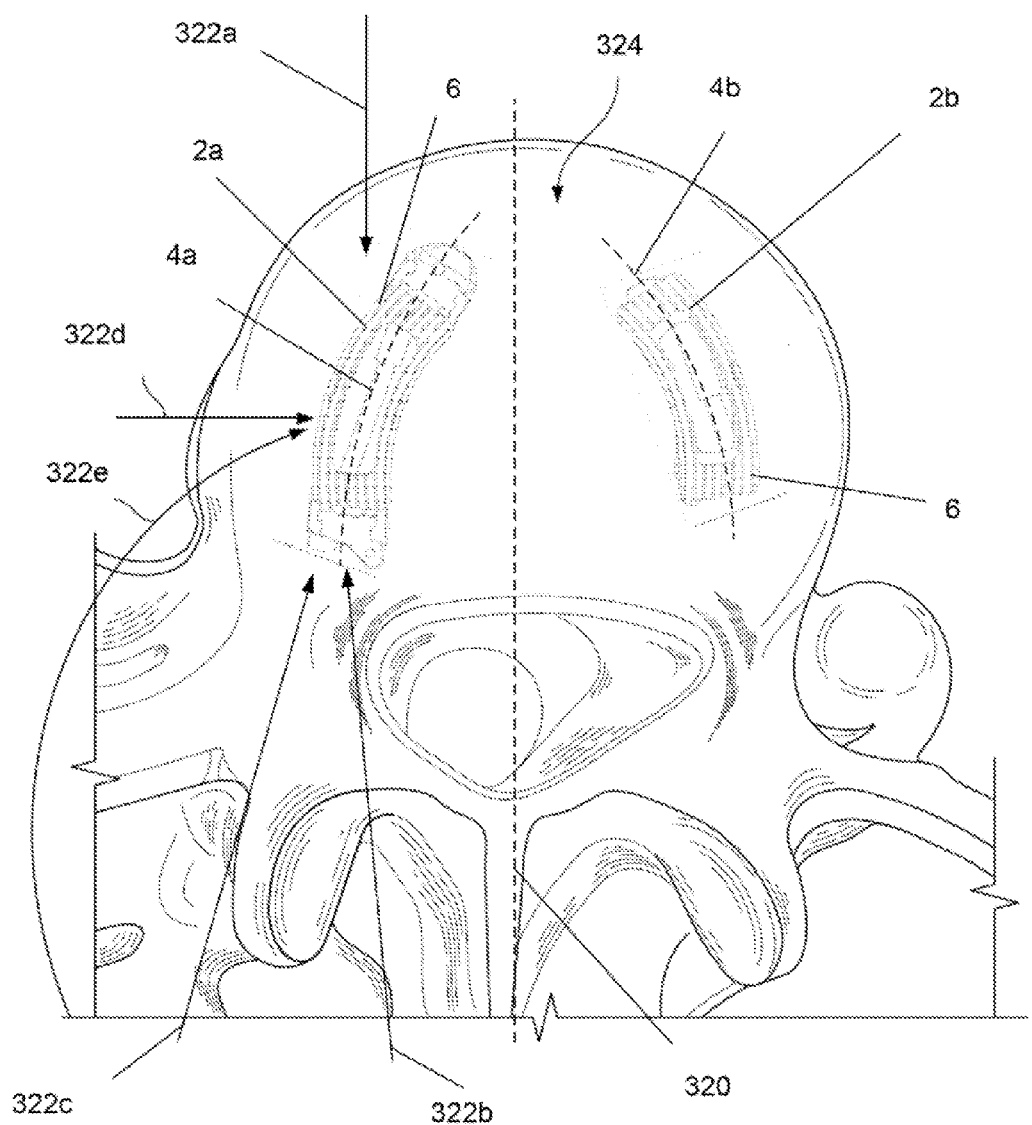
FIGS. 56a and 56b illustrate variations of methods for inserting one or more devices into one or more target sites.

FIG. 56a illustrates that one, two or more devices 2, such as a first device 2a and a second device 2b, can be inserted, deployed and/or implanted the target site, such as in a vertebral body 324 or on a vertebral body 324 (e.g., between adjacent vertebral bodies). The devices 2 can be oriented so the longitudinal axes 4 of the devices 2 are substantially parallel with an anterior-posterior axis 320 of the patient.

The first device 2a can be oriented so the first device longitudinal axis 4a can be substantially parallel with the anterior-posterior axis 320.

The second device 2b can be oriented so the second device longitudinal axis 4b can be substantially parallel with the anterior-posterior axis 320. The second device 2b can be positioned in a substantially symmetric location and angular orientation to the first device 2a with respect to the anterior-posterior axis 320.

The concavity of the radius of curvature 300 of the device can face toward (as shown) or away from the medial direction (i.e., the central anterior-posterior axis 320).

After placed into position at the target site, the device 2 can be longitudinally contracted and radially expanded. For example, as shown, the second device 2b has been radially expanded, and the first device 4a has been delivered to the target site and not yet radially expanded. Multiple devices 4 can be delivered concurrently or sequentially. Multiple devices 4 can be radially expanded sequentially or concurrently.

The devices 4 can be inserted with a surgical technique such as an Anterior Lumbar Interbody Fusion (ALIF), shown by arrow 322a, Posterior Lumbar Interbody Fusion (PLIF), shown by arrow 322b, Transforaminal Lumbar Interbody Fusion (TLIF), shown by arrow 322c, a direct linear lateral delivery, as shown by arrow 322d, a curvilinear lateral delivery initially inserted posteriorly, as shown by arrow 322e, or other methods or combinations thereof.

Operative planning and templating can be performed using MRI and CAT imaging scans to determine what size device fits the patient's anatomy and pathology.

The disc (i.e., intervertebral) space or other target site can then be prepared. For PLIF procedures, the vertebrae can be accessed through an incision in the patient's back (i.e., posterior to the vertebrae). Depending on the number of vertebral levels to be fused, about a 3-6 inch incision can be made in the patient's back. The spinal muscles can then be retracted (or separated), for example, to allow access to the target vertebral discs. The lamina can then be removed (i.e., a laminectomy), for example, to be able to see and access the nerve roots. The facet joints, which can lie directly over the nerve roots, can be trimmed, for example, to allow more room for the nerve roots. The target disc and surrounding tissue can then be removed and the bone surfaces of adjacent vertebrae can be prepared (e.g., cleaned, abraded, debrided, textured, scored, coated with osteogenic powders or other agents, or combinations thereof).

The devices 2 can then be inserted into the target site. One or more devices 2 and/or bone graft (e.g., autograft, allograft, xenograft), BMP, or combinations thereof, can be inserted into the target site or disc space, for example, to promote fusion between the vertebrae. Additional instrumentation (e.g., rods or screws) can also be used at this time to further stabilize the spine.

TLIF can include delivering the device 2 to the spine in a path more from the side of the spinal canal than a PLIF approach and through a midline incision in the patient's back. TLIF can reduce the amount of surgical muscle dissection and can minimizes nerve manipulation required to access the vertebrae, discs and nerves.

TLIF can include removing disc material from the spine and inserting the device(s) 2 and bone graft, BMP, screws, rods, or combinations thereof.

ALIF is performed inserting the from the front (anterior) of the body, usually through a 3-5 inch incision in the lower abdominal area or on the side. This incision may involve cutting through, and later repairing, the muscles in the lower abdomen.

A mini open ALIF approach can be performed. A mini open ALIF can preserves the muscles and allow access to the front of the spine through an incision. This approach maintains abdominal muscle strength and function and can be used to fuse the L5-S1 disc space, for example Once the incision is made and the vertebrae are accessed, and after the abdominal muscles and blood vessels have been retracted, the disc material can be removed. The surgeon can then insert the devices 2 and/or bone graft, rods, screws, BMP, or combinations thereof, for example to stabilize the spine and facilitate fusion.

The target site for the device(s) 2 can be between sacral, lumbar, thoracic, cervical vertebrae, or combinations thereof. The target site can be between other bones, such as intercostal (between ribs), in the knee, elbow, wrist, ankle, or combinations thereof.

Figure 56B:
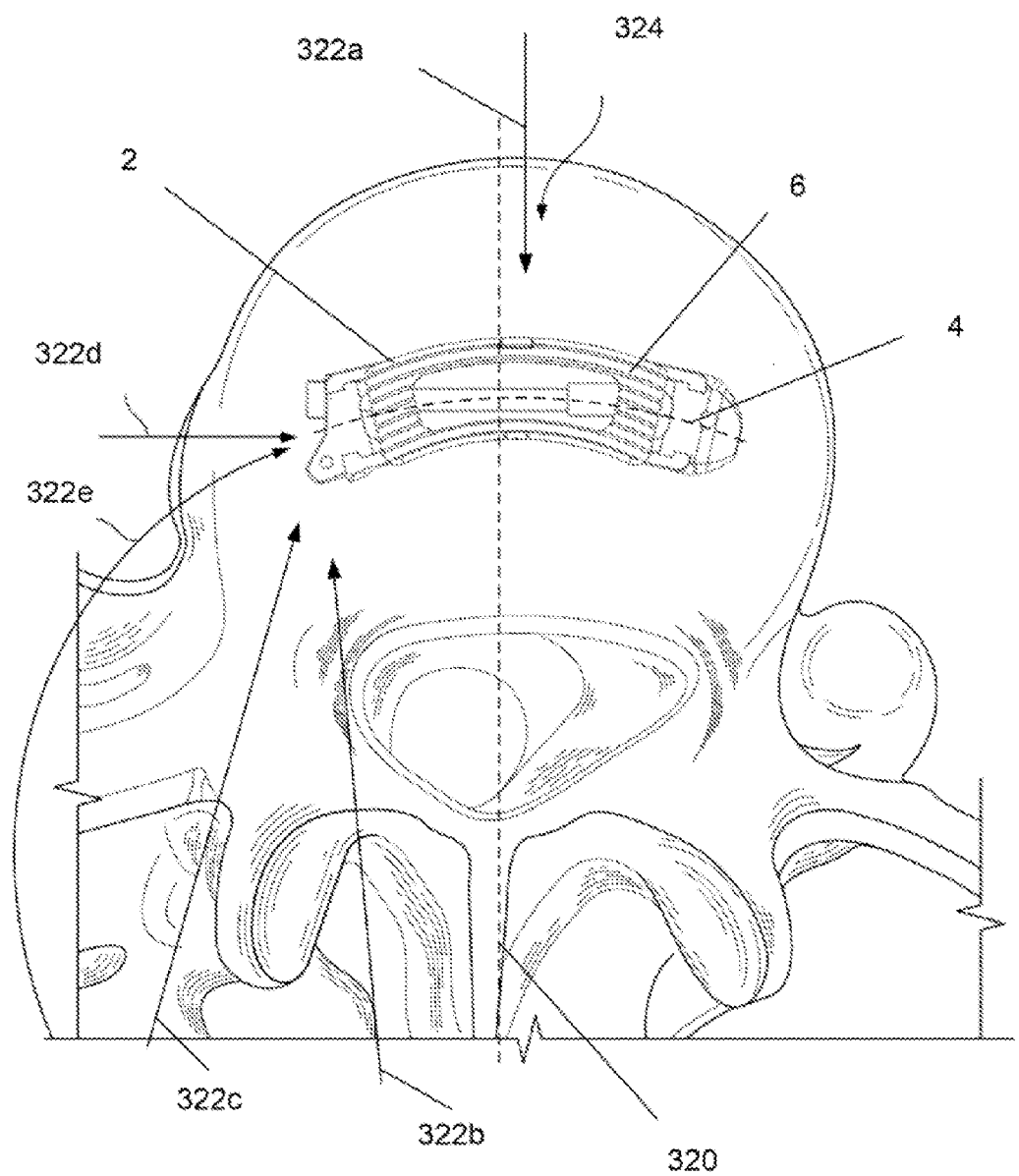

FIG. 56b illustrates that one (as shown) or more devices 2 can be inserted into the target site, such as in a vertebral body or on a vertebral body (e.g., between adjacent vertebral bodies). The longitudinal axis 4 of the device 2 can be oriented substantially perpendicular to the anterior-posterior axis 320 (i.e., parallel to a lateral axis). The concavity of the radius of curvature 300 can face anteriorly or posteriorly.

The device 2 can be filled with a filled before or after radial expansion. Tissue ingrowth can occur into the top plate through the top ports, bottom plate through the bottom ports, and elsewhere through the device.

The device 2 can provide fusion between the adjacent vertebrae. The devices 2 can have radiopaque and/or echogenic visualization markers, for example the markers can be along the top plate, bottom plate, and one or more panels of the plates. The deployment tool can also have one or more markers. The devices 2 can be inserted into multiple interbody target sites of the spine to provide fusion between adjacent vertebral bodies. A first device can be inserted into a first interbody site and a second device can be inserted into a second interbody site. The first and second devices can be inserted bilaterally, for example both devices can be inserted between the same first vertebra and second vertebra from opposite lateral sides.

Any or all elements of the device 2 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON ICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The device 2 can be made from substantially 100% PEEK, substantially 100% titanium or titanium alloy, or combinations thereof.

Any or all elements of the device 2 and/or other devices or apparatuses described herein, can be, have, and/or be completely or partially coated with agents for cell ingrowth.

The device 2 and/or elements of the device and/or other devices or apparatuses described herein can be filled, coated, layered and/or otherwise made with and/or from cements, fillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A method of using an orthopedic support device comprising:
    positioning the device at a target site, wherein the device has a longitudinal axis, and wherein the longitudinal axis has a radius of curvature less than about 40 cm, and wherein the device comprises a first plate, a second plate opposite to the first plate, a first wedge between the first plate and the second plate at a first end of the device, and a second wedge between the first plate and the second plate at a second end of the device, wherein said wedges have respective wedges axes midway between edges of said wedges generally along respective directions of motion of said wedges and a linear actuator having a linear actuator longitudinal axis wherein the linear actuator longitudinal axis extends in a straight line, wherein the linear actuator extends through the first wedge and the second wedge, wherein said linear actuator longitudinal axis forms non-zero angles with respect to said wedge axes wherein the first plate has a first extension extending in the direction of the second plate, and wherein the second plate has a first receiver configured to receive the first extension; and
    expanding the device at the target site, wherein expanding the device at the target site comprises longitudinally moving the first wedge and the second wedge toward the longitudinal middle of the device, and wherein the first extension slides in the first receiver during the expansion of the device.

2. The method of claim 1, wherein expanding further comprises restricting longitudinal translation between the first plate and the second plate.

3. The method of claim 2, wherein the restricting longitudinal translation comprises sliding of the first extension in the first receiver.

4. An implantable orthopedic device comprising:
a first plate having a longitudinal axis having a radius of curvature less than about 40 cm, wherein the radius of curvature is parallel to a second plane coincidental with a top or bottom surface of the first plate;
a second plate opposite to the first plate;
a first wedge between the first plate and the second plate at a first longitudinal end of the device;
a second wedge between the first plate and the second plate at a second longitudinal end of the device; and
a linear actuator having a straight linear actuator longitudinal axis, wherein the linear actuator extends through the first wedge and the second wedge wherein said wedges have respective wedge axes midway between edges of said wedges generally along respective directions of motion of said wedges, and wherein said linear actuator longitudinal axis forms non-zero angles with respect to said wedge axes;
wherein the first plate has a first extension extending in the direction of the second plate, and wherein the second plate has a first receiver configured to slidably receive the first extension; and
wherein the first wedge is longitudinally translatable toward the second wedge, and wherein the first extension slides.

5. The device of claim 4, wherein the first plate has a first plate face substantially defining a first plane, and wherein the first extension extends away from the first plate face in a direction perpendicular to the first plane.

6. The device of claim 5, wherein the second plate has a second plate face substantially defining a second plane, and wherein the first receiver is configured to slidably receive the first extension in a slidable direction perpendicular to the second plane.

7. The device of claim 6, wherein the second plane is parallel with the first plane.

8. An implantable orthopedic device comprising:
a top plate;
a bottom plate;
a first wedge between said first plate and said second plate at a first end of said device, and a second wedge between said first plate and said second plate at a second end of said device, wherein said wedges have respective wedge axes midway between edges of said wedges generally along respective directions of motion of said wedges; and
an actuation mechanism between said top plate and said bottom plate for adjusting a vertical distance between said top plate and said bottom plate, said actuation mechanism comprising a linear actuator having a linear actuator longitudinal axis wherein said linear actuator longitudinal axis extends in a straight line, wherein said linear actuator extends through said first wedge and said second wedge, wherein said linear actuator longitudinal axis forms non-zero angles with respect to said wedge axis,
wherein said top plate and said bottom plate each have a respective long direction and have a respective graft window therethrough defined by a respective graft window perimeter,
wherein said graft window perimeter comprises a first curved side running generally along said long direction of said top plate, and a second curved side opposed to said first curved side and running generally along said long direction of said top plate, and a first end segment generally connecting said first curved side and second curved side, and comprises a second end segment opposed to said first end segment and generally connecting said first curved side and said second curved side, and wherein the first curved side has a radius of curvature, and wherein the radius of curvature is parallel to a plane of the top surface of the top plate and/or a bottom surface of the bottom plate.

9. The implantable orthopedic device of claim 8, wherein said graft window perimeter further comprises rounded corners at places where adjacent ones of said first curved side, said second curved side, said first end segment and said second end segment meet each other.

10. The implantable orthopedic device of claim 8, wherein said linear actuator crosses a space connecting said respective graft windows in said top plate and said bottom plate.

11. The implantable orthopedic device of claim 10, wherein, as observed at a middle of a longitudinal direction of said orthopedic device, said linear actuator crosses said respective graft windows closer to one of said first curved side and said second curved side than to the other of said first curved side and said second curved side.

12. An implantable orthopedic device comprising:
a top plate;
a bottom plate;
a first wedge between said first plate and said second plate at a first end of said device,
and a second wedge between said first plate and said second plate at a second end of said device, wherein said wedges have respective wedge axes midway between edges of said wedges generally along respective directions of motion of said wedges; and
an actuation mechanism located between said top plate and said bottom plate for adjusting a vertical distance between said top plate and said bottom plate, said actuation mechanism comprising a linear actuator for moving said wedges relative to said plates, said linear actuator having a linear actuator longitudinal axis wherein said linear actuator longitudinal axis extends in a straight line, wherein said linear actuator extends through said first wedge and said second wedge, wherein said linear actuator longitudinal axis forms non-zero angles with respect to said wedge axes, and
wherein said device has a longitudinal direction and a longitudinal device axis running generally centrally of said device in said long direction, wherein said longitudinal device axis is curved.

13. An implantable orthopedic device comprising:
a top plate;
a bottom plate, said top plate and said bottom plate having respective long directions and having respective longitudinal axes running generally in said long direction along said plates, said longitudinal axes being curved; and
an actuation mechanism located between said top plate and said bottom plate for adjusting a vertical distance between said top plate and said bottom plate, said actuation mechanism comprising a first wedge and a second wedge located between said first plate and said second plate and comprising a linear actuator for moving said wedges relative to said plates,
wherein said linear actuator has a linear actuator longitudinal axis wherein said linear actuator longitudinal axis extends in a straight line, wherein said linear actuator extends through said first wedge and said second wedge, wherein said wedges have respective wedge axes midway between edges of said wedges generally along respective directions of motion of said wedges, and wherein said linear actuator longitudinal axis forms non-zero angles with respect to said wedge axes, and wherein said longitudinal axes are curved in respective planes that are perpendicular to a direction of said vertical distance between said top plate and said bottom plate.

14. The device of claim 13, wherein said top plate and said bottom plate each have a respective graft window therethrough defined by a respective graft window perimeter, wherein said graft window perimeter comprises a first curved side running generally along said long direction of said top plate, and comprises a second curved side opposed to said first curved side and running generally along said long direction of said top plate, and comprises a first end segment generally connecting said first curved side and said second curved side, and comprises a second end segment opposed to said first end segment and generally connecting said first curved side and said second curved side.

15. The device of claim 14 wherein, as observed at a middle of a longitudinal direction of said orthopedic device, said linear actuator crosses said respective graft windows closer to one of said first curved side and said second curved side than to the other of said first curved side and said second curved side.

16. The device of claim 13, wherein said linear actuator comprises a smaller cylinder having external threads and a larger outer cylinder having internal threads engageable with said external threads.

\* \* \* \* \*

UNITED STATES PATENT AND TRADEMARK OFFICE
CERTIFICATE OF CORRECTION

PATENT NO. : 8,535,380 B2  
APPLICATION NO. : 12/779865  
DATED : September 17, 2013  
INVENTOR(S) : E. Skott Greenhalgh et al.

Page 1 of 1

It is certified that error appears in the above-identified patent and that said Letters Patent is hereby corrected as shown below:

In the Claims:
In Col. 21, claim 16, line 29: replace "haying" with "having"

Signed and Sealed this  
Tenth Day of December, 2013

Margaret A. Focarino  
*Commissioner for Patents of the United States Patent and Trademark Office*